United States Patent [19]

Sonnewald

[11] Patent Number: 5,767,365
[45] Date of Patent: Jun. 16, 1998

[54] DNA SEQUENCES AND PLASMIDS FOR THE PREPARATION OF PLANTS WITH CHANGED SUCROSE CONCENTRATION

[75] Inventor: Uwe Sonnewald, Berlin, Germany

[73] Assignee: Institut fur Genbiologische Forschung Berlin GmbH, Germany

[21] Appl. No.: 356,354

[22] PCT Filed: Jun. 22, 1993

[86] PCT No.: PCT/EP93/01605

§ 371 Date: Dec. 20, 1994

§ 102(e) Date: Dec. 20, 1994

[87] PCT Pub. No.: WO94/00563

PCT Pub. Date: Jan. 6, 1994

[30] Foreign Application Priority Data

Jun. 24, 1992 [DE] Germany .......................... 42 20 758.4

[51] Int. Cl.$^6$ .............................. A01H 5/00; C12N 15/29; C12N 15/82
[52] U.S. Cl. ..................... 800/205; 536/23.6; 435/69.1; 435/172.3; 435/240.4; 435/320.1; 800/DIG. 42
[58] Field of Search .......................... 536/23.6; 800/205, 800/DIG. 42; 435/172.3, 320.1, 240.4, 69.1

[56] References Cited

U.S. PATENT DOCUMENTS 5,387,756  2/1995  Burrell et al. ........................... 800/205

FOREIGN PATENT DOCUMENTS

| 0438904 | 7/1991 | European Pat. Off. . |
| 0455316 | 11/1991 | European Pat. Off. . |
| 0466995 | 1/1992 | European Pat. Off. . |
| 0485044 | 5/1992 | European Pat. Off. . |
| 0530978 | 3/1993 | European Pat. Off. . |

| 9216631 | 10/1992 | WIPO . |

OTHER PUBLICATIONS

The Plant Cell, vol. 3, No. 10, October 1991, pp. 1121–1130, A. C. Worrell et al., "Expression of a Maize Sucrose Phosphate Synthase in Tomato Alters Leaf Carbohydrate Partitioning".

The Plant Journal, vol. 1, No. 1, 1991, pp. 51–58, Quick, W.P., WT al., "The Impact of Decreased Rubisco on Photosynthesis, Growth, Allocation and Storage in Tobacco Plants Which Have Been Transformed With Antisense rbcS".

Plant Physiology, vol. 99, No. 1, May 1992, p. 12, Sonnewald, U., et al., "Molecular Approaches to Influence Sink–Source Interactions in Transgenic Plants".

Biological Abstracts, vol. 55, 1973, Abstract No. 68960, T. Murata, Sucrose Phosphate Synthetase from Various Plant Origins see abstract & Agricultural Biological Chem., vol. 36, No. 11, 1972, pp. 1877–1884.

Biological Abstracts, vol. 80, 1985, Philadelphia, PA US; abstract No. 85644, Sowokinos, J.R. et al., "Translucent Tissue Defects in Solanum Tuberosum: 1. Alterations in Amyloplast Membrane Integrity, Enzyme Activities, Sugars and Starch Content" see abstract & Plant Physiol., vol. 78, No. 3, 1985, pp. 489,494.

Sonnewald et al 1992 (Aug.) Plant Physiol 99:1267–1270.
Finnegan et al 1994 Bio/Technology 12:883–888.

*Primary Examiner*—Patricia R. Moody
*Attorney, Agent, or Firm*—Ostrolenk, Faber, Gerb & Soffen, LLP

[57] ABSTRACT

DNA sequences are described, that by integration in a plant genome cause the activity of the sucrose-phosphate-synthase (SPS) of the plant to be changed, plasmids, containing these DNA sequences as well as transgenic plants that by introduction of the DNA sequences causes changes in the activity of sucrose-phosphate-synthase.

16 Claims, 3 Drawing Sheets

5,767,365

1

DNA SEQUENCES AND PLASMIDS FOR THE PREPARATION OF PLANTS WITH CHANGED SUCROSE CONCENTRATION

FIELD OF THE INVENTION

The present invention relates to DNA sequences and plasmids, containing these DNA sequences, which by integration into a plant genome, cause the activity of the sucrose-phosphate-synthase (SPS) of the plant to be changed and thus affect the sugar metabolism of the plant. The invention further relates to transgenic plants, in which through introduction of the DNA sequences, changes in the activity of the sucrose-phosphate-synthase are produced.

BACKGROUND OF THE INVENTION

Sucrose is of central importance for the plant and serves many functions. For the long distance transport of photoassimilates and/or energy between various organs in plants, sucrose is almost exclusively used. The sucrose which is transported in a specific heterotrophic organ determines the growth and the development of this organ. Thus it is known, e.g. from EP 442 592, that transgenic plants, in which the transport of the sucrose away from the exporting leaves is inhibited by expression of an apoplastic invertase, shows a strong reduction in the growth of e.g. roots or tubers in the case of potato plants. For tobacco plants, the principal importance of sucrose for the long distance transport of energy carriers within the plant is described in von Schaewen et al. 1990, EMBO J 9: 3033–3044.

While it has been clearly shown that a reduction of the amount of sucrose imported in the heterotrophic organs, such as tubers and seeds, leads to loss of yield, it is not known whether an increase in the amount of sucrose in the photosynthetically active parts of the plant, mainly the leaves, leads to a better supply of heterotrophic organs and thus to an increase in yield.

A second central role for sucrose and/or the hexoses, glucose and fructose, which are derived from sucrose, is in the protection of plants against frost damage at low temperatures. Frost damage is one of the main limiting factors in agricultural productivity in the northern hemisphere. Temperatures below freezing lead to the formation of ice crystals. Since the growing ice crystals consist of pure water, water is abstracted from the cells as the temperature falls.

This dehydration has at least two potential damaging results:

a) all dissolved substances within a cell are strongly concentrated and the cell contracts following the loss of water. Highly concentrated salts and organic acids lead to membrane damage;

b) with rehydration from dew, the previously contracted cells reexpand. The cell membrane also expands again. The volume expansion puts a heavy mechanical load on the membrane.

It is thus clear that a freezing/dew cycle can lead to severe membrane damage of the cells and thus to damage to the plant.

It thus appears worth while to hinder the freezing of plant cells. One possible strategy is to increase the formation of osmotically active substances in the cytosol of plant cells. This should lead to a lowering of the freezing point. Osmotically active substances include sucrose and/or the two hexoses which are derived from sucrose.

The increased formation of sucrose and/or the two hexoses at low temperatures is desirable in the growing plant.

Another situation can exist in the harvested parts of a plant, especially in storage. For example, in potato tubers that are stored at 4°–8° C., hexoses (glucose) accumulate. It would appear to be sensible, to see this as the answer to a lowering of the temperature ("cold-sweetening").

The accumulation of sucrose and glucose has in the case of potato tubers economically undesirable results. Increased amounts of reducing sugars, such as glucose, in potatoes which are fried when preparing crisps, chips and the like, leads to an undesirable browning due to the Maillard reaction. Such products with a dark brown color are not strength is strongly dependent on the content of starch and/or its breakdown products which are important in determining the quality characteristics of the potato.

In relation to the economic aspects, sucrose thus possesses three especially important functions:

1 as the transport form for the distant transport of photoassimilates, 2 as an osmotically active substance with the desirable activity of lowering the freezing point in intact, growing plants, and 3 in the undesirable formation of reducing sugars in stored harvested parts of a plant, e.g. the potato tubers, as a result of low temperatures.

The biosynthesis pathways for the formation of sucrose, either from the primary photosynthesis products (in the leaf) or by breakdown of starch (in the storage organs e.g. of potatoes), are known. An enzyme in sucrose metabolism is sucrose-phosphate-synthase (SPS). It forms sucrose-6-phosphate from UDP-glucose and fructose-6-phosphate, which in a second step is converted to sucrose.

The isolation of SPS from maize and the cloning of a cDNA from mRNA from maize tissue is known (EP 466 995). In this application, processes for the purification of a protein such as by centrifuging of homogenates, differential precipitation and chromatography are described. A 300 times enrichment of SPS from plant tissue has been described by Salerno and Pontis (Planta 142: 41–48, 1978).

In view of the significance of SPS for carbohydrate metabolism, it is questionable whether plants can tolerate a reduction in SPS activity in all or in certain organs. It is especially not known whether it is possible to produce transgenic plants with a reduced SPS activity. Also the use of SPS for the modification of the functions of sucrose for lowering the freezing point in intact plants and for the formation of reducing sugars in harvested parts is not known.

For the preparation of plants with reduced SPS activity, i.e. plants with changed sucrose concentration, it is necessary to make available an SPS coding region of such plant species, for which processes are described, whereby transgenic plants can be grown in large numbers. In as much as a reduction of SPS activity can be achieved, by selection from a large amount, the possibility exists of obtaining plants with such a phenotype. Further organ specific promoters for gene expression should exist for the plant species, by which the possibility of an organ specific reduction of the SPS activity could be investigated.

A species which fulfils the stated requirements is *Solanum tuberosum*. The genetic modification of *Solanum tuberosum* by gene transfer using Agrobacteria is well described (Fraley et al., 1985, Crit Rev Plant Sci 4: 1–46). Promoters for leaf specific (Stockhaus et al., 1989, Plant Cell 1: 805–813), tuber specific (EP 375 092) and wound inducing (EP 375 091) gene expression are known.

SUMMARY OF THE INVENTION

The present invention now provides DNA sequences with which changes of SPS activity are actually and demonstrably possible and with which the sucrose concentration in the plant can be modified. It is concerned which include sequences with the coding region of sucrose-phosphate-synthase (SPS) from *Solanum tuberosum*.

These DNA sequences can be introduced in plasmids and thereby combined with steering elements for expression in eukaryotic cells. Such steering elements are, on the one hand, transcription promoters and on the other hand, transcription terminators.

Each plasmid comprises:

a) a suitable promoter, that ensures that the coding sequence is read off at the suitable time point and/or in a specified development stage in the transgenic plants or in specified tissues of transgenic plants.

b) at least one coding sequence, that
   i) is coupled to the promoter so that RNA can be translated into protein, whereby the protein demonstrates enzymatic activity that leads to a modification of the sucrose concentration in the plant, or
   ii) is coupled to the promoter so that the non-coding strand is read off, which leads to the formation of a so-called "anti-sense" RNA, which suppresses the formation of the coding protein of an endogenous gene in the plant which is involved in the sucrose biosynthesis, and c) a non-coding termination sequence that contains the signals for the termination and polyadenylation of the transcript.

The present invention further provides plasmids which include DNA sequences which change the SPS activity in the plant.

The coding sequences named under b) include the SPS sequences with the following nucleotide sequences:

SPS 1 sequence (Seq. ID No.1 No.2):

| | | | | | | |
|---|---|---|---|---|---|---|
| CTATTCTCTC | CCCTCCTTTT | TCTCCTCTCT | TCAACCCCAA | AACTTCCCTT | TCAAAGCCTT | 60 |
| TGCTTTCCCT | TTCTCACTTA | CCCAGATCAA | CTAAGCCAAT | TTGCTGTAGC | CTCAGAAAAC | 120 |
| AGCATTCCCA | GATTGAAAAA | GAATCTTTTT | CAGTACCCAA | AAGTTGGGTT | TCTCATGTCC | 180 |
| AGCAAGGATT | AGCTGCTCTA | GCTATTTCTT | TAGCCCTTAA | TTTTTGTCCA | GTTGTGTCTT | 240 |
| CTGATTCTGC | ATTGGCATCT | GAATTTGATG | TGTTAAATGA | AGGGCCACCA | AAGGACTCAT | 300 |
| ATGTAGTTGA | TGATGCTGGT | GTGCTTAGCA | GGGTGACAAA | GTCTGATTTG | AAGGCATTGT | 360 |
| TGTCTGATGT | GGAGAAGAGA | AAAGGCTTCC | ACATTAATTT | CATCACTGTC | CGCAAGCTCA | 420 |
| CTAGCAAAGC | TGATGCTTTT | GAGTATGCTG | ACCAAGTTTT | GGAGAAGTGG | TACCCTAGTG | 480 |
| TTGAACAAGG | AAATGATAAG | GGTATAGTTG | TGCTTGTTAC | AAGTCAAAAG | GAAGGCGCAA | 540 |
| TAACCGGTGG | CCCTGATTTT | GTAAAGGCCG | TTGGAGATAC | TGTTCTTGAT | GCTACCGTCT | 600 |
| CAGAGAACCT | TCCAGTGTTG | GCTACTGAAG | AGAAGTACAA | TGAAGCAGTT | TTCAGCACTG | 660 |
| CCACACGTCT | TGTTGCAGCC | ATTGATGGCC | TTCCTGATCC | TGGTGGACCC | CAACTCAAGG | 720 |
| ATAACAAAAG | AGAGTCCAAC | TTCAAATCCA | GAGAGGAAAC | TGATGAGAAA | AGAGGACAAT | 780 |
| TCACACTTGT | GGTTGGTGGG | CTGTTAGTGA | TTGCTTTTGT | TGTTCCTATG | GCTCAATACT | 840 |
| ATGCATATGT | TTCAAAGAAG | TGAACTGTCT | GATTCTGGAA | AGTTACATTT | TCGTGAGATT | 900 |
| TGAGTAAGCA | TGTATATTAT | CGTGTACAAA | ATGGTCCATT | CGGAAATGAC | TGATTC | 956 |

| ATG | AGA | TAT | TTA | AAA | AGG | ATA | AAT | ATG | AAG | ATT | TGG | ACC | TCC | CCT | 1001 |
|---|---|---|---|---|---|---|---|---|---|---|---|---|---|---|---|
| Met | Arg | Tyr | Leu | Lys | Arg | Ile | Asn | Met | Lys | Ile | Trp | Thr | Ser | Pro | |
| 1 | | | | 5 | | | | | 10 | | | | | 15 | |

| AAC | ATA | ACG | GAT | ACT | GCC | ATT | TCT | TTT | TCA | GAG | ATG | CTG | ACG | CCA | 1046 |
|---|---|---|---|---|---|---|---|---|---|---|---|---|---|---|---|
| Asn | Ile | Thr | Asp | Thr | Ala | Ile | Ser | Phe | Ser | Glu | Met | Leu | Thr | Pro | |
| | | | | 20 | | | | | 25 | | | | | 30 | |

| ATA | AGT | ACA | GAC | GGC | TTG | ATG | ACT | GAG | ATG | GGG | GAG | AGT | AGT | GGT | 1091 |
|---|---|---|---|---|---|---|---|---|---|---|---|---|---|---|---|
| Ile | Ser | Thr | Asp | Gly | Leu | Met | Thr | Glu | Met | Gly | Glu | Ser | Ser | Gly | |
| | | | | 35 | | | | | 40 | | | | | 45 | |

| GCT | TAT | ATT | ATT | CGC | ATT | CCT | TTT | GGA | CCA | AGA | GAG | AAA | TAT | ATT | 1136 |
|---|---|---|---|---|---|---|---|---|---|---|---|---|---|---|---|
| Ala | Tyr | Ile | Ile | Arg | Ile | Pro | Phe | Gly | Pro | Arg | Glu | Lys | Tyr | Ile | |
| | | | | 50 | | | | | 55 | | | | | 60 | |

| CCA | AAA | GAA | CAG | CTA | TGG | CCC | TAT | ATT | CCC | GAA | TTT | GTT | GAT | GGT | 1181 |
|---|---|---|---|---|---|---|---|---|---|---|---|---|---|---|---|
| Pro | Lys | Glu | Gln | Leu | Trp | Pro | Tyr | Ile | Pro | Glu | Phe | Val | Asp | Gly | |
| | | | | 65 | | | | | 70 | | | | | 75 | |

| GCA | CTT | AAC | CAT | ATT | ATT | CAA | ATG | TCC | AAA | GTT | CTT | GGG | GAG | CAA | 1226 |
|---|---|---|---|---|---|---|---|---|---|---|---|---|---|---|---|
| Ala | Leu | Asn | His | Ile | Ile | Gln | Met | Ser | Lys | Val | Leu | Gly | Glu | Gln | |
| | | | | 80 | | | | | 85 | | | | | 90 | |

| | | | | | | | | | | | | | | |
|---|---|---|---|---|---|---|---|---|---|---|---|---|---|---|
| ATT | GGT | AGT | GGC | TAT | CCT | GTG | TGG | CCT | GTT | GCC | ATA | CAC | GGA | CAT | 1271 |
| Ile | Gly | Ser | Gly | Tyr 95 | Pro | Val | Trp | Pro | Val 100 | Ala | Ile | His | Gly | His 105 | |
| TAT | GCT | GAT | GCT | GGC | GAC | TCA | GCT | GCT | CTC | CTG | TCA | GGT | GCT | TTA | 1316 |
| Tyr | Ala | Asp | Ala | Gly 110 | Asp | Ser | Ala | Ala | Leu 115 | Leu | Ser | Gly | Ala | Leu 120 | |
| AAT | GTA | CCA | ATG | CTT | TTC | ACT | GGT | CAC | TCA | CTT | GGT | AGA | GAT | AAG | 1361 |
| Asn | Val | Pro | Met | Leu 125 | Phe | Thr | Gly | His | Ser 130 | Leu | Gly | Arg | Asp | Lys 135 | |
| TTG | GAG | CAA | CTG | TTG | CGA | CAA | GGT | CGT | TTG | TCA | AAG | GAT | GAA | ATA | 1406 |
| Leu | Glu | Gln | Leu | Leu 140 | Arg | Gln | Gly | Arg | Leu 145 | Ser | Lys | Asp | Glu | Ile 150 | |
| AAC | TCA | ACC | TAC | AAG | ATA | ATG | CGG | AGA | ATA | GAG | GCT | GAA | GAA | TTA | 1451 |
| Asn | Ser | Thr | Tyr | Lys 155 | Ile | Met | Arg | Arg | Ile 160 | Glu | Ala | Glu | Glu | Leu 165 | |
| ACT | CTT | GAT | GCT | TCC | GAA | ATT | GTC | ATC | ACT | AGT | ACA | AGA | CAG | GAG | 1496 |
| Thr | Leu | Asp | Ala | Ser 170 | Glu | Ile | Val | Ile | Thr 175 | Ser | Thr | Arg | Gln | Glu 180 | |
| ATT | GAC | GAG | CAA | TGG | CGT | TTG | TAT | GAT | GGG | TTT | GAT | CCA | ATA | TTA | 1541 |
| Ile | Asp | Glu | Gln | Trp 185 | Arg | Leu | Tyr | Asp | Gly 190 | Phe | Asp | Pro | Ile | Leu 195 | |
| GAG | CGT | AAG | TTA | CGT | GCA | AGG | ATC | AAG | CGC | AAT | GTC | AGC | TGT | TAT | 1586 |
| Glu | Arg | Lys | Leu | Arg 200 | Ala | Arg | Ile | Lys | Arg 205 | Asn | Val | Ser | Cys | Tyr 210 | |
| GGC | AGG | TTT | ATG | CCT | CGT | ATG | GCT | GTA | ATT | CCT | CCT | GGG | ATG | GAG | 1631 |
| Gly | Arg | Phe | Met | Pro 215 | Arg | Met | Ala | Val | Ile 200 | Pro | Pro | Gly | Met | Glu 225 | |
| TTC | CAC | CAT | ATT | GTG | CCA | CAT | GAA | GGT | GAC | ATG | GAT | GGA | GAA | ACA | 1676 |
| Phe | His | His | Ile | Val 230 | Pro | His | Glu | Gly | Asp 235 | Met | Asp | Gly | Glu | Thr 240 | |
| GAA | GGA | AGT | GAA | GAT | GGG | AAG | ACC | CCG | GAT | CCA | CCT | ATT | TGG | GCA | 1721 |
| Glu | Gly | Ser | Glu | Asp 245 | Gly | Lys | Thr | Pro | Asp 250 | Pro | Pro | Ile | Trp | Ala 255 | |
| GAG | ATT | ATG | CGC | TTC | TTT | TCT | AAT | CCA | AGG | AAG | CCT | ATG | ATA | CTC | 1766 |
| Glu | Ile | Met | Arg | Phe 260 | Phe | Ser | Asn | Pro | Arg 265 | Lys | Pro | Met | Ile | Leu 270 | |
| GCA | CTT | GCT | AGG | CCT | GAT | CCC | AAG | AAG | AAC | CTC | ACT | ACT | TTA | GTG | 1811 |
| Ala | Leu | Ala | Arg | Pro 275 | Asp | Pro | Lys | Lys | Asn 280 | Leu | Thr | Thr | Leu | Val 285 | |
| AAA | GCA | TTT | GGT | GAA | TGT | CGT | CCA | TTG | AGA | GAG | CTT | GCT | AAT | CTT | 1856 |
| Lys | Ala | Phe | Gly | Glu 290 | Cys | Arg | Pro | Leu | Arg 295 | Glu | Leu | Ala | Asn | Leu 300 | |
| ACT | TTG | ATA | ATG | GGT | AAT | CGA | GAT | AAT | ATC | GAC | GAA | ATG | TCT | AGC | 1901 |
| Thr | Leu | Ile | Met | Gly 305 | Asn | Arg | Asp | Asn | Ile 310 | Asp | Glu | Met | Ser | Ser 315 | |
| ACC | AAT | TCT | GCA | CTT | CTT | CTT | TCA | ATC | TTG | AAA | ATG | ATA | GAT | AAG | 1946 |
| Thr | Asn | Ser | Ala | Leu 320 | Leu | Leu | Ser | Ile | Leu 325 | Lys | met | Ile | Asp | Lys 330 | |
| TAT | GAT | CTT | TAT | GGT | CAA | GTA | GCT | TAT | CCT | AAA | CAC | CAC | AAG | CAG | 1991 |
| Tyr | Asp | Leu | Tyr | Gly 335 | Gln | Val | Ala | Tyr | Pro 340 | Lys | His | His | Lys | Gln 345 | |
| TCA | GAT | GTT | CCT | GAT | ATC | TAC | CGT | CTT | GCT | GCA | AAG | ACT | AAG | GGT | 2036 |
| Ser | Asp | Val | Pro | Asp 350 | Ile | Tyr | Arg | Leu | Ala 355 | Ala | Lys | Thr | Lys | Gly 360 | |
| GTT | TTT | ATT | AAT | CCA | GCT | TTT | ATT | GAG | CCT | TTT | GGA | CTG | ACT | TTG | 2081 |
| Val | Phe | Ile | Asn | Pro 365 | Ala | Phe | Ile | Glu | Pro 370 | Phe | Gly | Leu | Thr | Leu 375 | |
| ATT | GAG | GCA | GCA | GCT | TAT | GGT | CTC | CCA | ATG | GTA | GCC | ACA | AAA | AAT | 2126 |
| Ile | Glu | Ala | Ala | Ala 380 | Tyr | Gly | Leu | Pro | Met 385 | Val | Ala | Thr | Lys | Asn 390 | |

| | | | | | | | | | | | | | | | | |
|---|---|---|---|---|---|---|---|---|---|---|---|---|---|---|---|---|
| GGA Gly | GGA Gly | CCT Pro | GTT Val | GAT Asp 395 | ATA Ile | CAT His | AGG Arg | GTT Val | CTT Leu 400 | GAC Asp | AAT Asn | GGT Gly | CTC Leu | TTA Leu 405 | | 2171 |
| GTG Val | GAT Asp | CCC Pro | CAT His | GAT Asp 410 | CAG Gln | CAG Gln | GCA Ala | ATT Ile | GCT Ala 415 | GAT Asp | GCT Ala | CTT Leu | TTG Leu | AAG Lys 420 | | 2216 |
| TTG Leu | GTT Val | GCT Ala | GAT Asp | AAG Lys 425 | CAA Gln | CTG Leu | TGG Trp | GCT Ala | AAA Lys 430 | TGC Cys | AGG Arg | GCA Ala | AAT Asn | GGA Gly 435 | | 2261 |
| TTA Leu | AAA Lys | AAT Asn | ATC Ile | CAC His 440 | CTT Leu | TTC Phe | TCA Ser | TGG Trp | CCC Pro 445 | GAG Glu | CAC His | TGT Cys | AAA Lys | ACT Thr 450 | | 2306 |
| TAT Tyr | CTA Leu | TCC Ser | CGG Arg | ATA Ile 455 | GCT Ala | AGC Ser | TGC Cys | AAA Lys | CCA Pro 460 | AGG Arg | CAA Gln | CCA Pro | CGC Arg | TGG Trp 465 | | 2351 |
| CTG Leu | AGA Arg | TCC Ser | ATT Ile | GAT Asp 470 | GAT Asp | GAT Asp | GAT Asp | GAA Glu | AAT Asn 475 | TCA Ser | GAA Glu | ACA Thr | GAT Asp | TCA Ser 480 | | 2396 |
| CCT Pro | AGT Ser | GAT Asp | TCC Ser | TTG Leu 485 | AGA Arg | GAT Asp | ATT Ile | CAT His | GAT Asp 490 | ATA Ile | TCT Ser | CTG Leu | AAT Asn | TTG Leu 495 | | 2441 |
| AGA Arg | TTT Phe | TCA ser | TTA Leu | GAT Asp 500 | GGG Gly | GAA Glu | AAG Lys | AAT Asn | GAC Asp 505 | AAT Asn | AAA Lys | GAA Glu | AAT Asn | GCT Ala 510 | | 2486 |
| GAT Asp | AAT Asn | ACA Thr | TTA Leu | GAC Asp 515 | CCC Pro | GAA Glu | GTT Val | CGA Arg | AGG Arg 520 | AGC Ser | AAG Lys | TTA Leu | GAG Glu | AAT Asn 525 | | 2531 |
| GCT Ala | GTT Val | TTG Leu | TCC Ser | TTA Leu 530 | TCT Ser | AAG Lys | GGT Gly | GCA Ala | CTG Leu 535 | AAG Lys | AGC Ser | ACA Thr | TCA Ser | AAA Lys 540 | | 2576 |
| TCT Ser | TGG Trp | TCG Ser | TCA Ser | GAC Asp 545 | AAG Lys | GCA Ala | GAC Asp | CAA Gln | AAC Asn 550 | CCT Pro | GGT Gly | GCT Ala | GGT Gly | AAA Lys 555 | | 2621 |
| TTC Phe | CCA Pro | GCG Ala | ATT Ile | AGG Arg 560 | AGG Arg | AGG Arg | CGA Arg | CAT His | ATT Ile 560 | TTT Phe | GTT Val | ATT Ile | GCA Ala | GTG Val 565 | | 2666 |
| GAT Asp | TGT Cys | GAT Asp | GCT Ala | AGC Ser 570 | TCA Ser | GGA Gly | CTC Leu | TCT Ser | GGA Gly 575 | AGT Ser | GTG Val | AAA Lys | AAG Lys | ATA Ile 580 | | 2711 |
| TTT Phe | GAG Glu | GCT Ala | GTA Val | GAG Glu 585 | AAG Lys | GAA Glu | AGG Arg | GCA Ala | GAG Glu 590 | GGT Gly | TCC Ser | ATT Ile | GGA Gly | TTT Phe 595 | | 2756 |
| ATC Ile | CTG Leu | GCT Ala | ACA Thr | TCT Ser 600 | TTC Phe | AAT Asn | ATA Ile | TCA Ser | GAA Glu 605 | GTA Val | CAG Gln | TCT Ser | TTC Phe | CTG Leu 610 | | 2801 |
| CTT Leu | TCA Ser | GAG Glu | GGC Gly | ATG Met 615 | AAT Asn | CCT Pro | ACT Thr | GAT Asp | TTT Phe 620 | GAT Asp | GCT Ala | TAC Tyr | ATA Ile | TGC Cys 625 | | 2846 |
| AAT Asn | AGT Ser | GGT Gly | GGT Gly | GAT Asp 630 | CTT Leu | TAT Tyr | TAT Tyr | TCG Ser | TCC Ser 635 | TTC Phe | CAT His | TCT Ser | GAG Glu | CAA Gln 640 | | 2891 |
| AAT Asn | CCT Pro | TTT Phe | GTA Val | GTT Val 645 | GAC Asp | TTG Leu | TAC Tyr | TAT Tyr | CAC His 650 | TCA Ser | CAT His | ATT Ile | GAG Glu | TAT Tyr 655 | | 2936 |
| CGT Arg | TGG Trp | GGG Gly | GGC Gly | GAA Glu 660 | GGA Gly | TTG Leu | AGA Arg | AAG Lys | ACT Thr 665 | TTG Leu | GTG Val | CGT Arg | TGG Trp | GCC Ala 670 | | 2981 |
| GCC Ala | TCT Ser | ATC Ile | ATT Ile | GAT Asp 675 | AAG Lys | AAT Asn | GGT Gly | GAA Glu | AAT Asn 680 | GGA Gly | GAT Asp | CAC His | ATT Ile | GTT Val 685 | | 3026 |

| | | | | | | | | | | | | | | | | |
|---|---|---|---|---|---|---|---|---|---|---|---|---|---|---|---|---|
| GTT Val | GAG Glu | GAT Asp | GAA Glu | GAC Asp 690 | AAT Asn | TCA Ser | GCT Ala | GAC Asp | TAC Tyr 695 | TGC Cys | TAT Tyr | ACT Thr | TTC Phe | AAA Lys 700 | | 3071 |
| GTC Val | TGC Cys | AAG Lys | CCT Pro | GGG Gly 705 | ACG Thr | GTT Val | CCT Pro | CCA Pro | TCT Ser 710 | AAA Lys | GAG Glu | CTT Leu | AGA Arg | AAA Lys 715 | | 3116 |
| GTA Val | ATG Met | CGA Arg | ATT Ile | CAG Gln 720 | GCA Ala | CTT Leu | CGT Arg | TGT Cys | CAC His 725 | GCT Ala | GTT Val | TAT Tyr | TGT Cys | CAA Gln 730 | | 3161 |
| AAT Asn | GGG Gly | AGT Ser | AGG Arg | ATT Ile 735 | AAT Asn | GTG Val | ATC Ile | CCT Pro | GTA Val 740 | CTG Leu | GCA Ala | TCT Ser | CGG Arg | TCC Ser 745 | | 3206 |
| CAA Gln | GCA Ala | CTC Leu | AGG Arg | TAC Tyr 750 | TTA Leu | TAT Tyr | CTG Leu | CGA Arg | TGG Trp 755 | GGA Gly | ATG Met | GAC Asp | TTG Leu | TCG Ser 760 | | 3251 |
| AAG Lys | TTG Leu | GTG Val | GTT Val | TTC Phe 765 | GTC Val | GGA Gly | GAA Glu | AGT Ser | GGT Gly 770 | GAT Asp | ACC Thr | GAT Asp | TAT Tyr | GAA Glu 775 | | 3296 |
| GGA Gly | TTA Leu | ATC Ile | GGT Gly | GGT Gly 780 | CTA Leu | CGC Arg | AAG Lys | GCT Ala | GTC Val 785 | ATA Ile | ATG Met | AAA Lys | GGC Gly | CTC Leu 790 | | 3341 |
| TGC Cys | ACT Thr | AAT Asn | GCA Ala | AGC Ser 795 | AGC Ser | TTA Leu | ATT Ile | CAC His | GGT Gly 800 | AAT Asn | AGG Arg | AAT Asn | TAC Tyr | CCG Pro 805 | | 3386 |
| CTA Leu | TCT Ser | GAT Asp | GTT Val | TTA Leu 810 | CCA Pro | TTC Phe | GAC Asp | AGC Ser | CCT Pro 815 | AAT Asn | GTC Val | ATC Ile | CAA Gln | GCG Ala 820 | | 3431 |
| GAC Asp | GAG Glu | GAA Glu | TGT Cys | AGC Ser 825 | AGC Ser | ACC Thr | GAA Glu | ATC Ile | CGT Arg 830 | TGC Cys | TTA Leu | CTG Leu | GTG Val | AAA Lys 835 | | 3476 |
| CTA Leu | GCG Ala | GTA Val | CTC Leu | AAA Lys 840 | GGA Gly | TAATACCCTT | CCCCCTTTGA | TTGTCAAAAA | | | | | | | | 3524 |

| | | |
|---|---|---|
| CCTATATGAG CTATAAGACT ATGCCATGAA AAGAATGGCC ATCCATTTGG CTTGTCTTTT | 2584 |
| GAAGCTGTTA ATACTTTTCA ACAGACTACA AAATGAGATG AGTCCTTTGA TCCTCTTTAA | 3644 |
| AGGACATAAA AGCTTTATGC AAGAACCAGT GCTGTAAAGT TATAGAATTT CTTTTGCTAT | 3704 |
| ATATGACATT CGACAGAACC TGTTCCGGTT CATCGA | 3740 |

SPS 2 sequence (Seq. ID No.3 and No.4)

| | | | | | | | | | | | |
|---|---|---|---|---|---|---|---|---|---|---|---|
| ATTTTTTTCT CTAAGTTCTC TCTCGCTGTC CTTATCATTT CACCACCTCC ATAAATCTAG | | | | | | | | | | | 60 |
| AAACATCTTT TCTACTCCGT TAATCTCTCT AGCACACGGC GGAGGAGTGC GGCGGAGGAG | | | | | | | | | | | 120 |

| | | | | | | | | | | | | | | | |
|---|---|---|---|---|---|---|---|---|---|---|---|---|---|---|---|
| ATG Met 1 | GCG Ala | GGA Gly | AAC Asn | GAT Asp 5 | TGG Trp | ATT Ile | AAC Asn | AGT Ser | TAC Tyr 10 | TTA Leu | GAG Glu | GCG Ala | ATA Ile | CTG Leu 15 | 165 |
| GAT Asp | GTT Val | GGA Gly | CCA Pro | GGG Gly 20 | CTA Leu | GAT Asp | GAT Asp | AAG Lys | AAG Lys 25 | TCA Ser | TCG Ser | TTG Leu | TTG Leu | TTG Leu 30 | 210 |
| AGA Arg | GAA Glu | AGA Arg | GGG Gly | AGG Arg 35 | TTT Phe | AGT Ser | CCG Pro | ACG Thr | AGG Arg 40 | TAC Tyr | TTT Phe | GTT Val | GAG Glu | GAA Glu 45 | 255 |
| GTT Val | ATT Ile | ACT Thr | GGA Gly | TTC Phe 50 | GAT Asp | GAG Glu | ACT Thr | GAT Asp | TTG Leu 55 | CAT His | CGT Arg | TCG Ser | TGG Trp | ATC Ile 60 | 300 |
| CGA Arg | GCA Ala | CAA Gln | GCT Ala | ACT Thr 65 | CGG Arg | AGT Ser | CCG Pro | CAG Gln | AGA Arg 70 | AGG Arg | AAT Asn | ACT Thr | AGG Arg | CTC Leu 75 | 345 |
| GAG Glu | AAT Asn | ATG Met | TGC Cys | TGG Trp 80 | AGG Arg | ATT Ile | TGG Trp | AAT Asn | TTG Leu 85 | GCT Ala | CGC Arg | CAG Gln | AAA Lys | AAG Lys 90 | 390 |

-continued

| | | | | | | | | | | | | | | |
|---|---|---|---|---|---|---|---|---|---|---|---|---|---|---|
| CAG Gln | CTT Leu | GAG Glu | GGA Gly | GAG Glu 95 | CAA Gln | GCT Ala | CAG Gln | TGG Trp | ATG Met 100 | GCA Ala | AAA Lys | CGC Arg | CGT Arg | CAA Gln 105 | 435 |
| GAA Glu | CGT Arg | GAA Glu | AGA Arg | GGT Gly 110 | CGC Arg | AGA Arg | GAA Glu | GCA Ala | GTT Val 115 | GCT Ala | GAT Asp | ATG Met | TCA Ser | GAG Glu 120 | 480 |
| GAT Asp | CTA Leu | TCT Ser | GAG Glu | GGA Gly 125 | GAG Glu | AAA Lys | GGA Gly | GAT Asp | ATA Ile 130 | GTC Val | GCT Ala | GAC Asp | ATG Met | TCA Ser 135 | 525 |
| TCT Ser | CAT His | GGT Gly | GAA Glu | AGT Ser 140 | ACC Thr | AGA Arg | GGC Gly | CGA Arg | TTG Leu 145 | CCT Pro | AGA Arg | ATC Ile | AGT Ser | TCT Ser 150 | 570 |
| GTT Val | GAG Glu | ACA Thr | ATG Met | GAA Glu 155 | GCA Ala | TGG Trp | GTC Val | AGT Ser | CAG Gln 160 | CAG Gln | AGA Arg | GGA Gly | AAG Lys | AAG Lys 165 | 615 |
| CTT Leu | TAT Tyr | ATC Ile | GTG Val | CTT Leu 170 | ATA Ile | AGT Ser | TTA Leu | CAT His | GGT Gly 175 | TTA Leu | ATT Ile | CGG Arg | GGT Gly | GAG Glu 180 | 660 |
| AAT Asn | ATG Met | GAG Glu | CTT Leu | GGA Gly 185 | CGG Arg | GAT Asp | TCT Ser | GAT Asp | ACT Thr 190 | GGT Gly | GGT Gly | CAG Gln | GTG Val | AAG Lys 195 | 705 |
| TAT Tyr | GTT Val | GTT Val | GAA Glu | CTT Leu 200 | GCG Ala | AGG Arg | GCC Ala | TTA Leu | GGG Gly 205 | TCG Ser | ATG Met | CCA Pro | GGT Gly | GTA Val 210 | 750 |
| TAT Tyr | CGG Arg | GTT Val | GAC Asp | TTG Leu 215 | CTT Leu | ACT Thr | AGA Arg | CAA Gln | GTA Val 220 | TCT Ser | TCA Ser | CCA Pro | GAA Glu | GTA Val 225 | 795 |
| GAT Asp | TGG Trp | AGC Ser | TAT Tyr | GGT Gly 230 | GAG Glu | CCG Pro | ACA Thr | GAG Glu | ATG Met 235 | CTG Leu | ACG Thr | CCA Pro | ATA Ile | AGT Ser 240 | 840 |
| ACA Thr | GAC Asp | GGC Gly | TTG Leu | ATG Met 245 | ACT Thr | GAG Glu | ATG Met | GGG Gly | GAG Glu 250 | AGT Ser | AGT Ser | GGT Gly | GCT Ala | TAT Tyr 255 | 885 |
| ATT Ile | ATT Ile | CGC Arg | ATT Ile | CCT Pro 260 | TTT Phe | GGA Gly | CCA Pro | AGA Arg | GAG Glu 265 | AAA Lys | TAT Tyr | ATT Ile | CCA Pro | AAA Lys 270 | 930 |
| GAA Glu | CAG Gln | CTA Leu | TGG Trp | CCC Pro 275 | TAT Tyr | ATT Ile | CCC Pro | GAA Glu | TTT Phe 280 | GTT Val | GAT Asp | GGT Gly | GCA Ala | CTT Leu 285 | 975 |
| AAC Asn | CAT His | ATT Ile | ATT Ile | CAA Gln 290 | ATG Met | TCC Ser | AAA Lys | GTT Val | CTT Leu 295 | GGG Gly | GAG Glu | CAA Gln | ATT Ile | GGT Gly 300 | 1020 |
| AGT Ser | GGC Gly | TAT Tyr | CCT Pro | GTG Val 305 | TGG Trp | CCT Pro | GTT Val | GCC Ala | ATA Ile 310 | CAC His | GGA Gly | CAT His | TAT Tyr | GCT Ala 315 | 1065 |
| GAT Asp | GCT Ala | GGC Gly | GAC Asp | TCA Ser 320 | GCT Ala | GCT Ala | CTC Leu | CTG Leu | TCA Ser 330 | GGT Gly | GCT Ala | TTA Leu | AAT Asn | GTA Val 335 | 1110 |
| CCA Pro | ATG Met | CTT Leu | TTC Phe | ACT Thr 340 | GGT Gly | CAC His | TCA Ser | CTT Leu | GGT Gly 345 | AGA Arg | GAT Asp | AAG Lys | TTG Leu | GAG Glu 350 | 1155 |
| CAA Gln | CTG Leu | TTG Leu | GCA Ala | CAA Gln 355 | GGT Gly | CGA Arg | AAG Lys | TCA Ser | AAG Lys 360 | GAT Asp | GAA Glu | ATA Ile | AAC Asn | TCA Ser 365 | 1200 |
| ACC Thr | TAC Tyr | AAG Lys | ATA Ile | ATG Met 370 | CGG Arg | AGA Arg | ATA Ile | GAG Glu | GCT Ala 375 | GAA Glu | GAA Glu | TTA Leu | ACT Thr | CTT Leu 380 | 1245 |
| GAT Asp | GCT Ala | TCC Ser | GAA Glu | ATT Ile 385 | GTC Val | ATC Ile | ACT Thr | AGT Ser | ACA Thr 390 | AGA Arg | CAG Gln | GAG Glu | ATT Ile | GAC Asp 395 | 1290 |

| | | | | | | | | | | | | | | |
|---|---|---|---|---|---|---|---|---|---|---|---|---|---|---|
| GAG Glu | CAA Gln | TGG Trp | CGT Arg | TTG Leu 400 | TAT Tyr | GAT Asp | GGG Gly | TTT Phe | GAT Asp 405 | CCA Pro | ATA Ile | TTA Leu | GAG Glu | CGT Arg 410 | 1335 |
| AAG Lys | TTA Leu | CGT Arg | GCA Ala | AGG Arg 415 | ATC Ile | AAG Lys | CGC Arg | AAT Asn | GTC Val 420 | AGC Ser | TGT Cys | TAT Tyr | GGC Gly | AGG Arg 425 | 1380 |
| TTT Phe | ATG Met | CCT Pro | CGT Arg | ATG Met 430 | GCT Ala | GTA Val | ATT Ile | CCT Pro | CCT Pro 435 | GGG Gly | ATG Met | GAG Glu | TTC Phe | CAC His 440 | 1425 |
| CAT His | ATT Ile | GTG Val | CCA Pro | CAT His 445 | GAA Glu | GGT Gly | GAC Asp | ATG Met | GAT Asp 450 | GGT Gly | GAA Glu | ACA Thr | GAA Glu | GGA Gly 455 | 1470 |
| AGT Ser | GAA Glu | GAT Asp | GGG Gly | AAG Lys 460 | ACC Thr | CCG Pro | GAT Asp | CCA Pro | CCT Pro 465 | ATT Ile | TGG Trp | GCA Ala | GAG Glu | ATT Ile 470 | 1515 |
| ATG Met | CGC Arg | TTC Phe | TTT Phe | TCT Ser 475 | AAT Asn | CCA Pro | AGG Arg | AAG Lys | CCT Pro 480 | ATG Met | ATA Ile | CTC Leu | GCA Ala | CTT Leu 485 | 1560 |
| GCT Ala | AGG Arg | CCT Pro | GAT Asp | CCC Pro 490 | AAG Lys | AAG Lys | AAC Asn | CTC Leu | ACT Thr 495 | ACT Thr | TTA Leu | GTG Val | AAA Lys | GCA Ala 500 | 1605 |
| TTT Phe | GGT Gly | GAA Glu | TGT Cys | CGT Arg 505 | CCA Pro | TTG Leu | AGA Arg | GAG Glu | CTT Leu 510 | GCT Ala | AAT Asn | CTT Leu | ACT Thr | TTG Leu 515 | 1650 |
| ATA Ile | ATG Met | GGT Gly | AAT Asn | CGA Arg 520 | GAT Asp | AAT Asn | ATC Ile | GAC Asp | GAA Glu 525 | ATG Met | TCT Ser | AGC Ser | ACC Thr | AAT Asn 530 | 1695 |
| TCT Ser | GCA Ala | CTT Leu | CTT Leu | CTT Leu 535 | TCA Ser | ATC Ile | TTG Leu | AAA Lys | ATG Met 540 | ATA Ile | GAT Asp | AAG Lys | TAT Tyr | GAT Asp 540 | 1740 |
| CTT Leu | TAT Tyr | GGT Gly | CAA Gln | GTA Val 545 | GCT Ala | TAT Tyr | CCT Pro | AAA Lys | CAC His 550 | CAC His | AAG Lys | CAG Gln | TCA Ser | GAT Asp 555 | 1785 |
| GTT Val | CCT Pro | GAT Asp | ATC Ile | TAC Tyr 560 | CGT Arg | CTT Leu | GCT Ala | GCA Ala | AAG Lys 565 | ACT Thr | AAG Lys | GGT Gly | GTT Val | TTT Phe 570 | 1830 |
| ATT Ile | AAT Asn | CCA Pro | GCT Ala | TTT Phe 575 | ATT Ile | GAG Glu | CCT Pro | TTT Phe | GGA Gly 580 | CTG Leu | ACT Thr | TTG Leu | ATT Ile | GAG Glu 585 | 1875 |
| GCA Ala | GCA Ala | GCT Ala | TAT Tyr | GGT Gly 590 | CTC Leu | CCA Pro | ATG Met | GTA Val | GCC Ala 595 | ACA Thr | AAA Lys | AAT Asn | GGA Gly | GGA Gly 600 | 1920 |
| CCT Pro | GTT Val | GAT Asp | ATA Ile | CAT His 605 | AGG Arg | GTT Val | CTT Leu | GAC Asp | AAT Asn 610 | GGT Gly | CTC Leu | TTA Leu | GTG Val | GAT Asp 615 | 1965 |
| CCC Pro | CAT His | GAT Asp | CAG Gln | CAG Gln 620 | GCA Ala | ATT Ile | GCT Ala | GAT Asp | GCT Ala 625 | CTT Leu | TTG Leu | AAG Lys | TTG Leu | GTT Val 630 | 2010 |
| GCT Ala | GAT Asp | AAG Lys | CAA Gln | CTG Leu 635 | TGG Trp | GCT Ala | AAA Lys | TGC Cys | AGG Arg 640 | GCA Ala | AAT Asn | GGA Gly | TTA Leu | AAA Lys 645 | 2055 |
| AAT Asn | ATC Ile | CAC His | CTT Leu | TTC Phe 650 | TCA Ser | TGG Trp | CCC Pro | GAG Glu | CAC His 655 | TGT Cys | AAA Lys | ACT Thr | TAT Tyr | CTA Leu 660 | 2100 |
| TCC Ser | CGG Arg | ATA Ile | GCT Ala | AGC Ser 665 | TGC Cys | AAA Lys | CCA Pro | AGG Arg | CAA Gln 670 | CCA Pro | CGC Arg | TGG Trp | CTG Leu | AGA Arg 675 | 2145 |
| TCC Ser | ATT Ile | GAT Asp | GAT Asp | GAT Asp 680 | GAT Asp | GAA Glu | AAT Asn | TCA Ser | GAA Glu 685 | ACA Thr | GAT Asp | TCA Ser | CCT Pro | AGT Ser 690 | 2190 |

-continued

| | | | | | | | | | | | | | | | |
|---|---|---|---|---|---|---|---|---|---|---|---|---|---|---|---|
| GAT Asp | TCC Ser | TTG Leu | AGA Arg | GAT Asp 695 | ATT Ile | CAT His | GAT Asp | ATA Ile | TCT Ser 700 | CTG Leu | AAT Asn | TTG Leu | AGA Arg | TTT Phe 705 | 2235 |
| TCA Ser | TTA Leu | GAT Asp | GGG Gly | GAA Glu 710 | AAG Lys | AAT Asn | GAC Asp | AAT Asn | AAA Lys 715 | GAA Glu | AAT Asn | GCT Ala | GAT Asp | AAT Asn 720 | 2280 |
| ACA Thr | TTA Leu | GAC Asp | CCC Pro | GAA Glu 725 | GTT Val | CGA Arg | AGG Arg | AGC Ser | AAG Lys 730 | TTA Leu | GAG Glu | AAT Asn | GCT Ala | GTT Val 735 | 2325 |
| TTG Leu | TCC Ser | TTA Leu | TCT Ser | AAG Lys 740 | GGT Gly | GCA Ala | CTG Leu | AAG Lys | AGC Ser 745 | ACA Thr | TCA Ser | AAA Lys | TCT Ser | TGG Trp 750 | 2370 |
| TCG Ser | TCA Ser | GAC Asp | AAG Lys | GCA Ala 755 | GAC Asp | CAA Gln | AAC Asn | CCT Pro | GGT Gly 760 | GCT Ala | GGT Gly | AAA Lys | TTC Phe | CCA Pro 765 | 2415 |
| GCG Ala | ATT Ile | AGG Arg | AGG Arg | AGG Arg 770 | CGA Arg | CAT His | ATT Ile | TTT Phe | GTT Val 775 | ATT Ile | GCA Ala | GTG Val | GAT Asp | TGT Cys 780 | 2460 |
| GAT Asp | GCT Ala | AGC Ser | TCA Ser | GGA Gly 785 | CTC Leu | TCT Ser | GGA Gly | AGT Ser | GTG Val 790 | AAA Lys | AAG Lys | ATA Ile | TTT Phe | GAG Glu 795 | 2505 |
| GCT Ala | GTA Val | GAG Glu | AAG Lys | GAA Glu 800 | AGG Arg | GCA Ala | GAG Glu | GGT Gly | TCC Ser 805 | ATT Ile | GGA Gly | TTT Phe | ATC Ile | CTG Leu 810 | 2550 |
| GCT Ala | ACA Thr | TCT Ser | TTC Phe | AAT Asn 815 | ATA Ile | TCA Ser | GAA Glu | GTA Val | CAG Gln 820 | TCT Ser | TTC Phe | CTG Leu | CTT Leu | TCA Ser 825 | 2595 |
| GAG Glu | GGC Gly | ATG Met | AAT Asn | CCT Pro 830 | ACT Thr | GAT Asp | TTT Phe | GAT Asp | GCT Ala 835 | TAC Tyr | ATA Ile | TGC Cys | AAT Asn | AGT Ser 840 | 2640 |
| GGT Gly | GGT Gly | GAT Asp | CTT Leu | TAT Tyr 845 | TAT Tyr | TCG Ser | TCC Ser | TTC Phe | CAT His 850 | TCT Ser | GAG Glu | CAA Gln | AAT Asn | CCT Pro 855 | 2685 |
| TTT Phe | GTA Val | GTT Val | GAC Asp | TTG Leu 860 | TAC Tyr | TAT Tyr | CAC His | TCA Ser | CAT His 865 | ATT Ile | GAG Glu | TAT Tyr | CGT Arg | TGG Trp 870 | 2730 |
| GGG Gly | GGC Gly | GAA Glu | GGA Gly | TTG Leu 875 | AGA Arg | AAG Lys | ACT Thr | TTG Leu | GTG Val 880 | CGT Arg | TGG Trp | GCC Ala | GCC Ala | TCT Ser 885 | 2775 |
| ATC Ile | ATT Ile | GAT Asp | AAG Lys | AAT Asn 890 | GGT Gly | GAA Glu | AAT Asn | GGA Gly | GAT Asp 895 | CAC His | ATT Ile | GTT Val | GTT Val | GAG Glu 900 | 2820 |
| GAT Asp | GAA Glu | GAC Asp | AAT Asn | TCA Ser 905 | GCT Ala | GAC Asp | TAC Tyr | TGC Cys | TAT Tyr 910 | ACT Thr | TTC Phe | AAA Lys | GTC Val | TGC Cys 915 | 2865 |
| AAG Lys | CCT Pro | GGG Gly | ACG Thr | GTT Val 920 | CCT Pro | CCA Pro | TCT Ser | AAA Lys | GAG Glu 925 | CTT Leu | AGA Arg | AAA Lys | GTA Val | ATG Met 930 | 2910 |
| CGA Arg | ATT Ile | CAG Gln | GCA Ala | CTT Leu 935 | CGT Arg | TGT Cys | CAC His | GCT Ala | GTT Val 940 | TAT Tyr | TGT Cys | CAA Gln | AAT Asn | GGG Gly 945 | 2955 |
| AGT Ser | AGG Arg | ATT Ile | AAT Asn | GTG Val 950 | ATC Ile | CCT Pro | GTA Val | CTG Leu | GCA Ala 955 | TCT Ser | CGG Arg | TCC Ser | CAA Gln | GCA Ala 960 | 3000 |
| CTC Leu | AGG Arg | TAC Tyr | TTA Leu | TAT Tyr 965 | CTG Leu | CGA Arg | TGG Trp | GGA Gly | ATG met 970 | GAC Asp | TTG Leu | TCG Ser | AAG Lys | TTG Leu 975 | 3045 |
| GTG Val | GTT Val | TTC Phe | GTC Val | GGA Gly 980 | GAA Glu | AGT Ser | GGT Gly | GAT Asp | ACC Thr 985 | GAT Asp | TAT Tyr | GAA Glu | GGA Gly | TTA Leu 990 | 3090 |

-continued

| | | | | | | | | | | | | | | |
|---|---|---|---|---|---|---|---|---|---|---|---|---|---|---|
| ATC Ile | GGT Gly | GGT Gly | CTA Leu | CGC Arg 995 | AAG Lys | GCT Ala | GTC Val | ATA Ile | ATG Met 1000 | AAA Lys | GGC Gly | CTC Leu | TGC Cys | ACT Thr 1005 | 3135 |
| AAT Asn | GCA Ala | AGC Ser | AGC Ser | TTA Leu 1010 | ATT Ile | CAC His | GGT Gly | AAT Asn | AGG Arg 1015 | AAT Asn | TAC Tyr | CCG Pro | CTA Leu | TCT Ser 1020 | 3180 |
| GAT Asp | GTT Val | TTA Leu | CCA Pro | TTC Phe 1025 | GAC Asp | AGC Ser | CCT Pro | AAT Asn | GTC Val 1030 | ATC Ile | CAA Gln | GCG Ala | GAC Asp | GAG Glu 1035 | 3225 |
| GAA Glu | TGT Cys | AGC Ser | AGC Ser | ACC Thr 1040 | GAA Glu | ATC Ile | CGT Arg | TGC Cys | TTA Leu 1045 | CTG Leu | GAG Glu | AAA Lys | CTA Leu | GCG Ala 1050 | 3270 |
| GTA Val | CTC Leu | AAA Lys | GGA Gly 1054 | TAA End | TACCCTTCCC | CCTTTGATTG | TCAAAAACCT | | | | | | | | 3315 |

ATATGAGCTA TAAGACTATG CCATGAAAAG AATGGCCATC CATTTGGCTT GTCTTTTGAA    3375

GCTGTTAATA CTTTTCAACA GACTACAAAA TGAGATGAGT CCTTTGATCC TCTTTAAAGG    3435

ACATAAAAGC TTTATGCAAG AACCAGTGCT GTAAAGTTAT AGAATTTCTT TTGCTATATA    3495

TGACATTCGA CAGAACCAGT TCCGGTTCAT CGAGAAAAAG AAATAAATTT CAACTTATAA    3555

ACATGCCTGA TCATGTAAAT TATCATATAC ATCCATCGGA AGGCATTATC GATGGGTTAT    3615

CAGATTTTTT 3625

SPS 3 sequence (Seq. ID No.5 and No.6)

| | | | | | | |
|---|---|---|---|---|---|---|
| ATTTTTT | TCTCTAAATT | CTCTCTCACT | GTCCTTATCA | TTTCACCACC | TCCATAAATC | 57 |
| TAGAAACATC | TTTTCTATTC | CGTTAATCTC | TCTAGCACAC | GGCGGAGTGC | GGCGGAGGAG | 117 |

| | | | | | | | | | | | | | | |
|---|---|---|---|---|---|---|---|---|---|---|---|---|---|---|
| ATG Met 1 | GCG Ala | GGA Gly | AAC Asn | GAC Asp 5 | TGG Trp | ATT Ile | AAC Asn | AGT Ser | TAC Tyr 10 | TTA Leu | GAG Glu | GCG Ala | ATA Ile | CTG Leu 15 | 162 |
| GAT Asp | GTA Val | GGA Gly | CCA Pro | GGG Gly 20 | CTA Leu | GAT Asp | GAT Asp | AAG Lys | AAA Lys 25 | TCA Ser | TCG Ser | TTG Leu | TTG Leu | TTG Leu 30 | 207 |
| AGA Arg | GAA Glu | AGA Arg | GGG Gly | AGG Arg 35 | TTT Phe | AGT Ser | CCG Pro | ACG Thr | AGG Arg 40 | TAC Tyr | TTT Phe | GTT Val | GAG Glu | GAA Glu 45 | 252 |
| GTT Val | ATT Ile | ACT Thr | GGA Gly | TTC Phe 50 | GAT Asp | GAG Glu | ACT Thr | GAT Asp | TTG Leu 55 | CAT His | CGC Arg | TCG Ser | TGG Trp | ATC Ile 60 | 297 |
| CGA Arg | GCA Ala | CAA Gln | GCT Ala | ACT Thr 65 | CGG Arg | AGT Ser | CCG Pro | CAG Gln | GAG Glu 70 | AGG Arg | AAT Asn | ACT Thr | AGG Arg | CTC Leu 75 | 342 |
| GAG Glu | AAT Asn | ATG Met | TGC Cys | TGG Trp 80 | AGG Arg | ATT Ile | TGG Trp | AAT Asn | TTG Leu 85 | GCT Ala | CGC Arg | CAG Gln | AAA Lys | AAG Lys 90 | 387 |
| CAG Gln | CTT Leu | GAG Glu | GGA Gly | GAG Glu 95 | CAA Gln | GCT Ala | CAG Gln | TGG Trp | ATG Met 100 | GCA Ala | AAA Lys | CGC Arg | CGT Arg | CAA Gln 105 | 432 |
| GAA Glu | CGT Arg | GAG Glu | AGA Arg | GGT Gly 110 | CGC Arg | AGA Arg | GAA Glu | GCA Ala | GTT Val 115 | GCT Ala | GAT Asp | ATG Met | TCA Ser | GAG Glu 120 | 477 |
| GAT Asp | CTA Leu | TCT Ser | GAG Glu | GGA Gly 125 | GAG Glu | AAA Lys | GGA Gly | GAT Asp | ATA Ile 130 | GTC Val | GCT Ala | GAC Asp | ATG Met | TCA Ser 135 | 522 |
| TCT Ser | CAT His | GGT Gly | GAA Glu | AGT Ser 140 | ACC Thr | AGA Arg | GGC Gly | CGA Arg | TTG Leu 145 | CCT Pro | AGA Arg | ATC Ile | AGT Ser | TCT Ser 150 | 567 |
| GTT Val | GAG Glu | ACA Thr | ATG Met | GAA Glu | GCA Ala | TGG Trp | GTC Val | AGT Ser | CAG Gln | CAG Gln | AGA Arg | GGA Gly | AAG Lys | AAG Lys | 612 |

|     |     |     |     | 155 |     |     |     |     | 160 |     |     |     |     | 165 |     |      |
| --- | --- | --- | --- | --- | --- | --- | --- | --- | --- | --- | --- | --- | --- | --- | --- | ---- |
| CTT | TAT | ATC | GTG | CTT | ATA | AGT | TTA | CAT | GGT | TTA | ATT | CGG | GGT | GAG |     | 657  |
| Leu | Tyr | Ile | Val | Leu | Ile | Ser | Leu | His | Gly | Leu | Ile | Arg | Gly | Glu |     |      |
|     |     |     |     | 170 |     |     |     |     | 175 |     |     |     |     | 180 |     |      |
| AAT | ATG | GAG | CTT | GGA | CGG | GAT | TCT | GAT | ACT | GGT | GGT | CAG | GTG | AAG |     | 702  |
| Asn | Met | Glu | Leu | Gly | Arg | Asp | Ser | Asp | Thr | Gly | Gly | Gln | Val | Lys |     |      |
|     |     |     |     | 185 |     |     |     |     | 190 |     |     |     |     | 195 |     |      |
| TAT | GTA | GTT | GGA | GCA | ACT | GTT | GCA | CAA | GGT | CGT | TTG | TCA | AAG | GAT |     | 747  |
| Tyr | Val | Val | Gly | Ala | Thr | Val | Ala | Gln | Gly | Arg | Leu | Ser | Lys | Asp |     |      |
|     |     |     |     | 200 |     |     |     |     | 205 |     |     |     |     | 210 |     |      |
| GAA | ATA | AAC | TCA | ACC | TAC | AAG | ATA | ATG | CGG | AGA | ATA | GAG | GCT | GAA |     | 792  |
| Glu | Ile | Asn | Ser | Thr | Tyr | Lys | Ile | Met | Arg | Arg | Ile | Glu | Ala | Glu |     |      |
|     |     |     |     | 215 |     |     |     |     | 220 |     |     |     |     | 225 |     |      |
| GAA | TTA | ACT | CTT | GAT | GCT | TCC | GAA | ATT | GTC | ATC | ACT | AGT | ACA | AGA |     | 837  |
| Glu | Leu | Thr | Leu | Asp | Ala | Ser | Glu | Ile | Val | Ile | Thr | Ser | Thr | Arg |     |      |
|     |     |     |     | 230 |     |     |     |     | 235 |     |     |     |     | 240 |     |      |
| CAG | GAG | ATT | GAC | GAG | CAA | TGG | CGT | TTG | TAT | GAT | GGG | TTT | GAT | CCA |     | 882  |
| Gln | Glu | Ile | Asp | Glu | Gln | Trp | Arg | Leu | Tyr | Asp | Gly | Phe | Asp | Pro |     |      |
|     |     |     |     | 245 |     |     |     |     | 250 |     |     |     |     | 255 |     |      |
| ATA | TTA | GAG | CGT | AAG | TTA | CGT | GCA | AGG | ATC | AAG | CGC | AAT | GTC | AGC |     | 927  |
| Ile | Leu | Glu | Arg | Lys | Leu | Arg | Ala | Arg | Ile | Lys | Arg | Asn | Val | Ser |     |      |
|     |     |     |     | 260 |     |     |     |     | 265 |     |     |     |     | 270 |     |      |
| TGT | TAT | GGC | AGG | TTT | ATG | CCT | CGT | ATG | GCT | GTA | ATT | CCT | CCT | GGG |     | 972  |
| Cys | Tyr | Gly | Arg | Phe | Met | Pro | Arg | Met | Ala | Val | Ile | Pro | Pro | Gly |     |      |
|     |     |     |     | 275 |     |     |     |     | 280 |     |     |     |     | 285 |     |      |
| ATG | GAG | TTC | CAC | CAT | ATT | GTG | CCA | CAT | GAA | GGT | GAC | ATG | GAT | GGT |     | 1017 |
| Met | Glu | Phe | His | His | Ile | Val | Pro | His | Glu | Gly | Asp | Met | Asp | Gly |     |      |
|     |     |     |     | 290 |     |     |     |     | 295 |     |     |     |     | 300 |     |      |
| GAA | ACA | GAA | GGA | AGT | GAA | GAT | GGA | AAG | ACC | CCG | GAT | CCA | CCT | ATT |     | 1062 |
| Glu | Thr | Glu | Gly | Ser | Glu | Asp | Gly | Lys | Thr | Pro | Asp | Pro | Pro | Ile |     |      |
|     |     |     |     | 305 |     |     |     |     | 310 |     |     |     |     | 315 |     |      |
| TGG | GCA | GAG | ATT | ATG | CGC | TTC | TTT | TCT | AAT | CCA | AGG | AAG | CCT | ATG |     | 1107 |
| Trp | Ala | Glu | Ile | Met | Arg | Phe | Phe | Ser | Asn | Pro | Arg | Lys | Pro | Met |     |      |
|     |     |     |     | 320 |     |     |     |     | 330 |     |     |     |     | 335 |     |      |
| ATA | CTC | GCA | CTT | GCT | AGG | CCT | GAT | CCC | AAG | AAG | AAC | CTC | ACT | ACT |     | 1152 |
| Ile | Leu | Ala | Leu | Ala | Arg | Pro | Asp | Pro | Lys | Lys | Asn | Leu | Thr | Thr |     |      |
|     |     |     |     | 340 |     |     |     |     | 345 |     |     |     |     | 350 |     |      |
| TTA | GTG | AAA | GCA | TTT | GGT | GAA | TGT | CGT | CCA | TTG | AGA | GAC | CTT | GCT |     | 1197 |
| Leu | Val | Lys | Ala | Phe | Gly | Glu | Cys | Arg | Pro | Leu | Arg | Asp | Leu | Ala |     |      |
|     |     |     |     | 355 |     |     |     |     | 360 |     |     |     |     | 365 |     |      |
| AAT | CTT | ACT | TTG | ATA | ATG | GGT | AAT | CGA | GAT | AAT | ATC | GAC | GAA | ATG |     | 1242 |
| Asn | Leu | Thr | Leu | Ile | Met | Gly | Asn | Arg | Asp | Asn | Ile | Asp | Glu | Met |     |      |
|     |     |     |     | 370 |     |     |     |     | 375 |     |     |     |     | 380 |     |      |
| TCT | AGC | ACC | AAT | TCT | GCA | CTT | CTT | CTT | TCA | ATC | TTG | AAG | ATG | ATA |     | 1287 |
| Ser | Ser | Thr | Asn | Ser | Ala | Leu | Leu | Leu | Ser | Ile | Leu | Lys | Met | Ile |     |      |
|     |     |     |     | 385 |     |     |     |     | 390 |     |     |     |     | 395 |     |      |
| GAT | AAG | TAT | GAT | CTT | TAT | GGT | CTA | GTA | GCT | TAT | CCT | AAA | CAC | CAC |     | 1332 |
| Asp | Lys | Tyr | Asp | Leu | Tyr | Gly | Leu | Val | Ala | Tyr | Pro | Lys | His | His |     |      |
|     |     |     |     | 400 |     |     |     |     | 405 |     |     |     |     | 410 |     |      |
| AAG | CAG | TCA | GAT | GTT | CCT | GAT | ATC | TAC | CGT | CTT | GCT | GCA | AAG | ACT |     | 1377 |
| Lys | Gln | Ser | Asp | Val | Pro | Asp | Ile | Tyr | Arg | Leu | Ala | Ala | Lys | Thr |     |      |
|     |     |     |     | 415 |     |     |     |     | 420 |     |     |     |     | 425 |     |      |
| AAG | GGT | GTT | TTT | ATT | AAT | CCA | GCT | TTT | ATT | GAG | CCT | TTT | GGA | CTG |     | 1422 |
| Lys | Gly | Val | Phe | Ile | Asn | Pro | Ala | Phe | Ile | Glu | Pro | Phe | Gly | Leu |     |      |
|     |     |     |     | 430 |     |     |     |     | 435 |     |     |     |     | 440 |     |      |
| ACT | TTG | ATT | GAG | GCA | GCA | GCT | TAT | GGT | CTC | CCA | ATG | GTA | GCC | ACA |     | 1467 |
| Thr | Leu | Ile | Glu | Ala | Ala | Ala | Tyr | Gly | Leu | Pro | Met | Val | Ala | Thr |     |      |
|     |     |     |     | 445 |     |     |     |     | 450 |     |     |     |     | 455 |     |      |
| AAA | AAT | GGA | GGA | CCT | GTT | GAT | ATA | CAT | AGG | GTT | CTT | GAC | AAT | GGT |     | 1512 |
| Lys | Asn | Gly | Gly | Pro | Val | Asp | Ile | His | Arg | Val | Leu | Asp | Asn | Gly |     |      |

|   |   |   |   | 460 |   |   |   |   | 465 |   |   |   |   | 470 |   |   |
|---|---|---|---|---|---|---|---|---|---|---|---|---|---|---|---|---|
| CTC | TTA | GTG | GAT | CCC | CAT | GAT | CAG | CAG | GCA | ATT | GCT | GAT | GCT | CTT |   | 1557 |
| Leu | Leu | Val | Asp | Pro 475 | His | Asp | Gln | Gln | Ala 480 | Ile | Ala | Asp | Ala | Leu 485 |   |   |
| TTG | AAG | TTG | GTT | GCT | GAT | AAG | CAA | CTG | TGG | GCT | AAA | TGC | AGG | GCA |   | 1602 |
| Leu | Lys | Leu | Val | Ala 490 | Asp | Lys | Gln | Leu | Trp 495 | Ala | Lys | Cys | Arg | Ala 500 |   |   |
| AAT | GGA | TTA | AAA | AAT | ATC | CAC | CTT | TTC | TCA | TGG | CCC | GAG | CAC | TGT |   | 1647 |
| Asn | Gly | Leu | Lys | Asn 505 | Ile | His | Leu | Phe | Ser 510 | Trp | Pro | Glu | His | Cys 515 |   |   |
| AAA | ACT | TAT | CTA | TCC | CGG | ATA | GCT | AGC | TGC | AAA | CCG | AGG | CAA | CAT |   | 1692 |
| Lys | Thr | Tyr | Leu | Ser 520 | Arg | Ile | Ala | Ser | Cys 525 | Lys | Pro | Arg | Gln | His 530 |   |   |
| TCC | TTG | AGA | GAT | ATT | CAT | GAT | ATA | TCT | CTG | AAT | TTG | AGA | TTT | TCA |   | 1737 |
| Ser | Leu | Arg | Asp | Ile 535 | His | Asp | Ile | Ser | Leu 540 | Asn | Leu | Arg | Phe | Ser 540 |   |   |
| TTA | GAT | GGG | GAA | AAG | AAT | GAC | AAT | AAA | GAA | AAT | GCT | GAT | AAT | ACA |   | 1782 |
| Leu | Asp | Gly | Glu | Lys 545 | Asn | Asp | Asn | Lys | Glu 550 | Asn | Ala | Asp | Asn | Thr 555 |   |   |
| TTA | GAC | CCC | GAA | GTT | CGA | AGG | AGC | AAG | TTA | GAG | AAT | GCT | GTT | TTG |   | 1827 |
| Leu | Asp | Pro | Glu | Val 560 | Arg | Arg | Ser | Lys | Leu 565 | Glu | Asn | Ala | Val | Leu 570 |   |   |
| TCC | TTA | TCT | AAG | GGT | GCA | CTG | AAG | AGC | ACA | TCA | AAA | TCT | TGG | TCG |   | 1872 |
| Ser | Leu | Ser | Lys | Gly 575 | Ala | Leu | Lys | Ser | Thr 580 | Ser | Lys | Ser | Trp | Ser 585 |   |   |
| TCA | GAC | AAG | GCA | GAC | CAA | AAT | CCT | GGT | GCT | GGT | AAA | TTC | CCA | GCG |   | 1917 |
| Ser | Asp | Lys | Ala | Asp 590 | Gln | Asn | Pro | Gly | Ala 595 | Gly | Lys | Phe | Pro | Ala 600 |   |   |
| ATT | AGG | AGG | AGG | CGA | CAT | ATT | TTT | GTT | ATT | GCA | GTG | GAT | TGT | GAT |   | 1962 |
| Ile | Arg | Arg | Arg | Arg 605 | His | Ile | Phe | Val | Ile 610 | Ala | Val | Asp | Cys | Asp 615 |   |   |
| GCT | AGC | TCA | GGA | CTC | TCT | GGA | AGT | ATG | AAA | AAG | ATA | TTT | GAG | GCT |   | 2007 |
| Ala | Ser | Ser | Gly | Leu 620 | Ser | Gly | Ser | Met | Lys 625 | Lys | Ile | Phe | Glu | Ala 630 |   |   |
| GTA | GAG | AAG | GAA | AGG | GCA | GAG | GGT | TCC | ATT | GGA | TTT | ATC | CTT | GCT |   | 2052 |
| Val | Glu | Lys | Glu | Arg 635 | Ala | Glu | Gly | Ser | Ile 640 | Gly | Phe | Ile | Leu | Ala 645 |   |   |
| ACA | TCT | TTC | AAT | ATA | TCA | GAA | GTA | CAT | TCT | TTC | CTG | CTT | TCA | GAG |   | 2097 |
| Thr | Ser | Phe | Asn | Ile 650 | Ser | Glu | Val | Gln | Ser 655 | Phe | Leu | Leu | Ser | Glu 660 |   |   |
| GGC | ATG | AAT | CCT | ACT | GAG | CAA | AAT | CCT | TTT | GTA | GTT | GAC | TTG | TAC |   | 2142 |
| Gly | Met | Asn | Pro | Thr 665 | Glu | Gln | Asn | Pro | Phe 670 | Val | Val | Asp | Leu | Tyr 675 |   |   |
| TAT | CAC | TCA | CAT | ATT | GAG | TAT | CGT | TGG | GGG | GGC | GAA | GGG | TTG | AGA |   | 2187 |
| Tyr | His | Ser | His | Ile 680 | Glu | Tyr | Arg | Trp | Gly 685 | Gly | Glu | Gly | Leu | Arg 690 |   |   |
| AAG | ACT | TTG | GTG | CGT | TGG | GCC | GCC | TCT | ATC | ATT | GAT | AAG | AAT | GGT |   | 2232 |
| Lys | Thr | Leu | Val | Arg 695 | Trp | Ala | Ala | Ser | Ile 700 | Ile | Asp | Lys | Asn | Gly 705 |   |   |
| GAA | AAT | GGA | GAT | CAC | ATT | GTT | GTT | GAG | GAT | GAA | GAC | AAT | TCA | GCT |   | 2277 |
| Glu | Asn | Gly | Asp | His 710 | Ile | Val | Val | Glu | Asp 715 | Glu | Asp | Asn | Ser | Ala 720 |   |   |
| GAC | TAC | TGC | TAT | ACA | TTC | AAA | GTT | TGC | AAG | CCT | GGG | ACG | GTT | CCT |   | 2322 |
| Asp | Tyr | Cys | Tyr | Thr 725 | Phe | Lys | Val | Cys | Lys 730 | Pro | Gly | Thr | Val | Pro 735 |   |   |
| CCA | TCT | AAA | GAA | CTT | AGA | AAA | GTA | ATG | CGA | ATT | CAG | GCA | CTT | CGT |   | 2367 |
| Pro | Ser | Lys | Glu | Leu 740 | Arg | Lys | Val | Met | Arg 745 | Ile | Gln | Ala | Leu | Arg 750 |   |   |
| TGT | CAC | GCT | GTT | TAT | TGT | CAA | AAT | GGG | AGT | AGG | ATT | AAT | GTG | ATC |   | 2412 |
| Cys | His | Ala | Val | Tyr | Cys | Gln | Asn | Gly | Ser | Arg | Ile | Asn | Val | Ile |   |   |

-continued

| | | | | 755 | | | | | 760 | | | | | 765 | | |
|---|---|---|---|---|---|---|---|---|---|---|---|---|---|---|---|---|
| CCT | GTA | CTG | GCA | TCT | CGG | TCC | CAA | GCA | CTC | AGG | TAC | TTA | TAT | CTG | | 2457 |
| Pro | Val | Leu | Ala | Ser | Arg | Ser | Gln | Ala | Leu | Arg | Tyr | Leu | Tyr | Leu | | |
| | | | | 770 | | | | | 775 | | | | | 780 | | |
| CGA | TGG | GGA | ATG | GTC | CCT | GTA | CTG | GCA | TCT | CGG | TCC | CAA | GCA | CTC | | 2502 |
| Arg | Trp | Gly | Met | Val | Pro | Val | Leu | Ala | Ser | Arg | Ser | Gln | Ala | Leu | | |
| | | | | 785 | | | | | 790 | | | | | 795 | | |
| AGG | TAC | TTA | TAT | CTG | CGA | TGG | GGA | ATG | GTC | CCT | GTA | CTG | GCA | TCT | | 2547 |
| Arg | Tyr | Leu | Tyr | Leu | Arg | Trp | Gly | Met | Val | Pro | Val | Leu | Ala | Ser | | |
| | | | | 800 | | | | | 805 | | | | | 810 | | |
| CGG | TCC | CAA | GCA | CTC | AGG | TAC | TTA | TAT | CTG | CGA | TGG | GGA | ATG | GAC | | 2592 |
| Arg | Ser | Gln | Ala | Leu | Arg | Tyr | Leu | Tyr | Leu | Arg | Trp | Gly | Met | Asp | | |
| | | | | 815 | | | | | 820 | | | | | 825 | | |
| TTG | TCG | AAG | TTG | GTG | GTT | TTC | GTC | GGA | GAA | AGT | GGT | GAT | ACC | GAT | | 2637 |
| Leu | Ser | Lys | Leu | Val | Val | Phe | Val | Gly | Glu | Ser | Gly | Asp | Thr | Asp | | |
| | | | | 830 | | | | | 835 | | | | | 840 | | |
| TAT | GAA | GGA | TTG | ATC | GGT | GGT | CTA | CGC | AAG | GCT | GTC | ATA | ATG | AAA | | 2682 |
| Tyr | Glu | Gly | Leu | Ile | Gly | Gly | Leu | Arg | Lys | Ala | Val | Ile | Met | Lys | | |
| | | | | 845 | | | | | 850 | | | | | 855 | | |
| GGA | CTC | TGC | ACT | AAT | GCA | AGC | AGC | TTA | ATT | CAC | GGT | AAT | AGG | AAT | | 2727 |
| Gly | Leu | Cys | Thr | Asn | Ala | Ser | Ser | Leu | Ile | His | Gly | Asn | Arg | Asn | | |
| | | | | 860 | | | | | 865 | | | | | 870 | | |
| TAC | CCG | CTA | TCT | GAT | GTT | TTA | CCA | TTC | GAG | AGC | CCT | AAT | GTC | ATC | | 2772 |
| Tyr | Pro | Leu | Ser | Asp | Val | Leu | Pro | Phe | Glu | Ser | Pro | Asn | Val | Ile | | |
| | | | | 875 | | | | | 880 | | | | | 885 | | |
| CAA | GCG | GAT | GAG | GAA | TGT | AGC | AGC | ACC | GGA | ATC | CGT | TCC | TTA | CTG | | 2817 |
| Gln | Ala | Asp | Glu | Glu | Cys | Ser | Ser | Thr | Glu | Ile | Arg | Ser | Leu | Leu | | |
| | | | | 905 | | | | | 910 | | | | | 915 | | |
| GAG | AAA | CTA | GCG | GTA | CTC | AAA | GGA | TAA | TACCCTTCCC | | CCTTTGATTG | | | | | 2864 |
| Glu | Lys | Leu | Ala | Val | Leu | Lys | Gly | End | | | | | | | | |
| | | | | 920 | | | | | | | | | | | | |

TCAAAAACCT ATATGAGCTA AGATTATGCC ATGAAAAGAA TGGCCATCCA TTTGGCTTGT   2924

CTTTTG   2930

All sequences are cDNA sequences and stem from a CDNA library of leaf tissue. The expression gene is the same in various plant tissues. As a promoter, there can generally be used any promoter which is active in plants. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters are e.g. the promoter of the 35S RNA of the cauliflower mosaic virus, the patatin promoter B33 (Rocha-Sosa et al. (1989) EMBO J 8: 23–29) or a promoter that ensures expression only in photosynthetically active tissues. Other promoters can be used which ensure expression only in specified organs, such as the root, tuber, seed, stem or specified cell types such as mesophyllic, epidermal or transport cells. For hindering cold sweetening, suitable promoters are those which ensure an activation of the transcription is stored in harvested parts of the plants. For this, there can be considered cold induced promoters or such promoters that become active during the transition of the tuber from the phase where it stores material to the phase where it gives up material.

DETAILED DESCRIPTION OF THE INVENTION

Figure 1:
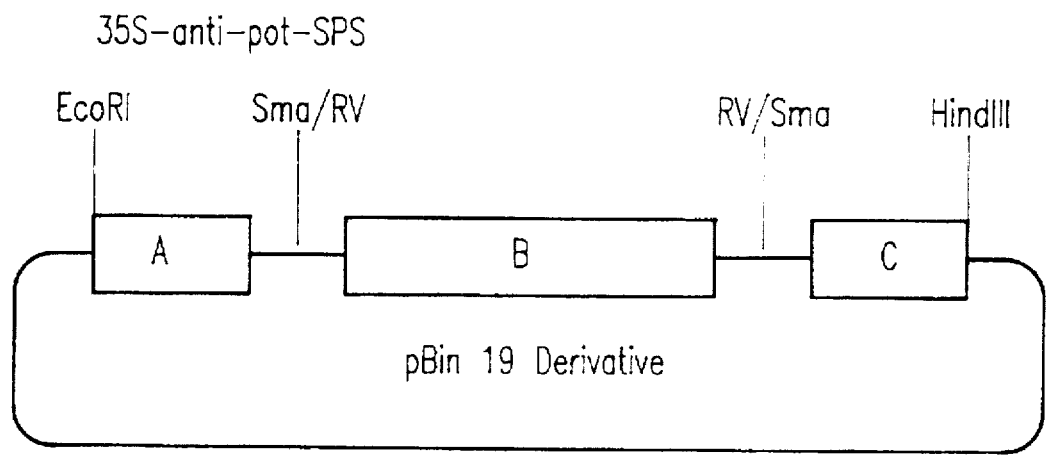
FIG. 1 provides the structure of the 35S-anti-pot-SPS gene.

The coding sequence contains the information for the formation of an mRNA for the sucrose-phosphate-synthase (SPS) or for the formation of an anti-sense RNA for the SPS. Whether the translatable mRNA or an anti-sense RNA is formed depends on the orientation of the coding sequence in relation to the promoter. If the 3' end of the coding sequence is fused to the 3' end of the promoter, an anti-sense RNA results, while the fusion of the 5' end of the coding sequence to the 3' end of the promoter, a translatable RNA results. This latter leads to an increase of the SPS activity in the cell, while the first leads to a reduction of the SPS activity in the cell. Such a reduction of SPS activity is especially significant in view of the undesirable formation of sucrose and/or reducing sugars as a result of cold storage of harvested organs.

The coding sequence for SPS can be one of the three described above or one that is derived by modifications of the sequences described above. A derivation can be carried out, e.g. by current methods of mutagenesis and/or recombination. In particular, changes of SPS sequences that lead to a neutralisation of the plant's own regulation mechanism are contemplated.

The DNA sequences of the invention can also be used for the preparation of derivatives whose gene products are not subjected to the plant's own activity regulation during a phosphorylation reaction.

Further, the sequences can also be used for the preparation of derivatives by targeted and non-targeted mutagenesis.

The invention relates further to derivatives of the DNA sequences of the invention that are obtained by exchange of single bases or by deletion or insertion of base sequences and which code for proteins with a comparable activity to sucrose-phosphate-synthase.

The 5' untranslated area of the sequence, Seq. ID No 1, is not part of SPS, but is shown as a cloning artefact. The methionine start codon of the coding region lies in a region in which there is no homology of the amino acid sequence to the other SPS sequences. Since this sequence does not also fully coincide in the homologous region with one of the other sequences, it is recognisable that the sequence Seq. ID No. 1 is not a derivative of the sequences Seq. ID No. 3 and Seq. ID No. 5.

The termination sequence provides the correct finishing of the transcription and the attachment of a polyadenyl group to the RNA. This polyadenyl group has an important function in the stabilisation of RNA molecules in the cells. With suitable plasmids which contain the DNA sequences of the invention, plants can be transformed with the object of raising and/or reducing the SPS activity and/or modifying of the sucrose concentration.

Plasmids that can be used include e.g. p35S-anti-pot-SPS (DSM 7125) and pB33-anti-pot-SPS (DSM 7124). With the gene 35S-anti-pot-SPS, located on the plasmid p35S-anti-pot-SPS, the concentration of the mRNA for the SPS protein and the enzymatic activity, for example, can be reduced. With the gene B33S-anti-pot-SPS, located on the plasmid pB33-anti-pot-SPS, the concentration of the mRNA for the SPS protein and the enzymatic activity, specifically for potato tubers for example, can be reduced. In a similar way to the SPS sequence (Seq. ID No. 1) located on this plasmid, other SPS sequences, e.g. the sequences Seq. ID No. 3 and Seq. ID No. 5 also be cloned in suitable vectors and for the same purpose.

In the plant, the SPS is subjected to an activity control by phosphorylation. This allows the plant to regulate the activity of the enzyme within a fixed frame independent of the amount of the SPS protein. If one of the changes occurring outside the activity of the SPS is to achieved, it is necessary to evade the plant's own regulation mechanism. Therefore changing the phosphorylation possibilities is an important target for influencing the SPS activity and thus the sucrose content of the plant.

It is not known in which position in the SPS protein, target directed changes of the coding regions can be achieved which serve the purpose of introducing in the plant SPS activity which is not subject to any of the plant's own controls.

The DNA sequence described here, which contains the coding region for SPS from *Solanum tuberosum*, allows the identification of the sites of protein phosphorylation of the SPS. By using standard methods (Sambrook, J., Fritsch, E. F., Maniatis, T. (1989) Molecular Cloning: A laboratory Manual, 2nd. Edn., Cold Spring Harbor Laboratory Press, N.Y., USA), a localisation of the phosphorylation positions of SPS is possible using the DNA sequences of the invention. These being known, by use of the plasmids with the SPS sequence, a target directed mutagenesis (Sambrook et al, 1989) of the coding region of SPS and/or a non-target directed mutagenesis (Sambrook et al, 1989) and subsequent probing of the desired mutations of the coding region of the SPS can be undertaken. Derivatives of the coding region can be prepared with the help of this plasmid, whose derived proteins are not subjected to the plants own regulation mechanisms.

Since the SPS enzyme is regulated by phosphorylation in all tested species, except maize, one can refer to sequence comparisons to identify possible phosphorylation sites. The criterium for this is that a serine residue appears in an acidic medium in the regulated SPS protein, but not however with maize.

There are 12 such serine residues in the sequences, Seq. ID No. 3 and Seq ID No. 5. In the sequence Seq ID No. 1, the first of the 12 serine residues is missing, since the coding region begins just later. The sequence, Seq. ID No. 1 is thus especially suitable for the production of SPS activity in plants that is not liable to endogenous activity regulation.

For the introduction of the SPS sequence in higher plants, a large number of cloning vectors are available which contain a replication signal for *E. coli* and a marker, which allows for the selection of the transformed cells. Examples of vectors are pBR 322, pUC-series, M13 mp-series, pACYC 184; EMBL 3 etc. According to the introduction method of the desired gene in the plant, other DNA sequences may be suitable. Should the Ti- or Ri-plasmid be used, e.g. for the transformation of the plant cell, then at least the right boundary, often however both the right and left boundary of the Ti- and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System, Offsetdrukkerij Kanters B. V. Alblasserdam, (1985), Chapter V; Fraley, et al., Crit. Rev. Plant Sci., 4:1–46 and An et al. (1985) EMBO J. 4: 277–287. Once the introduced DNA is integrated in the genome, it is generally stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells which lack the introduced DNA.

For the introduction of DNA into a plant, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium which contains antibiotics or biocides for selection. The resulting plants can then be tested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al.(1986) Plant Cell Reports 5: 81–84). These plants can be grown normally and crossed with plants, that possess the same transformed genes or different genes. The resulting hybrid individuals have the corresponding phenotypical properties.

Deposits

The following plasmids were deposited at the Deutschen Sammlung. von Mikroorganismen (DSM) in Braunschweig, Germany on the 12.06.1992 (deposit number):
Plasmid p35S-anti-pot-SPS (DSM 7125)
Plasmid pB33-anti-pot-SPS (DSM 7124)

DESCRIPTION OF THE FIGURES

FIG. 1: Structure of the 35S-anti-pot-SPS gene
A=Fragment A: CaMV 35S promoter, nt 6909–7437 (Franck et al.,1980. Cell 21: 285–294)
B=Fragment B: sucrose phosphate synthase, EcoRV Fragment (nt 1 bis 2011), ca. 2000 bp, orientation: anti-sense
C=Fragment C: nt 11748–11939 of the T-DNA of the Ti-plasmid pTiACH5; Gielen et al., 1984, EMBO J 3: 835–846)

Figure 2:
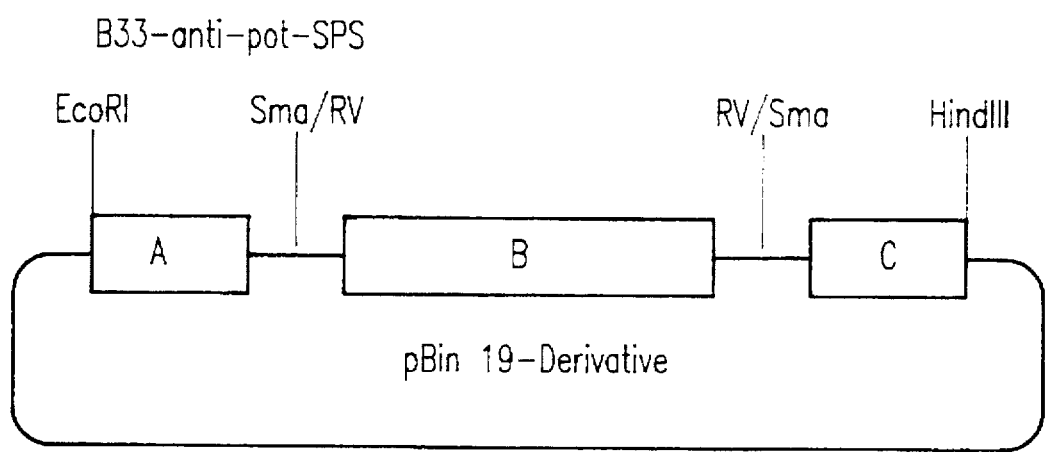
FIG. 2 provides the structure of the B33-anti-pot-SPS gene.

FIG. 2: Structure of the B33-anti-pot-SPS gene
A=Fragment A: B33 promoter of the patatin gene from S. tuberosum, (Rocha-Sosa et al., 1989, EMBO J 8: 23–29), ca 530 bp
B=Fragment B: sucrose phosphate synthase (s. FIG. 2), EcoRV fragment (nt 2011 bis 1), ca. 2000 bp, orientation: anti-sense
C=Fragment C: nt 11748–11939 of T-DNA of the Ti-plasmid pTiACH5 (Gielen et al., 1984, EMBO J 3: 835–846)

Figure 3:
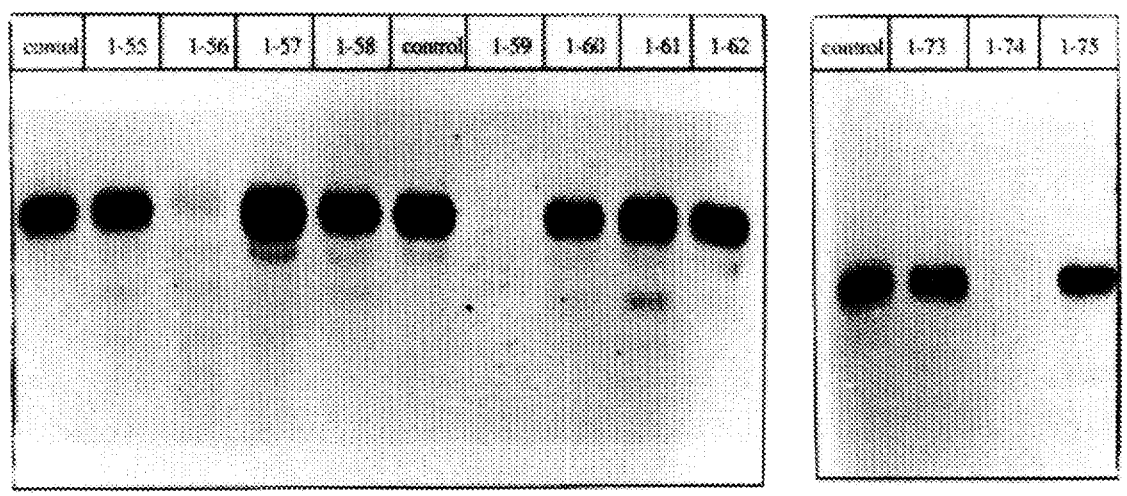
FIG. 3 provides an analysis of plants transformed with a plasmid which included the 35S-anti-pot-SPS gene.

FIG. 3: shows the results of the transformation of transgenic potato plants.
Control=wild type plants
1–75=individual transgenic plants FIG. 4: shows the results of the transformation of potato plants
Control=wild type plants
3–20=individual transgenic plants In order to understand the examples forming the basis of this invention all the processes necessary for these tests and which are known per se will first of all be listed:
1. Cloning Process The vectors pUC 18/19 and M13mp10 series (Yanisch-Perron et al. (1985) Gene 33: 103–119), as well as the vector EMBL 3 (Frischauf et al. (1983) J Mol Biol 170: 827–842) were used for cloning.

For the plant transformations, the gene constructs were cloned in the binary vector BIN 19 (Bevan (1984) Nucl. Acids Res 12: 8711–8720)
2. Bacterial strains The E. coli strain BMH71-18 (Messing et al., Proc. Natl. Acad. Sci. USA (1977), 24, 6342–6346) or TB1 was used for the pUC and M13 mP vectors.

For the vector BIN19, only the E. coli strain TB1 was used. TB1 is a recombinant-negative, tetracycline-resistant derivative of strain JM101 (Yanisch-Perron et al., Gene (1985), 33, 103–119). The genotype of the TB1 strain is (Bart Barrel, personal communication): F'(traD36, proAB, lacI, lacZΔM15), Δ(lac, pro), SupE, this, recA, Sr1::Tn10 (TcR).

The transformation of the plasmids into the potato plants was carried out using Agrobacterium tumefaciens strain LBA4404 (Bevan, (1984), Nucl. Acids Res. 12, 8711–8720).
3. Transformation of Aarobacterium tumefaciens In the case of BIN19 derivatives, the insertion of the DNA into the Agrobacterium was effected by direct transformation in accordance with the method of Holsters et al., (1978) (Mol Gene Genet 163: 181–187). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.
4. Plant transformation Ten small leaves, wounded with a scalpel, of a sterile potato culture were placed in 10 ml of MS medium with 2% sucrose containing 30–50 µl of an Agrobacterium tumefaciens overnight culture grown under selection. After 3–5 minutes gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.
5. SPS activity test The SPS activity was determined according to the method of Siegel and Stitt (1990, Plant Science 66: 205–210) in a two stage analysis. To 180 µl of a solution of 50 mM HEPES/KOH (pH 7.4), 5 mM magnesium chloride, 5 mM fructose-6-phosphate, 25 mM glucose-6-phosphate and 6 mM uridine-5'-diphosphoglucose 20 µl of probe was added and incubated for 10 minutes at 25° C. It was heated for 3 minutes at 95° C., to complete the reaction. After centrifuging, the supernatant was spectroscopically analysed for the liberation of uridine-5'-diphosphate, whereby a pyruvate-kinase coupling enzyme reaction was used. Preparations without hexose phosphate, as well as the measurement of the recovery of added uridine-5'-diphosphate act as controls.

EXAMPLES

Example 1

Cloning of genes of the sucrose-phosphate-synthase from potato

Poly-A+ RNA was isolated from large leaves of spinach plants as well as potato plants grown in the greenhouse. Resulting from the poly-A+ RNA, a cDNA library in the expression vector Lambda Zap II was laid out. 100,000 plaques of both libraries were separated from spinach using a rabbit antiserum directed against pure SPS protein in relation to immunologically cross reacting protein. (Sonnewald et al., 1992, in press). From the potato library, positively reacting clones were obtained. These clones were further purified by standard methods and, by in vivo excision, plasmids were obtained which carried a double stranded cDNA as an insertion. After testing the size of the insertions, individual clones were analysed by determining the primary sequence.

Example 2

Determination of the nucleotide sequence of the SPS from potato coding cDNA molecules and derivation of the corresponding amino acid sequences The nucleotide sequences of the insertions obtained from Example 1 were determined by standard methods by means of the dideoxy method (Sanger et al. (1977) Proc. Natl. Acad. Sci. USA, 74, 5463–5467). The nucleotide sequences (Seq. ID No. 1 to Seq. ID No. 3) are described above. The amino acid sequences derived therefrom are also given.

Example 3

Construct of the plasmid p35s-anti-pot-SPS and insertion of gene 35s-anti-pot-sps in the genome of potato plants The gene 35s-anti-pot-SPS consists of the three fragments A, B and C (see FIG. 1).

The plasmid was prepared as follows: From the pBluescript plasmid with the total insertion, an approximately 2 kb size fragment was prepared by EcoRV cleavage, and this was cloned in the SmaI cleavage site of the vector pBinAR (Höfgen & Willmitzer, 1990, Plant Sci., 66, 221–230). The vector pBinAR is a derivative of the binary vector BIN 19 (Bevan, 1984, Nucl. Acids Res. 12: 8711–8721) and was transferred using an Agrobacterium tumefaciens mediated transformation into potato. Intact, fertile plants were regenerated from the transformed cells.

As a result of the transformation, some transgenic potato plants were shown to have a reduced amount of RNA coding for the potato SPS (see FIG. 3). 50 µg total RNA in a Northern blot experiment was hybridised with the probe for SPS from potato.

Further the plants showed a reduction in SPS activity (see Table I).

Thus, by the transfer and expression of the gene 35s-anti-pot-SPS in potato plants, the amount of mRNA for the SPS protein which is formed, as well as the existing enzymatic activity can be significantly reduced.

Example 4

Figure 4:
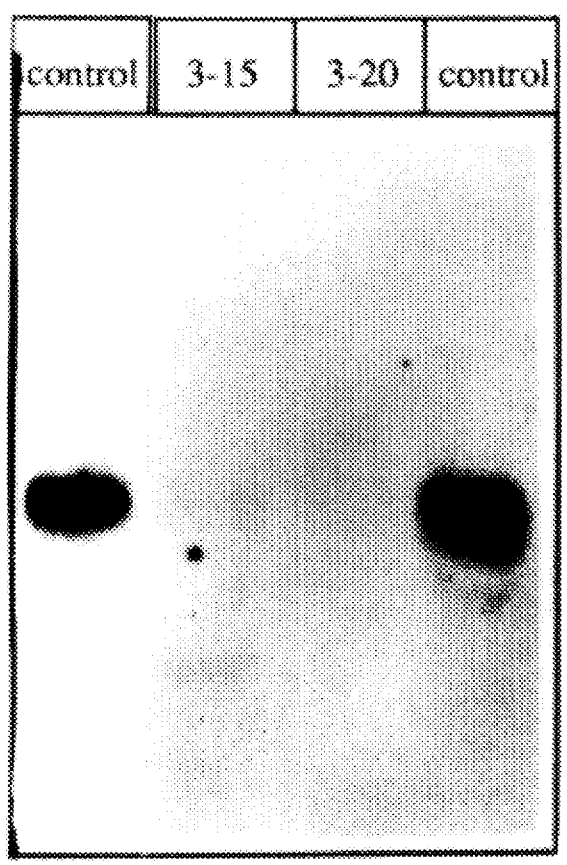
FIG. 4 is an analysis of plants transformed with a plasmid which included the B33-anti-pot-SPS gene.

Construct of plasmid pB33-anti-pot-SPS and insertion of gene B33-anti-pot-SPS in the renome of potato plants The gene B33-anti-pot-SPS consists of the three fragments A, B and C (see FIG. 4). The plasmid was prepared in an analogous method to that described in Example 3, except that a pBin 19 derivative was used as starting vector which contains the B33 promoter of the patatin gene from *Solanum tuberosum* (Rocha-Sosa et al., 1989, EMBO J. 8: 23–29) in place of the 35S promoter of pBinAR.

The gene B33-anti-pot-SPS was transferred into potato plants using an *Agrobacterium tumefaciens* mediated transformation. Intact, fertile plants were regenerated from the transformed cells.

As a result of the transformation, some transgenic potato plants were shown with a reduced amount of RNA coding for the potato SPS (see FIG. 4). 50 µg total RNA in a Northern blot experiment was hybridised with the probe for SPS from potato.

Further the plants also showed a reduction of the SPS activity only in the tubers.

Thus, by the transfer and expression of the gene 35s-anti-pot-SPS in potato plants, the amount of mRNA for the SPS protein which is formed, as well as the existing enzymatic activity can be significantly reduced.

TABLE I

Results of the transformation of potato plants

| 1 | 2 | 3 | 4 | 5 |
|---|---|---|---|---|
| Control | 26.1 | 3.6 | 13.8 | 100 |
| 1-55 | 11.8 | 2.7 | 22.9 | 45 |
| 1-57 | 20.4 | 5.9 | 28.9 | 78 |
| 1-59 | 3.8 | 1.4 | 36.8 | 14.6 |
| 1-67 | 3.8 | 1.7 | 44.7 | 14.6 |
| 1-69 | 17.2 | 2.0 | 11.7 | 67 |
| 1-72 | 14.6 | 1.9 | 13.0 | 56 |
| 1-74 | 5.1 | 1.7 | 33.3 | 19.5 |

Column 1: Control = Wild type plants, numbers indicate individual transgenic plants
Column 2: Maximal speed of the enzyme reaction in the SPS activity test in nmol/min/mg.
Column 3: Speed in the SPS activity test in nmol/min/mg.
Column 4: Activity level of the SPS in %.
Column 5: Residual activity of the SPS in %.

I claim:

1. A transgenic plant with an altered level of sucrose-phosphate-synthase activity relative to a nontransformed plant, wherein a chimeric DNA construct comprising a DNA fragment selected from the group consisting of the coding region of SEQ ID No. 1, the coding region of SEQ ID No. 3 and the coding region of SEQ ID No. 5 has been transformed into said plant.

2. A transgenic plant, as recited in claim 1, wherein said plant is a potato plant.

3. A transgenic plant with an altered level of sucrose-phosphate-synthase activity relative to a nontransformed plant, wherein a chimeric DNA construct comprising a DNA fragment encoding sucrose-phosphate-synthase which comprises an amino acid sequence selected from the group consisting of SEQ ID No. 2, SEQ ID No. 4 and SEQ ID No. 6 has been transformed into said plant.

4. A DNA fragment comprising the coding region of SEQ ID No. 1 which begins at nucleotide posistion 957.

5. A DNA fragment comprising the coding region of SEQ ID No. 3 which begins at nucleotide posistion 121.

6. A DNA fragment comprising the coding region of SEQ ID No. 5 which begins at nucleotide posistion 118.

7. A plasmid, comprising:

a) a promoter sequence;

b) at least one DNA fragment selected from the group consisting of the coding region of SEQ ID No. 1, the coding region of SEQ ID No. 3 and the coding region of SEQ ID No. 5, wherein said DNA fragment is operably linked to said promoter; and c) a non-coding termination sequence operably linked to said DNA fragment.

8. A plasmid, comprising:

a) a promoter sequence;

b) at least one DNA fragment encoding sucrose-phosphate-synthase wherein said sucrose-phosphate-synthase comprises an amino acid sequence selected from the group consisting of SEQ ID No. 2, SEQ ID No. 4 and SEQ ID No. 6, wherein said DNA fragment is operably linked to said promoter; and c) a non-coding termination sequence operably linked to said DNA fragment.

9. A method of producing a plant with an altered level of sucrose-phosphate-synthase activity relative to a nontransformed plant, comprising the step of:

overexpressing a DNA sequence according to claim 4 in a plant.

10. A method of producing a plant with an altered level of sucrose-phosphate-synthase activity relative to a nontransformed plant, comprising the step of:

overexpressing a DNA sequence according to claim 5 in a plant.

11. A method of producing a plant with an altered level of sucrose-phosphate-synthase activity relative to a nontransformed plant, comprising the step of:

overexpressing a DNA sequence according to claim 6 in a plant.

12. A method of producing a plant with an altered level of sucrose-phosphate-synthase activity relative to a nontransformed plant, comprising the steps of:

transforming a plant cell with a plasmid according to claim 7; and regenerating a plant from said transformed plant cell.

13. A method of producing a plant with an altered level of sucrose-phosphate-synthase activity relative to a nontransformed plant, comprising the steps of:

transforming a plant cell with a plasmid according to claim 8; and regenerating a plant from said transformed plant cell.

14. A DNA fragment encoding a sucrose-phosphate-synthase protein wherein said sucrose-phosphate-synthase comprises an amino acid sequence as shown in SEQ ID No. 2.

15. A DNA fragment encoding a sucrose-phosphate-synthase protein wherein said sucrose-phosphate-synthase comprises an amino acid sequence as shown in SEQ ID No. 4.

16. A DNA fragment encoding a sucrose-phosphate-synthase protein wherein said sucrose-phosphate-synthase comprises an amino acid sequence as shown in SEQ ID No. 6.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3740 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Solanum tuberosum ( i x ) FEATURE:
        ( A ) NAME/KEY: CDS
        ( B ) LOCATION: 957..3494
        ( D ) OTHER INFORMATION: /note= "Sucrose-Phosphate-Synthase"

( x i ) SEQUENCE DESCRIPTION: SEQ ID NO:1:

| | | | | | | |
|---|---|---|---|---|---|---|
| CTATTCTCTC | CCCTCCTTTT | TCTCCTCTCT | TCAACCCCAA | AACTTCCCTT | TCAAAGCCTT | 60 |
| TGCTTTCCCT | TTCTCACTTA | CCCAGATCAA | CTAAGCCAAT | TTGCTGTAGC | CTCAGAAAAC | 120 |
| AGCATTCCCA | GATTGAAAAA | GAATCTTTTT | CAGTACCCAA | AAGTTGGGTT | TCTCATGTCC | 180 |
| AGCAAGGATT | AGCTGCTCTA | GCTATTTCTT | TAGCCCTTAA | TTTTTGTCCA | GTTGTGTCTT | 240 |
| CTGATTCTGC | ATTGGCATCT | GAATTTGATG | TGTTAAATGA | AGGGCCACCA | AAGGACTCAT | 300 |
| ATGTAGTTGA | TGATGCTGGT | GTGCTTAGCA | GGGTGACAAA | GTCTGATTTG | AAGGCATTGT | 360 |
| TGTCTGATGT | GGAGAAGAGA | AAAGGCTTCC | ACATTAATTT | CATCACTGTC | CGCAAGCTCA | 420 |
| CTAGCAAAGC | TGATGCTTTT | GAGTATGCTG | ACCAAGTTTT | GGAGAAGTGG | TACCCTAGTG | 480 |

| | | |
|---|---|---|
| TTGAACAAGG AAATGATAAG GGTATAGTTG TGCTTGTTAC AAGTCAAAAG GAAGGCGCAA | | 540 |
| TAACCGGTGG CCCTGATTTT GTAAAGGCCG TTGGAGATAC TGTTCTTGAT GCTACCGTCT | | 600 |
| CAGAGAACCT TCCAGTGTTG GCTACTGAAG AGAAGTACAA TGAAGCAGTT TTCAGCACTG | | 660 |
| CCACACGTCT TGTTGCAGCC ATTGATGGCC TTCCTGATCC TGGTGGACCC CAACTCAAGG | | 720 |
| ATAACAAAAG AGAGTCCAAC TTCAAATCCA GAGAGGAAAC TGATGAGAAA AGAGGACAAT | | 780 |
| TCACACTTGT GGTTGGTGGG CTGTTAGTGA TTGCTTTTGT TGTTCCTATG GCTCAATACT | | 840 |
| ATGCATATGT TTCAAAGAAG TGAACTGTCT GATTCTGGAA AGTTACATTT TCGTGAGATT | | 900 |
| TGAGTAAGCA TGTATATTAT CGTGTACAAA ATGGTCCATT CGGAAATGAC TGATTC | | 956 |

```
ATG AGA TAT TTA AAA AGG ATA AAT ATG AAG ATT TGG ACC TCC CCT AAC       1004
Met Arg Tyr Leu Lys Arg Ile Asn Met Lys Ile Trp Thr Ser Pro Asn
 1           5                  10                  15

ATA ACG GAT ACT GCC ATT TCT TTT TCA GAG ATG CTG ACG CCA ATA AGT       1052
Ile Thr Asp Thr Ala Ile Ser Phe Ser Glu Met Leu Thr Pro Ile Ser
                20                  25                  30

ACA GAC GGC TTG ATG ACT GAG ATG GGG GAG AGT AGT GGT GCT TAT ATT       1100
Thr Asp Gly Leu Met Thr Glu Met Gly Glu Ser Ser Gly Ala Tyr Ile
            35                  40                  45

ATT CGC ATT CCT TTT GGA CCA AGA GAG AAA TAT ATT CCA AAA GAA CAG       1148
Ile Arg Ile Pro Phe Gly Pro Arg Glu Lys Tyr Ile Pro Lys Glu Gln
        50                  55                  60

CTA TGG CCC TAT ATT CCC GAA TTT GTT GAT GGT GCA CTT AAC CAT ATT       1196
Leu Trp Pro Tyr Ile Pro Glu Phe Val Asp Gly Ala Leu Asn His Ile
65                  70                  75                  80

ATT CAA ATG TCC AAA GTT CTT GGG GAG CAA ATT GGT AGT GGC TAT CCT       1244
Ile Gln Met Ser Lys Val Leu Gly Glu Gln Ile Gly Ser Gly Tyr Pro
                85                  90                  95

GTG TGG CCT GTT GCC ATA CAC GGA CAT TAT GCT GAT GCT GGC GAC TCA       1292
Val Trp Pro Val Ala Ile His Gly His Tyr Ala Asp Ala Gly Asp Ser
                100                 105                 110

GCT GCT CTC CTG TCA GGT GCT TTA AAT GTA CCA ATG CTT TTC ACT GGT       1340
Ala Ala Leu Leu Ser Gly Ala Leu Asn Val Pro Met Leu Phe Thr Gly
            115                 120                 125

CAC TCA CTT GGT AGA GAT AAG TTG GAG CAA CTG TTG CGA CAA GGT CGT       1388
His Ser Leu Gly Arg Asp Lys Leu Glu Gln Leu Leu Arg Gln Gly Arg
        130                 135                 140

TTG TCA AAG GAT GAA ATA AAC TCA ACC TAC AAG ATA ATG CGG AGA ATA       1436
Leu Ser Lys Asp Glu Ile Asn Ser Thr Tyr Lys Ile Met Arg Arg Ile
145                 150                 155                 160

GAG GCT GAA GAA TTA ACT CTT GAT GCT TCC GAA ATT GTC ATC ACT AGT       1484
Glu Ala Glu Glu Leu Thr Leu Asp Ala Ser Glu Ile Val Ile Thr Ser
                165                 170                 175

ACA AGA CAG GAG ATT GAC GAG CAA TGG CGT TTG TAT GAT GGG TTT GAT       1532
Thr Arg Gln Glu Ile Asp Glu Gln Trp Arg Leu Tyr Asp Gly Phe Asp
                180                 185                 190

CCA ATA TTA GAG CGT AAG TTA CGT GCA AGG ATC AAG CGC AAT GTC AGC       1580
Pro Ile Leu Glu Arg Lys Leu Arg Ala Arg Ile Lys Arg Asn Val Ser
            195                 200                 205

TGT TAT GGC AGG TTT ATG CCT CGT ATG GCT GTA ATT CCT CCT GGG ATG       1628
Cys Tyr Gly Arg Phe Met Pro Arg Met Ala Val Ile Pro Pro Gly Met
        210                 215                 220

GAG TTC CAC CAT ATT GTG CCA CAT GAA GGT GAC ATG GAT GGA GAA ACA       1676
Glu Phe His His Ile Val Pro His Glu Gly Asp Met Asp Gly Glu Thr
225                 230                 235                 240

GAA GGA AGT GAA GAT GGG AAG ACC CCG GAT CCA CCT ATT TGG GCA GAG       1724
Glu Gly Ser Glu Asp Gly Lys Thr Pro Asp Pro Pro Ile Trp Ala Glu
                245                 250                 255
```

| | | | | | | | | | | | | | | | | |
|---|---|---|---|---|---|---|---|---|---|---|---|---|---|---|---|---|
| ATT | ATG | CGC | TTC | TTT | TCT | AAT | CCA | AGG | AAG | CCT | ATG | ATA | CTC | GCA | CTT | 1772 |
| Ile | Met | Arg | Phe | Phe | Ser | Asn | Pro | Arg | Lys | Pro | Met | Ile | Leu | Ala | Leu | |
| | | | 260 | | | | 265 | | | | 270 | | | | | |
| GCT | AGG | CCT | GAT | CCC | AAG | AAG | AAC | CTC | ACT | ACT | TTA | GTG | AAA | GCA | TTT | 1820 |
| Ala | Arg | Pro | Asp | Pro | Lys | Lys | Asn | Leu | Thr | Thr | Leu | Val | Lys | Ala | Phe | |
| | | 275 | | | | 280 | | | | | 285 | | | | | |
| GGT | GAA | TGT | CGT | CCA | TTG | AGA | GAG | CTT | GCT | AAT | CTT | ACT | TTG | ATA | ATG | 1868 |
| Gly | Glu | Cys | Arg | Pro | Leu | Arg | Glu | Leu | Ala | Asn | Leu | Thr | Leu | Ile | Met | |
| | 290 | | | | | 295 | | | | | 300 | | | | | |
| GGT | AAT | CGA | GAT | AAT | ATC | GAC | GAA | ATG | TCT | AGC | ACC | AAT | TCT | GCA | CTT | 1916 |
| Gly | Asn | Arg | Asp | Asn | Ile | Asp | Glu | Met | Ser | Ser | Thr | Asn | Ser | Ala | Leu | |
| 305 | | | | 310 | | | | 315 | | | | | | | 320 | |
| CTT | CTT | TCA | ATC | TTG | AAA | ATG | ATA | GAT | AAG | TAT | GAT | CTT | TAT | GGT | CAA | 1964 |
| Leu | Leu | Ser | Ile | Leu | Lys | Met | Ile | Asp | Lys | Tyr | Asp | Leu | Tyr | Gly | Gln | |
| | | | | 325 | | | | 330 | | | | | | 335 | | |
| GTA | GCT | TAT | CCT | AAA | CAC | CAC | AAG | CAG | TCA | GAT | GTT | CCT | GAT | ATC | TAC | 2012 |
| Val | Ala | Tyr | Pro | Lys | His | His | Lys | Gln | Ser | Asp | Val | Pro | Asp | Ile | Tyr | |
| | | | 340 | | | | 345 | | | | | 350 | | | | |
| CGT | CTT | GCT | GCA | AAG | ACT | AAG | GGT | GTT | TTT | ATT | AAT | CCA | GCT | TTT | ATT | 2060 |
| Arg | Leu | Ala | Ala | Lys | Thr | Lys | Gly | Val | Phe | Ile | Asn | Pro | Ala | Phe | Ile | |
| | | 355 | | | | | 360 | | | | | 365 | | | | |
| GAG | CCT | TTT | GGA | CTG | ACT | TTG | ATT | GAG | GCA | GCA | GCT | TAT | GGT | CTC | CCA | 2108 |
| Glu | Pro | Phe | Gly | Leu | Thr | Leu | Ile | Glu | Ala | Ala | Ala | Tyr | Gly | Leu | Pro | |
| | 370 | | | | | 375 | | | | | 380 | | | | | |
| ATG | GTA | GCC | ACA | AAA | AAT | GGA | GGA | CCT | GTT | GAT | ATA | CAT | AGG | GTT | CTT | 2156 |
| Met | Val | Ala | Thr | Lys | Asn | Gly | Gly | Pro | Val | Asp | Ile | His | Arg | Val | Leu | |
| 385 | | | | | 390 | | | | | 395 | | | | | 400 | |
| GAC | AAT | GGT | CTC | TTA | GTG | GAT | CCC | CAT | GAT | CAG | CAG | GCA | ATT | GCT | GAT | 2204 |
| Asp | Asn | Gly | Leu | Leu | Val | Asp | Pro | His | Asp | Gln | Gln | Ala | Ile | Ala | Asp | |
| | | | | 405 | | | | | 410 | | | | | 415 | | |
| GCT | CTT | TTG | AAG | TTG | GTT | GCT | GAT | AAG | CAA | CTG | TGG | GCT | AAA | TGC | AGG | 2252 |
| Ala | Leu | Leu | Lys | Leu | Val | Ala | Asp | Lys | Gln | Leu | Trp | Ala | Lys | Cys | Arg | |
| | | | 420 | | | | | 425 | | | | | 430 | | | |
| GCA | AAT | GGA | TTA | AAA | AAT | ATC | CAC | CTT | TTC | TCA | TGG | CCC | GAG | CAC | TGT | 2300 |
| Ala | Asn | Gly | Leu | Lys | Asn | Ile | His | Leu | Phe | Ser | Trp | Pro | Glu | His | Cys | |
| | | 435 | | | | | 440 | | | | | 445 | | | | |
| AAA | ACT | TAT | CTA | TCC | CGG | ATA | GCT | AGC | TGC | AAA | CCA | AGG | CAA | CCA | CGC | 2348 |
| Lys | Thr | Tyr | Leu | Ser | Arg | Ile | Ala | Ser | Cys | Lys | Pro | Arg | Gln | Pro | Arg | |
| | 450 | | | | | 455 | | | | | 460 | | | | | |
| TGG | CTG | AGA | TCC | ATT | GAT | GAT | GAT | GAT | GAA | AAT | TCA | GAA | ACA | GAT | TCA | 2396 |
| Trp | Leu | Arg | Ser | Ile | Asp | Asp | Asp | Asp | Glu | Asn | Ser | Glu | Thr | Asp | Ser | |
| 465 | | | | | 470 | | | | | 475 | | | | | 480 | |
| CCT | AGT | GAT | TCC | TTG | AGA | GAT | ATT | CAT | GAT | ATA | TCT | CTG | AAT | TTG | AGA | 2444 |
| Pro | Ser | Asp | Ser | Leu | Arg | Asp | Ile | His | Asp | Ile | Ser | Leu | Asn | Leu | Arg | |
| | | | | 485 | | | | | 490 | | | | | 495 | | |
| TTT | TCA | TTA | GAT | GGG | GAA | AAG | AAT | GAC | AAT | AAA | GAA | AAT | GCT | GAT | AAT | 2492 |
| Phe | Ser | Leu | Asp | Gly | Glu | Lys | Asn | Asp | Asn | Lys | Glu | Asn | Ala | Asp | Asn | |
| | | | 500 | | | | | 505 | | | | | 510 | | | |
| ACA | TTA | GAC | CCC | GAA | GTT | CGA | AGG | AGC | AAG | TTA | GAG | AAT | GCT | GTT | TTG | 2540 |
| Thr | Leu | Asp | Pro | Glu | Val | Arg | Arg | Ser | Lys | Leu | Glu | Asn | Ala | Val | Leu | |
| | | 515 | | | | | 520 | | | | | 525 | | | | |
| TCC | TTA | TCT | AAG | GGT | GCA | CTG | AAG | AGC | ACA | TCA | AAA | TCT | TGG | TCG | TCA | 2588 |
| Ser | Leu | Ser | Lys | Gly | Ala | Leu | Lys | Ser | Thr | Ser | Lys | Ser | Trp | Ser | Ser | |
| | 530 | | | | | 535 | | | | | 540 | | | | | |
| GAC | AAG | GCA | GAC | CAA | AAC | CCT | GGT | GCT | GGT | AAA | TTC | CCA | GCG | ATT | AGG | 2636 |
| Asp | Lys | Ala | Asp | Gln | Asn | Pro | Gly | Ala | Gly | Lys | Phe | Pro | Ala | Ile | Arg | |
| 545 | | | | | 550 | | | | | 555 | | | | | 560 | |
| AGG | AGG | CGA | CAT | ATT | TTT | GTT | ATT | GCA | GTG | GAT | TGT | GAT | GCT | AGC | TCA | 2684 |
| Arg | Arg | Arg | His | Ile | Phe | Val | Ile | Ala | Val | Asp | Cys | Asp | Ala | Ser | Ser | |
| | | | | 565 | | | | | 570 | | | | | 575 | | |

-continued

| | | | | | | | | | | | | | | | | |
|---|---|---|---|---|---|---|---|---|---|---|---|---|---|---|---|---|
| GGA | CTC | TCT | GGA | AGT | GTG | AAA | AAG | ATA | TTT | GAG | GCT | GTA | GAG | AAG | GAA | 2732 |
| Gly | Leu | Ser | Gly | Ser | Val | Lys | Lys | Ile | Phe | Glu | Ala | Val | Glu | Lys | Glu | |
| | | | | 580 | | | | 585 | | | | | 590 | | | |
| AGG | GCA | GAG | GGT | TCC | ATT | GGA | TTT | ATC | CTG | GCT | ACA | TCT | TTC | AAT | ATA | 2780 |
| Arg | Ala | Glu | Gly | Ser | Ile | Gly | Phe | Ile | Leu | Ala | Thr | Ser | Phe | Asn | Ile | |
| | | 595 | | | | | 600 | | | | | 605 | | | | |
| TCA | GAA | GTA | CAG | TCT | TTC | CTG | CTT | TCA | GAG | GGC | ATG | AAT | CCT | ACT | GAT | 2828 |
| Ser | Glu | Val | Gln | Ser | Phe | Leu | Leu | Ser | Glu | Gly | Met | Asn | Pro | Thr | Asp | |
| 610 | | | | | 615 | | | | | 620 | | | | | | |
| TTT | GAT | GCT | TAC | ATA | TGC | AAT | AGT | GGT | GGT | GAT | CTT | TAT | TAT | TCG | TCC | 2876 |
| Phe | Asp | Ala | Tyr | Ile | Cys | Asn | Ser | Gly | Gly | Asp | Leu | Tyr | Tyr | Ser | Ser | |
| 625 | | | | | 630 | | | | | 635 | | | | | 640 | |
| TTC | CAT | TCT | GAG | CAA | AAT | CCT | TTT | GTA | GTT | GAC | TTG | TAC | TAT | CAC | TCA | 2924 |
| Phe | His | Ser | Glu | Gln | Asn | Pro | Phe | Val | Val | Asp | Leu | Tyr | Tyr | His | Ser | |
| | | | | 645 | | | | | 650 | | | | | 655 | | |
| CAT | ATT | GAG | TAT | CGT | TGG | GGG | GGC | GAA | GGA | TTG | AGA | AAG | ACT | TTG | GTG | 2972 |
| His | Ile | Glu | Tyr | Arg | Trp | Gly | Gly | Glu | Gly | Leu | Arg | Lys | Thr | Leu | Val | |
| | | | 660 | | | | | 665 | | | | | 670 | | | |
| CGT | TGG | GCC | GCC | TCT | ATC | ATT | GAT | AAG | AAT | GGT | GAA | AAT | GGA | GAT | CAC | 3020 |
| Arg | Trp | Ala | Ala | Ser | Ile | Ile | Asp | Lys | Asn | Gly | Glu | Asn | Gly | Asp | His | |
| | | 675 | | | | | 680 | | | | | 685 | | | | |
| ATT | GTT | GTT | GAG | GAT | GAA | GAC | AAT | TCA | GCT | GAC | TAC | TGC | TAT | ACT | TTC | 3068 |
| Ile | Val | Val | Glu | Asp | Glu | Asp | Asn | Ser | Ala | Asp | Tyr | Cys | Tyr | Thr | Phe | |
| | 690 | | | | | 695 | | | | | 700 | | | | | |
| AAA | GTC | TGC | AAG | CCT | GGG | ACG | GTT | CCT | CCA | TCT | AAA | GAG | CTT | AGA | AAA | 3116 |
| Lys | Val | Cys | Lys | Pro | Gly | Thr | Val | Pro | Pro | Ser | Lys | Glu | Leu | Arg | Lys | |
| 705 | | | | | 710 | | | | | 715 | | | | | 720 | |
| GTA | ATG | CGA | ATT | CAG | GCA | CTT | CGT | TGT | CAC | GCT | GTT | TAT | TGT | CAA | AAT | 3164 |
| Val | Met | Arg | Ile | Gln | Ala | Leu | Arg | Cys | His | Ala | Val | Tyr | Cys | Gln | Asn | |
| | | | | 725 | | | | | 730 | | | | | 735 | | |
| GGG | AGT | AGG | ATT | AAT | GTG | ATC | CCT | GTA | CTG | GCA | TCT | CGG | TCC | CAA | GCA | 3212 |
| Gly | Ser | Arg | Ile | Asn | Val | Ile | Pro | Val | Leu | Ala | Ser | Arg | Ser | Gln | Ala | |
| | | | 740 | | | | | 745 | | | | | 750 | | | |
| CTC | AGG | TAC | TTA | TAT | CTG | CGA | TGG | GGA | ATG | GAC | TTG | TCG | AAG | TTG | GTG | 3260 |
| Leu | Arg | Tyr | Leu | Tyr | Leu | Arg | Trp | Gly | Met | Asp | Leu | Ser | Lys | Leu | Val | |
| | | 755 | | | | | 760 | | | | | 765 | | | | |
| GTT | TTC | GTC | GGA | GAA | AGT | GGT | GAT | ACC | GAT | TAT | GAA | GGA | TTA | ATC | GGT | 3308 |
| Val | Phe | Val | Gly | Glu | Ser | Gly | Asp | Thr | Asp | Tyr | Glu | Gly | Leu | Ile | Gly | |
| | 770 | | | | | 775 | | | | | 780 | | | | | |
| GGT | CTA | CGC | AAG | GCT | GTC | ATA | ATG | AAA | GGC | CTC | TGC | ACT | AAT | GCA | AGC | 3356 |
| Gly | Leu | Arg | Lys | Ala | Val | Ile | Met | Lys | Gly | Leu | Cys | Thr | Asn | Ala | Ser | |
| 785 | | | | | 790 | | | | | 795 | | | | | 800 | |
| AGC | TTA | ATT | CAC | GGT | AAT | AGG | AAT | TAC | CCG | CTA | TCT | GAT | GTT | TTA | CCA | 3404 |
| Ser | Leu | Ile | His | Gly | Asn | Arg | Asn | Tyr | Pro | Leu | Ser | Asp | Val | Leu | Pro | |
| | | | | 805 | | | | | 810 | | | | | 815 | | |
| TTC | GAC | AGC | CCT | AAT | GTC | ATC | CAA | GCG | GAC | GAG | GAA | TGT | AGC | AGC | ACC | 3452 |
| Phe | Asp | Ser | Pro | Asn | Val | Ile | Gln | Ala | Asp | Glu | Glu | Cys | Ser | Ser | Thr | |
| | | | 820 | | | | | 825 | | | | | 830 | | | |
| GAA | ATC | CGT | TGC | TTA | CTG | GTG | AAA | CTA | GCG | GTA | CTC | AAA | GGA | | | 3494 |
| Glu | Ile | Arg | Cys | Leu | Leu | Val | Lys | Leu | Ala | Val | Leu | Lys | Gly | | | |
| | | 835 | | | | | 840 | | | | | 845 | | | | |

TAATACCCTT CCCCCTTTGA TTGTCAAAAA CCTATATGAG CTATAAGACT ATGCCATGAA 3554

AAGAATGGCC ATCCATTTGG CTTGTCTTTT GAAGCTGTTA ATACTTTTCA ACAGACTACA 3614

AAATGAGATG AGTCCTTTGA TCCTCTTTAA AGGACATAAA AGCTTTATGC AAGAACCAGT 3674

GCTGTAAAGT TATAGAATTT CTTTTGCTAT ATATGACATT CGACAGAACC TGTTCCGGTT 3734

CATCGA 3740

( 2 ) INFORMATION FOR SEQ ID NO:2:

( i ) SEQUENCE CHARACTERISTICS:
   ( A ) LENGTH: 846 amino acids
   ( B ) TYPE: amino acid
   ( D ) TOPOLOGY: linear ( i i ) MOLECULE TYPE: protein ( x i ) SEQUENCE DESCRIPTION: SEQ ID NO:2:

```
Met Arg Tyr Leu Lys Arg Ile Asn Met Lys Ile Trp Thr Ser Pro Asn
 1               5                   10                  15

Ile Thr Asp Thr Ala Ile Ser Phe Ser Glu Met Leu Thr Pro Ile Ser
             20                  25                  30

Thr Asp Gly Leu Met Thr Glu Met Gly Glu Ser Ser Gly Ala Tyr Ile
         35                  40                  45

Ile Arg Ile Pro Phe Gly Pro Arg Glu Lys Tyr Ile Pro Lys Glu Gln
     50                  55                  60

Leu Trp Pro Tyr Ile Pro Glu Phe Val Asp Gly Ala Leu Asn His Ile
 65                  70                  75                  80

Ile Gln Met Ser Lys Val Leu Gly Glu Gln Ile Gly Ser Gly Tyr Pro
                 85                  90                  95

Val Trp Pro Val Ala Ile His Gly His Tyr Ala Asp Ala Gly Asp Ser
            100                 105                 110

Ala Ala Leu Leu Ser Gly Ala Leu Asn Val Pro Met Leu Phe Thr Gly
            115                 120                 125

His Ser Leu Gly Arg Asp Lys Leu Glu Gln Leu Leu Arg Gln Gly Arg
        130                 135                 140

Leu Ser Lys Asp Glu Ile Asn Ser Thr Tyr Lys Ile Met Arg Arg Ile
145                 150                 155                 160

Glu Ala Glu Glu Leu Thr Leu Asp Ala Ser Glu Ile Val Ile Thr Ser
                165                 170                 175

Thr Arg Gln Glu Ile Asp Glu Gln Trp Arg Leu Tyr Asp Gly Phe Asp
            180                 185                 190

Pro Ile Leu Glu Arg Lys Leu Arg Ala Arg Ile Lys Arg Asn Val Ser
        195                 200                 205

Cys Tyr Gly Arg Phe Met Pro Arg Met Ala Val Ile Pro Pro Gly Met
210                 215                 220

Glu Phe His His Ile Val Pro His Glu Gly Asp Met Asp Gly Glu Thr
225                 230                 235                 240

Glu Gly Ser Glu Asp Gly Lys Thr Pro Asp Pro Ile Trp Ala Glu
                245                 250                 255

Ile Met Arg Phe Phe Ser Asn Pro Arg Lys Pro Met Ile Leu Ala Leu
            260                 265                 270

Ala Arg Pro Asp Pro Lys Lys Asn Leu Thr Thr Leu Val Lys Ala Phe
        275                 280                 285

Gly Glu Cys Arg Pro Leu Arg Glu Leu Ala Asn Leu Thr Leu Ile Met
290                 295                 300

Gly Asn Arg Asp Asn Ile Asp Glu Met Ser Ser Thr Asn Ser Ala Leu
305                 310                 315                 320

Leu Leu Ser Ile Leu Lys Met Ile Asp Lys Tyr Asp Leu Tyr Gly Gln
                325                 330                 335

Val Ala Tyr Pro Lys His His Lys Gln Ser Asp Val Pro Asp Ile Tyr
            340                 345                 350

Arg Leu Ala Ala Lys Thr Lys Gly Val Phe Ile Asn Pro Ala Phe Ile
        355                 360                 365

Glu Pro Phe Gly Leu Thr Leu Ile Glu Ala Ala Ala Tyr Gly Leu Pro
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 370 |     |     |     | 375 |     |     |     | 380 |     |     |
| Met 385 | Val | Ala | Thr | Lys | Asn 390 | Gly | Gly | Pro | Val | Asp 395 | Ile | His | Arg | Val | Leu 400 |
| Asp | Asn | Gly | Leu | Leu 405 | Val | Asp | Pro | His | Asp 410 | Gln | Gln | Ala | Ile | Ala 415 | Asp |
| Ala | Leu | Leu | Lys 420 | Leu | Val | Ala | Asp | Lys 425 | Gln | Leu | Trp | Ala | Lys 430 | Cys | Arg |
| Ala | Asn | Gly 435 | Leu | Lys | Asn | Ile | His 440 | Leu | Phe | Ser | Trp | Pro 445 | Glu | His | Cys |
| Lys | Thr 450 | Tyr | Leu | Ser | Arg | Ile 455 | Ala | Ser | Cys | Lys | Pro 460 | Arg | Gln | Pro | Arg |
| Trp 465 | Leu | Arg | Ser | Ile | Asp 470 | Asp | Asp | Glu | Asn | Ser 475 | Glu | Thr | Asp | Ser 480 |
| Pro | Ser | Asp | Ser | Leu 485 | Arg | Asp | Ile | His | Asp 490 | Ile | Ser | Leu | Asn | Leu 495 | Arg |
| Phe | Ser | Leu | Asp 500 | Gly | Glu | Lys | Asn | Asp 505 | Asn | Lys | Glu | Asn | Ala 510 | Asp | Asn |
| Thr | Leu | Asp 515 | Pro | Glu | Val | Arg | Arg 520 | Ser | Lys | Leu | Glu | Asn 525 | Ala | Val | Leu |
| Ser | Leu 530 | Ser | Lys | Gly | Ala | Leu 535 | Lys | Ser | Thr | Ser | Lys 540 | Ser | Trp | Ser | Ser |
| Asp 545 | Lys | Ala | Asp | Gln | Asn 550 | Pro | Gly | Ala | Gly | Lys 555 | Phe | Pro | Ala | Ile | Arg 560 |
| Arg | Arg | Arg | His | Ile 565 | Phe | Val | Ile | Ala | Val 570 | Asp | Cys | Asp | Ala | Ser 575 | Ser |
| Gly | Leu | Ser | Gly 580 | Ser | Val | Lys | Lys | Ile 585 | Phe | Glu | Ala | Val | Glu 590 | Lys | Glu |
| Arg | Ala | Glu 595 | Gly | Ser | Ile | Gly | Phe 600 | Ile | Leu | Ala | Thr | Ser 605 | Phe | Asn | Ile |
| Ser | Glu 610 | Val | Gln | Ser | Phe | Leu 615 | Leu | Ser | Glu | Gly | Met 620 | Asn | Pro | Thr | Asp |
| Phe 625 | Asp | Ala | Tyr | Ile | Cys 630 | Asn | Ser | Gly | Gly | Asp 635 | Leu | Tyr | Tyr | Ser | Ser 640 |
| Phe | His | Ser | Glu | Gln 645 | Asn | Pro | Phe | Val | Val 650 | Asp | Leu | Tyr | Tyr | His 655 | Ser |
| His | Ile | Glu | Tyr 660 | Arg | Trp | Gly | Gly | Glu 665 | Gly | Leu | Arg | Lys | Thr 670 | Leu | Val |
| Arg | Trp | Ala 675 | Ala | Ser | Ile | Ile | Asp 680 | Lys | Asn | Gly | Glu | Asn 685 | Gly | Asp | His |
| Ile | Val 690 | Val | Glu | Asp | Glu | Asp 695 | Asn | Ser | Ala | Asp | Tyr 700 | Cys | Tyr | Thr | Phe |
| Lys 705 | Val | Cys | Lys | Pro | Gly 710 | Thr | Val | Pro | Pro | Ser 715 | Lys | Glu | Leu | Arg | Lys 720 |
| Val | Met | Arg | Ile | Gln 725 | Ala | Leu | Arg | Cys | His 730 | Ala | Val | Tyr | Cys | Gln 735 | Asn |
| Gly | Ser | Arg | Ile 740 | Asn | Val | Ile | Pro | Val 745 | Leu | Ala | Ser | Arg | Ser 750 | Gln | Ala |
| Leu | Arg | Tyr 755 | Leu | Tyr | Leu | Arg | Trp 760 | Gly | Met | Asp | Leu | Ser 765 | Lys | Leu | Val |
| Val | Phe 770 | Val | Gly | Glu | Ser | Gly 775 | Asp | Thr | Asp | Tyr | Glu 780 | Gly | Leu | Ile | Gly |
| Gly 785 | Leu | Arg | Lys | Ala | Val 790 | Ile | Met | Lys | Gly | Leu 795 | Cys | Thr | Asn | Ala | Ser 800 |

```
Ser  Leu  Ile  His  Gly  Asn  Arg  Asn  Tyr  Pro  Leu  Ser  Asp  Val  Leu  Pro
               805                     810                    815

Phe  Asp  Ser  Pro  Asn  Val  Ile  Gln  Ala  Asp  Glu  Glu  Cys  Ser  Ser  Thr
               820                     825                    830

Glu  Ile  Arg  Cys  Leu  Leu  Val  Lys  Leu  Ala  Val  Leu  Lys  Gly
               835                     840                    845
```

( 2 ) INFORMATION FOR SEQ ID NO:3:

( i ) SEQUENCE CHARACTERISTICS:
        ( A ) LENGTH: 3625 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Solanum tuberosum ( i x ) FEATURE:
        ( A ) NAME/KEY: CDS
        ( B ) LOCATION: 121..3282
        ( D ) OTHER INFORMATION: /note= "Sucrose-Phosphate-Synthase"

( x i ) SEQUENCE DESCRIPTION: SEQ ID NO:3:

```
ATTTTTTCT  CTAAGTTCTC  TCTCGCTGTC  CTTATCATTT  CACCACCTCC  ATAAATCTAG         60

AAACATCTTT  TCTACTCCGT  TAATCTCTCT  AGCACACGGC  GGAGGAGTGC  GGCGGAGGAG        120

ATG  GCG  GGA  AAC  GAT  TGG  ATT  AAC  AGT  TAC  TTA  GAG  GCG  ATA  CTG  GAT    168
Met  Ala  Gly  Asn  Asp  Trp  Ile  Asn  Ser  Tyr  Leu  Glu  Ala  Ile  Leu  Asp
  1                  5                        10                       15

GTT  GGA  CCA  GGG  CTA  GAT  GAT  AAG  AAG  TCA  TCG  TTG  TTG  TTG  AGA  GAA    216
Val  Gly  Pro  Gly  Leu  Asp  Asp  Lys  Lys  Ser  Ser  Leu  Leu  Leu  Arg  Glu
              20                        25                       30

AGA  GGG  AGG  TTT  AGT  CCG  ACG  AGG  TAC  TTT  GTT  GAG  GAA  GTT  ATT  ACT    264
Arg  Gly  Arg  Phe  Ser  Pro  Thr  Arg  Tyr  Phe  Val  Glu  Glu  Val  Ile  Thr
              35                        40                       45

GGA  TTC  GAT  GAG  ACT  GAT  TTG  CAT  CGT  TCG  TGG  ATC  CGA  GCA  CAA  GCT    312
Gly  Phe  Asp  Glu  Thr  Asp  Leu  His  Arg  Ser  Trp  Ile  Arg  Ala  Gln  Ala
         50                        55                       60

ACT  CGG  AGT  CCG  CAG  AGA  AGG  AAT  ACT  AGG  CTC  GAG  AAT  ATG  TGC  TGG    360
Thr  Arg  Ser  Pro  Gln  Arg  Arg  Asn  Thr  Arg  Leu  Glu  Asn  Met  Cys  Trp
 65                   70                       75                       80

AGG  ATT  TGG  AAT  TTG  GCT  CGC  CAG  AAA  AAG  CAG  CTT  GAG  GGA  GAG  CAA    408
Arg  Ile  Trp  Asn  Leu  Ala  Arg  Gln  Lys  Lys  Gln  Leu  Glu  Gly  Glu  Gln
              85                        90                       95

GCT  CAG  TGG  ATG  GCA  AAA  CGC  CGT  CAA  GAA  CGT  GAA  AGA  GGT  CGC  AGA    456
Ala  Gln  Trp  Met  Ala  Lys  Arg  Arg  Gln  Glu  Arg  Glu  Arg  Gly  Arg  Arg
             100                       105                      110

GAA  GCA  GTT  GCT  GAT  ATG  TCA  GAG  GAT  CTA  TCT  GAG  GGA  GAG  AAA  GGA    504
Glu  Ala  Val  Ala  Asp  Met  Ser  Glu  Asp  Leu  Ser  Glu  Gly  Glu  Lys  Gly
             115                       120                      125

GAT  ATA  GTC  GCT  GAC  ATG  TCA  TCT  CAT  GGT  GAA  AGT  ACC  AGA  GGC  CGA    552
Asp  Ile  Val  Ala  Asp  Met  Ser  Ser  His  Gly  Glu  Ser  Thr  Arg  Gly  Arg
             130                       135                      140

TTG  CCT  AGA  ATC  AGT  TCT  GTT  GAG  ACA  ATG  GAA  GCA  TGG  GTC  AGT  CAG    600
Leu  Pro  Arg  Ile  Ser  Ser  Val  Glu  Thr  Met  Glu  Ala  Trp  Val  Ser  Gln
145                       150                      155                      160

CAG  AGA  GGA  AAG  AAG  CTT  TAT  ATC  GTG  CTT  ATA  AGT  TTA  CAT  GGT  TTA    648
Gln  Arg  Gly  Lys  Lys  Leu  Tyr  Ile  Val  Leu  Ile  Ser  Leu  His  Gly  Leu
             165                       170                      175

ATT  CGG  GGT  GAG  AAT  ATG  GAG  CTT  GGA  CGG  GAT  TCT  GAT  ACT  GGT  GGT    696
Ile  Arg  Gly  Glu  Asn  Met  Glu  Leu  Gly  Arg  Asp  Ser  Asp  Thr  Gly  Gly
```

-continued

|     | 180 |     |     |     |     |     |     |     | 185 |     |     |     |     |     |     | 190 |     |     |      |
|-----|-----|-----|-----|-----|-----|-----|-----|-----|-----|-----|-----|-----|-----|-----|-----|-----|-----|-----|------|
| CAG | GTG | AAG | TAT | GTT | GTT | GAA | CTT | GCG | AGG | GCC | TTA | GGG | TCG | ATG | CCA |     |     |     | 744  |
| Gln | Val | Lys | Tyr | Val | Val | Glu | Leu | Ala | Arg | Ala | Leu | Gly | Ser | Met | Pro |     |     |     |      |
|     |     | 195 |     |     |     |     | 200 |     |     |     |     | 205 |     |     |     |     |     |     |      |
| GGT | GTA | TAT | CGG | GTT | GAC | TTG | CTT | ACT | AGA | CAA | GTA | TCT | TCA | CCA | GAA |     |     |     | 792  |
| Gly | Val | Tyr | Arg | Val | Asp | Leu | Leu | Thr | Arg | Gln | Val | Ser | Ser | Pro | Glu |     |     |     |      |
|     | 210 |     |     |     |     | 215 |     |     |     |     | 220 |     |     |     |     |     |     |     |      |
| GTA | GAT | TGG | AGC | TAT | GGT | GAG | CCG | ACA | GAG | ATG | CTG | ACG | CCA | ATA | AGT |     |     |     | 840  |
| Val | Asp | Trp | Ser | Tyr | Gly | Glu | Pro | Thr | Glu | Met | Leu | Thr | Pro | Ile | Ser |     |     |     |      |
| 225 |     |     |     | 230 |     |     |     |     | 235 |     |     |     |     | 240 |     |     |     |     |      |
| ACA | GAC | GGC | TTG | ATG | ACT | GAG | ATG | GGG | GAG | AGT | AGT | GGT | GCT | TAT | ATT |     |     |     | 888  |
| Thr | Asp | Gly | Leu | Met | Thr | Glu | Met | Gly | Glu | Ser | Ser | Gly | Ala | Tyr | Ile |     |     |     |      |
|     |     |     |     | 245 |     |     |     |     | 250 |     |     |     |     | 255 |     |     |     |     |      |
| ATT | CGC | ATT | CCT | TTT | GGA | CCA | AGA | GAG | AAA | TAT | ATT | CCA | AAA | GAA | CAG |     |     |     | 936  |
| Ile | Arg | Ile | Pro | Phe | Gly | Pro | Arg | Glu | Lys | Tyr | Ile | Pro | Lys | Glu | Gln |     |     |     |      |
|     |     |     | 260 |     |     |     |     | 265 |     |     |     |     | 270 |     |     |     |     |     |      |
| CTA | TGG | CCC | TAT | ATT | CCC | GAA | TTT | GTT | GAT | GGT | GCA | CTT | AAC | CAT | ATT |     |     |     | 984  |
| Leu | Trp | Pro | Tyr | Ile | Pro | Glu | Phe | Val | Asp | Gly | Ala | Leu | Asn | His | Ile |     |     |     |      |
|     |     | 275 |     |     |     |     | 280 |     |     |     |     | 285 |     |     |     |     |     |     |      |
| ATT | CAA | ATG | TCC | AAA | GTT | CTT | GGG | GAG | CAA | ATT | GGT | AGT | GGC | TAT | CCT |     |     |     | 1032 |
| Ile | Gln | Met | Ser | Lys | Val | Leu | Gly | Glu | Gln | Ile | Gly | Ser | Gly | Tyr | Pro |     |     |     |      |
|     | 290 |     |     |     |     | 295 |     |     |     |     | 300 |     |     |     |     |     |     |     |      |
| GTG | TGG | CCT | GTT | GCC | ATA | CAC | GGA | CAT | TAT | GCT | GAT | GCT | GGC | GAC | TCA |     |     |     | 1080 |
| Val | Trp | Pro | Val | Ala | Ile | His | Gly | His | Tyr | Ala | Asp | Ala | Gly | Asp | Ser |     |     |     |      |
| 305 |     |     |     |     | 310 |     |     |     |     | 315 |     |     |     |     | 320 |     |     |     |      |
| GCT | GCT | CTC | CTG | TCA | GGT | GCT | TTA | AAT | GTA | CCA | ATG | CTT | TTC | ACT | GGT |     |     |     | 1128 |
| Ala | Ala | Leu | Leu | Ser | Gly | Ala | Leu | Asn | Val | Pro | Met | Leu | Phe | Thr | Gly |     |     |     |      |
|     |     |     |     | 325 |     |     |     |     | 330 |     |     |     |     | 335 |     |     |     |     |      |
| CAC | TCA | CTT | GGT | AGA | GAT | AAG | TTG | GAG | CAA | CTG | TTG | GCA | CAA | GGT | CGA |     |     |     | 1176 |
| His | Ser | Leu | Gly | Arg | Asp | Lys | Leu | Glu | Gln | Leu | Leu | Ala | Gln | Gly | Arg |     |     |     |      |
|     |     |     | 340 |     |     |     |     | 345 |     |     |     |     | 350 |     |     |     |     |     |      |
| AAG | TCA | AAG | GAT | GAA | ATA | AAC | TCA | ACC | TAC | AAG | ATA | ATG | CGG | AGA | ATA |     |     |     | 1224 |
| Lys | Ser | Lys | Asp | Glu | Ile | Asn | Ser | Thr | Tyr | Lys | Ile | Met | Arg | Arg | Ile |     |     |     |      |
|     |     | 355 |     |     |     |     | 360 |     |     |     |     | 365 |     |     |     |     |     |     |      |
| GAG | GCT | GAA | GAA | TTA | ACT | CTT | GAT | GCT | TCC | GAA | ATT | GTC | ATC | ACT | AGT |     |     |     | 1272 |
| Glu | Ala | Glu | Glu | Leu | Thr | Leu | Asp | Ala | Ser | Glu | Ile | Val | Ile | Thr | Ser |     |     |     |      |
|     | 370 |     |     |     |     | 375 |     |     |     |     | 380 |     |     |     |     |     |     |     |      |
| ACA | AGA | CAG | GAG | ATT | GAC | GAG | CAA | TGG | CGT | TTG | TAT | GAT | GGG | TTT | GAT |     |     |     | 1320 |
| Thr | Arg | Gln | Glu | Ile | Asp | Glu | Gln | Trp | Arg | Leu | Tyr | Asp | Gly | Phe | Asp |     |     |     |      |
| 385 |     |     |     |     | 390 |     |     |     |     | 395 |     |     |     |     | 400 |     |     |     |      |
| CCA | ATA | TTA | GAG | CGT | AAG | TTA | CGT | GCA | AGG | ATC | AAG | CGC | AAT | GTC | AGC |     |     |     | 1368 |
| Pro | Ile | Leu | Glu | Arg | Lys | Leu | Arg | Ala | Arg | Ile | Lys | Arg | Asn | Val | Ser |     |     |     |      |
|     |     |     |     | 405 |     |     |     |     | 410 |     |     |     |     | 415 |     |     |     |     |      |
| TGT | TAT | GGC | AGG | TTT | ATG | CCT | CGT | ATG | GCT | GTA | ATT | CCT | CCT | GGG | ATG |     |     |     | 1416 |
| Cys | Tyr | Gly | Arg | Phe | Met | Pro | Arg | Met | Ala | Val | Ile | Pro | Pro | Gly | Met |     |     |     |      |
|     |     | 420 |     |     |     |     | 425 |     |     |     |     | 430 |     |     |     |     |     |     |      |
| GAG | TTC | CAC | CAT | ATT | GTG | CCA | CAT | GAA | GGT | GAC | ATG | GAT | GGT | GAA | ACA |     |     |     | 1464 |
| Glu | Phe | His | His | Ile | Val | Pro | His | Glu | Gly | Asp | Met | Asp | Gly | Glu | Thr |     |     |     |      |
|     |     | 435 |     |     |     |     | 440 |     |     |     |     | 445 |     |     |     |     |     |     |      |
| GAA | GGA | AGT | GAA | GAT | GGG | AAG | ACC | CCG | GAT | CCA | CCT | ATT | TGG | GCA | GAG |     |     |     | 1512 |
| Glu | Gly | Ser | Glu | Asp | Gly | Lys | Thr | Pro | Asp | Pro | Pro | Ile | Trp | Ala | Glu |     |     |     |      |
|     | 450 |     |     |     |     | 455 |     |     |     |     | 460 |     |     |     |     |     |     |     |      |
| ATT | ATG | CGC | TTC | TTT | TCT | AAT | CCA | AGG | AAG | CCT | ATG | ATA | CTC | GCA | CTT |     |     |     | 1560 |
| Ile | Met | Arg | Phe | Phe | Ser | Asn | Pro | Arg | Lys | Pro | Met | Ile | Leu | Ala | Leu |     |     |     |      |
| 465 |     |     |     |     | 470 |     |     |     |     | 475 |     |     |     |     | 480 |     |     |     |      |
| GCT | AGG | CCT | GAT | CCC | AAG | AAG | AAC | CTC | ACT | ACT | TTA | GTG | AAA | GCA | TTT |     |     |     | 1608 |
| Ala | Arg | Pro | Asp | Pro | Lys | Lys | Asn | Leu | Thr | Thr | Leu | Val | Lys | Ala | Phe |     |     |     |      |
|     |     |     |     | 485 |     |     |     |     | 490 |     |     |     |     | 495 |     |     |     |     |      |
| GGT | GAA | TGT | CGT | CCA | TTG | AGA | GAG | CTT | GCT | AAT | CTT | ACT | TTG | ATA | ATG |     |     |     | 1656 |
| Gly | Glu | Cys | Arg | Pro | Leu | Arg | Glu | Leu | Ala | Asn | Leu | Thr | Leu | Ile | Met |     |     |     |      |

-continued

|  |  |  | 500 |  |  |  |  | 505 |  |  |  |  | 510 |  |  |  |
|---|---|---|---|---|---|---|---|---|---|---|---|---|---|---|---|---|
| GGT | AAT | CGA | GAT | AAT | ATC | GAC | GAA | ATG | TCT | AGC | ACC | AAT | TCT | GCA | CTT | 1704 |
| Gly | Asn | Arg | Asp | Asn | Ile | Asp | Glu | Met | Ser | Ser | Thr | Asn | Ser | Ala | Leu |  |
|  |  | 515 |  |  |  |  | 520 |  |  |  |  | 525 |  |  |  |  |
| CTT | CTT | TCA | ATC | TTG | AAA | ATG | ATA | GAT | AAG | TAT | GAT | CTT | TAT | GGT | CAA | 1752 |
| Leu | Leu | Ser | Ile | Leu | Lys | Met | Ile | Asp | Lys | Tyr | Asp | Leu | Tyr | Gly | Gln |  |
|  | 530 |  |  |  |  | 535 |  |  |  |  | 540 |  |  |  |  |  |
| GTA | GCT | TAT | CCT | AAA | CAC | CAC | AAG | CAG | TCA | GAT | GTT | CCT | GAT | ATC | TAC | 1800 |
| Val | Ala | Tyr | Pro | Lys | His | His | Lys | Gln | Ser | Asp | Val | Pro | Asp | Ile | Tyr |  |
| 545 |  |  |  |  | 550 |  |  |  |  | 555 |  |  |  |  | 560 |  |
| CGT | CTT | GCT | GCA | AAG | ACT | AAG | GGT | GTT | TTT | ATT | AAT | CCA | GCT | TTT | ATT | 1848 |
| Arg | Leu | Ala | Ala | Lys | Thr | Lys | Gly | Val | Phe | Ile | Asn | Pro | Ala | Phe | Ile |  |
|  |  |  |  | 565 |  |  |  |  | 570 |  |  |  |  | 575 |  |  |
| GAG | CCT | TTT | GGA | CTG | ACT | TTG | ATT | GAG | GCA | GCA | GCT | TAT | GGT | CTC | CCA | 1896 |
| Glu | Pro | Phe | Gly | Leu | Thr | Leu | Ile | Glu | Ala | Ala | Ala | Tyr | Gly | Leu | Pro |  |
|  |  |  | 580 |  |  |  |  | 585 |  |  |  |  | 590 |  |  |  |
| ATG | GTA | GCC | ACA | AAA | AAT | GGA | GGA | CCT | GTT | GAT | ATA | CAT | AGG | GTT | CTT | 1944 |
| Met | Val | Ala | Thr | Lys | Asn | Gly | Gly | Pro | Val | Asp | Ile | His | Arg | Val | Leu |  |
|  |  | 595 |  |  |  |  | 600 |  |  |  |  | 605 |  |  |  |  |
| GAC | AAT | GGT | CTC | TTA | GTG | GAT | CCC | CAT | GAT | CAG | CAG | GCA | ATT | GCT | GAT | 1992 |
| Asp | Asn | Gly | Leu | Leu | Val | Asp | Pro | His | Asp | Gln | Gln | Ala | Ile | Ala | Asp |  |
|  | 610 |  |  |  |  | 615 |  |  |  |  | 620 |  |  |  |  |  |
| GCT | CTT | TTG | AAG | TTG | GTT | GCT | GAT | AAG | CAA | CTG | TGG | GCT | AAA | TGC | AGG | 2040 |
| Ala | Leu | Leu | Lys | Leu | Val | Ala | Asp | Lys | Gln | Leu | Trp | Ala | Lys | Cys | Arg |  |
| 625 |  |  |  |  | 630 |  |  |  |  | 635 |  |  |  |  | 640 |  |
| GCA | AAT | GGA | TTA | AAA | AAT | ATC | CAC | CTT | TTC | TCA | TGG | CCC | GAG | CAC | TGT | 2088 |
| Ala | Asn | Gly | Leu | Lys | Asn | Ile | His | Leu | Phe | Ser | Trp | Pro | Glu | His | Cys |  |
|  |  |  |  | 645 |  |  |  |  | 650 |  |  |  |  | 655 |  |  |
| AAA | ACT | TAT | CTA | TCC | CGG | ATA | GCT | AGC | TGC | AAA | CCA | AGG | CAA | CCA | CGC | 2136 |
| Lys | Thr | Tyr | Leu | Ser | Arg | Ile | Ala | Ser | Cys | Lys | Pro | Arg | Gln | Pro | Arg |  |
|  |  |  | 660 |  |  |  |  | 665 |  |  |  |  | 670 |  |  |  |
| TGG | CTG | AGA | TCC | ATT | GAT | GAT | GAT | GAT | GAA | AAT | TCA | GAA | ACA | GAT | TCA | 2184 |
| Trp | Leu | Arg | Ser | Ile | Asp | Asp | Asp | Asp | Glu | Asn | Ser | Glu | Thr | Asp | Ser |  |
|  |  | 675 |  |  |  |  | 680 |  |  |  |  | 685 |  |  |  |  |
| CCT | AGT | GAT | TCC | TTG | AGA | GAT | ATT | CAT | GAT | ATA | TCT | CTG | AAT | TTG | AGA | 2232 |
| Pro | Ser | Asp | Ser | Leu | Arg | Asp | Ile | His | Asp | Ile | Ser | Leu | Asn | Leu | Arg |  |
|  | 690 |  |  |  |  | 695 |  |  |  |  | 700 |  |  |  |  |  |
| TTT | TCA | TTA | GAT | GGG | GAA | AAG | AAT | GAC | AAT | AAA | GAA | AAT | GCT | GAT | AAT | 2280 |
| Phe | Ser | Leu | Asp | Gly | Glu | Lys | Asn | Asp | Asn | Lys | Glu | Asn | Ala | Asp | Asn |  |
| 705 |  |  |  |  | 710 |  |  |  |  | 715 |  |  |  |  | 720 |  |
| ACA | TTA | GAC | CCC | GAA | GTT | CGA | AGG | AGC | AAG | TTA | GAG | AAT | GCT | GTT | TTG | 2328 |
| Thr | Leu | Asp | Pro | Glu | Val | Arg | Arg | Ser | Lys | Leu | Glu | Asn | Ala | Val | Leu |  |
|  |  |  |  | 725 |  |  |  |  | 730 |  |  |  |  | 735 |  |  |
| TCC | TTA | TCT | AAG | GGT | GCA | CTG | AAG | AGC | ACA | TCA | AAA | TCT | TGG | TCG | TCA | 2376 |
| Ser | Leu | Ser | Lys | Gly | Ala | Leu | Lys | Ser | Thr | Ser | Lys | Ser | Trp | Ser | Ser |  |
|  |  |  | 740 |  |  |  |  | 745 |  |  |  |  | 750 |  |  |  |
| GAC | AAG | GCA | GAC | CAA | AAC | CCT | GGT | GCT | GGT | AAA | TTC | CCA | GCG | ATT | AGG | 2424 |
| Asp | Lys | Ala | Asp | Gln | Asn | Pro | Gly | Ala | Gly | Lys | Phe | Pro | Ala | Ile | Arg |  |
|  |  | 755 |  |  |  |  | 760 |  |  |  |  | 765 |  |  |  |  |
| AGG | AGG | CGA | CAT | ATT | TTT | GTT | ATT | GCA | GTG | GAT | TGT | GAT | GCT | AGC | TCA | 2472 |
| Arg | Arg | Arg | His | Ile | Phe | Val | Ile | Ala | Val | Asp | Cys | Asp | Ala | Ser | Ser |  |
|  | 770 |  |  |  |  | 775 |  |  |  |  | 780 |  |  |  |  |  |
| GGA | CTC | TCT | GGA | AGT | GTG | AAA | AAG | ATA | TTT | GAG | GCT | GTA | GAG | AAG | GAA | 2520 |
| Gly | Leu | Ser | Gly | Ser | Val | Lys | Lys | Ile | Phe | Glu | Ala | Val | Glu | Lys | Glu |  |
| 785 |  |  |  |  | 790 |  |  |  |  | 795 |  |  |  |  | 800 |  |
| AGG | GCA | GAG | GGT | TCC | ATT | GGA | TTT | ATC | CTG | GCT | ACA | TCT | TTC | AAT | ATA | 2568 |
| Arg | Ala | Glu | Gly | Ser | Ile | Gly | Phe | Ile | Leu | Ala | Thr | Ser | Phe | Asn | Ile |  |
|  |  |  |  | 805 |  |  |  |  | 810 |  |  |  |  | 815 |  |  |
| TCA | GAA | GTA | CAG | TCT | TTC | CTG | CTT | TCA | GAG | GGC | ATG | AAT | CCT | ACT | GAT | 2616 |
| Ser | Glu | Val | Gln | Ser | Phe | Leu | Leu | Ser | Glu | Gly | Met | Asn | Pro | Thr | Asp |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 820 |     |     |     |     | 825 |     |     |     |     | 830 |     |      |
| TTT | GAT | GCT | TAC | ATA | TGC | AAT | AGT | GGT | GGT | GAT | CTT | TAT | TAT | TCG | TCC | 2664 |
| Phe | Asp | Ala | Tyr | Ile | Cys | Asn | Ser | Gly | Gly | Asp | Leu | Tyr | Tyr | Ser | Ser |      |
|     |     | 835 |     |     |     |     | 840 |     |     |     |     | 845 |     |     |     |      |
| TTC | CAT | TCT | GAG | CAA | AAT | CCT | TTT | GTA | GTT | GAC | TTG | TAC | TAT | CAC | TCA | 2712 |
| Phe | His | Ser | Glu | Gln | Asn | Pro | Phe | Val | Val | Asp | Leu | Tyr | Tyr | His | Ser |      |
|     | 850 |     |     |     |     | 855 |     |     |     |     | 860 |     |     |     |     |      |
| CAT | ATT | GAG | TAT | CGT | TGG | GGG | GGC | GAA | GGA | TTG | AGA | AAG | ACT | TTG | GTG | 2760 |
| His | Ile | Glu | Tyr | Arg | Trp | Gly | Gly | Glu | Gly | Leu | Arg | Lys | Thr | Leu | Val |      |
| 865 |     |     |     |     | 870 |     |     |     |     | 875 |     |     |     |     | 880 |      |
| CGT | TGG | GCC | GCC | TCT | ATC | ATT | GAT | AAG | AAT | GGT | GAA | AAT | GGA | GAT | CAC | 2808 |
| Arg | Trp | Ala | Ala | Ser | Ile | Ile | Asp | Lys | Asn | Gly | Glu | Asn | Gly | Asp | His |      |
|     |     |     |     | 885 |     |     |     |     | 890 |     |     |     |     | 895 |     |      |
| ATT | GTT | GTT | GAG | GAT | GAA | GAC | AAT | TCA | GCT | GAC | TAC | TGC | TAT | ACT | TTC | 2856 |
| Ile | Val | Val | Glu | Asp | Glu | Asp | Asn | Ser | Ala | Asp | Tyr | Cys | Tyr | Thr | Phe |      |
|     |     |     | 900 |     |     |     |     | 905 |     |     |     |     | 910 |     |     |      |
| AAA | GTC | TGC | AAG | CCT | GGG | ACG | GTT | CCT | CCA | TCT | AAA | GAG | CTT | AGA | AAA | 2904 |
| Lys | Val | Cys | Lys | Pro | Gly | Thr | Val | Pro | Pro | Ser | Lys | Glu | Leu | Arg | Lys |      |
|     |     | 915 |     |     |     |     | 920 |     |     |     |     | 925 |     |     |     |      |
| GTA | ATG | CGA | ATT | CAG | GCA | CTT | CGT | TGT | CAC | GCT | GTT | TAT | TGT | CAA | AAT | 2952 |
| Val | Met | Arg | Ile | Gln | Ala | Leu | Arg | Cys | His | Ala | Val | Tyr | Cys | Gln | Asn |      |
|     | 930 |     |     |     |     | 935 |     |     |     |     | 940 |     |     |     |     |      |
| GGG | AGT | AGG | ATT | AAT | GTG | ATC | CCT | GTA | CTG | GCA | TCT | CGG | TCC | CAA | GCA | 3000 |
| Gly | Ser | Arg | Ile | Asn | Val | Ile | Pro | Val | Leu | Ala | Ser | Arg | Ser | Gln | Ala |      |
| 945 |     |     |     |     | 950 |     |     |     |     | 955 |     |     |     |     | 960 |      |
| CTC | AGG | TAC | TTA | TAT | CTG | CGA | TGG | GGA | ATG | GAC | TTG | TCG | AAG | TTG | GTG | 3048 |
| Leu | Arg | Tyr | Leu | Tyr | Leu | Arg | Trp | Gly | Met | Asp | Leu | Ser | Lys | Leu | Val |      |
|     |     |     |     | 965 |     |     |     |     | 970 |     |     |     |     | 975 |     |      |
| GTT | TTC | GTC | GGA | GAA | AGT | GGT | GAT | ACC | GAT | TAT | GAA | GGA | TTA | ATC | GGT | 3096 |
| Val | Phe | Val | Gly | Glu | Ser | Gly | Asp | Thr | Asp | Tyr | Glu | Gly | Leu | Ile | Gly |      |
|     |     |     | 980 |     |     |     |     | 985 |     |     |     |     | 990 |     |     |      |
| GGT | CTA | CGC | AAG | GCT | GTC | ATA | ATG | AAA | GGC | CTC | TGC | ACT | AAT | GCA | AGC | 3144 |
| Gly | Leu | Arg | Lys | Ala | Val | Ile | Met | Lys | Gly | Leu | Cys | Thr | Asn | Ala | Ser |      |
|     |     | 995 |     |     |     |     | 1000|     |     |     |     | 1005|     |     |     |      |
| AGC | TTA | ATT | CAC | GGT | AAT | AGG | AAT | TAC | CCG | CTA | TCT | GAT | GTT | TTA | CCA | 3192 |
| Ser | Leu | Ile | His | Gly | Asn | Arg | Asn | Tyr | Pro | Leu | Ser | Asp | Val | Leu | Pro |      |
|     | 1010|     |     |     |     | 1015|     |     |     |     | 1020|     |     |     |     |      |
| TTC | GAC | AGC | CCT | AAT | GTC | ATC | CAA | GCG | GAC | GAG | GAA | TGT | AGC | AGC | ACC | 3240 |
| Phe | Asp | Ser | Pro | Asn | Val | Ile | Gln | Ala | Asp | Glu | Glu | Cys | Ser | Ser | Thr |      |
| 1025|     |     |     |     | 1030|     |     |     |     | 1035|     |     |     |     | 1040|      |
| GAA | ATC | CGT | TGC | TTA | CTG | GAG | AAA | CTA | GCG | GTA | CTC | AAA | GGA |     |     | 3282 |
| Glu | Ile | Arg | Cys | Leu | Leu | Glu | Lys | Leu | Ala | Val | Leu | Lys | Gly |     |     |      |
|     |     |     |     | 1045|     |     |     |     | 1050|     |     |     |     |     |     |      |

```
TAATACCCTT CCCCCTTTGA TTGTCAAAAA CCTATATGAG CTATAAGACT ATGCCATGAA    3342

AAGAATGGCC ATCCATTTGG CTTGTCTTTT GAAGCTGTTA ATACTTTTCA ACAGACTACA    3402

AAATGAGATG AGTCCTTTGA TCCTCTTTAA AGGACATAAA AGCTTTATGC AAGAACCAGT    3462

GCTGTAAAGT TATAGAATTT CTTTTGCTAT ATATGACATT CGACAGAACC AGTTCCGGTT    3522

CATCGAGAAA AAGAAATAAA TTTCAACTTA TAAACATGCC TGATCATGTA AATTATCATA    3582

TACATCCATC GGAAGGCATT ATCGATGGGT TATCAGATTT TTT                      3625
```

( 2 ) INFORMATION FOR SEQ ID NO:4:

( i ) SEQUENCE CHARACTERISTICS:
( A ) LENGTH: 1054 amino acids
( B ) TYPE: amino acid
( D ) TOPOLOGY: linear ( i i ) MOLECULE TYPE: protein ( x i ) SEQUENCE DESCRIPTION: SEQ ID NO:4:

| Met | Ala | Gly | Asn | Asp | Trp | Ile | Asn | Ser | Tyr | Leu | Glu | Ala | Ile | Leu | Asp |
| 1 | | | | 5 | | | | | 10 | | | | | 15 | |

| Val | Gly | Pro | Gly | Leu | Asp | Asp | Lys | Lys | Ser | Ser | Leu | Leu | Leu | Arg | Glu |
| | | | 20 | | | | | 25 | | | | | 30 | | |

| Arg | Gly | Arg | Phe | Ser | Pro | Thr | Arg | Tyr | Phe | Val | Glu | Glu | Val | Ile | Thr |
| | | 35 | | | | | 40 | | | | | 45 | | | |

| Gly | Phe | Asp | Glu | Thr | Asp | Leu | His | Arg | Ser | Trp | Ile | Arg | Ala | Gln | Ala |
| | 50 | | | | | 55 | | | | | 60 | | | | |

| Thr | Arg | Ser | Pro | Gln | Arg | Arg | Asn | Thr | Arg | Leu | Glu | Asn | Met | Cys | Trp |
| 65 | | | | | 70 | | | | | 75 | | | | | 80 |

| Arg | Ile | Trp | Asn | Leu | Ala | Arg | Gln | Lys | Lys | Gln | Leu | Glu | Gly | Glu | Gln |
| | | | | 85 | | | | | 90 | | | | | 95 | |

| Ala | Gln | Trp | Met | Ala | Lys | Arg | Arg | Gln | Glu | Arg | Glu | Arg | Gly | Arg | Arg |
| | | | 100 | | | | | 105 | | | | | 110 | | |

| Glu | Ala | Val | Ala | Asp | Met | Ser | Glu | Asp | Leu | Ser | Glu | Gly | Glu | Lys | Gly |
| | | 115 | | | | | 120 | | | | | 125 | | | |

| Asp | Ile | Val | Ala | Asp | Met | Ser | Ser | His | Gly | Glu | Ser | Thr | Arg | Gly | Arg |
| | 130 | | | | | 135 | | | | | 140 | | | | |

| Leu | Pro | Arg | Ile | Ser | Ser | Val | Glu | Thr | Met | Glu | Ala | Trp | Val | Ser | Gln |
| 145 | | | | | 150 | | | | | 155 | | | | | 160 |

| Gln | Arg | Gly | Lys | Lys | Leu | Tyr | Ile | Val | Leu | Ile | Ser | Leu | His | Gly | Leu |
| | | | | 165 | | | | | 170 | | | | | 175 | |

| Ile | Arg | Gly | Glu | Asn | Met | Glu | Leu | Gly | Arg | Asp | Ser | Asp | Thr | Gly | Gly |
| | | | 180 | | | | | 185 | | | | | 190 | | |

| Gln | Val | Lys | Tyr | Val | Val | Glu | Leu | Ala | Arg | Ala | Leu | Gly | Ser | Met | Pro |
| | | 195 | | | | | 200 | | | | | 205 | | | |

| Gly | Val | Tyr | Arg | Val | Asp | Leu | Leu | Thr | Arg | Gln | Val | Ser | Ser | Pro | Glu |
| | 210 | | | | | 215 | | | | | 220 | | | | |

| Val | Asp | Trp | Ser | Tyr | Gly | Glu | Pro | Thr | Glu | Met | Leu | Thr | Pro | Ile | Ser |
| 225 | | | | | 230 | | | | | 235 | | | | | 240 |

| Thr | Asp | Gly | Leu | Met | Thr | Glu | Met | Gly | Glu | Ser | Ser | Gly | Ala | Tyr | Ile |
| | | | | 245 | | | | | 250 | | | | | 255 | |

| Ile | Arg | Ile | Pro | Phe | Gly | Pro | Arg | Glu | Lys | Tyr | Ile | Pro | Lys | Glu | Gln |
| | | | 260 | | | | | 265 | | | | | 270 | | |

| Leu | Trp | Pro | Tyr | Ile | Pro | Glu | Phe | Val | Asp | Gly | Ala | Leu | Asn | His | Ile |
| | | 275 | | | | | 280 | | | | | 285 | | | |

| Ile | Gln | Met | Ser | Lys | Val | Leu | Gly | Glu | Gln | Ile | Gly | Ser | Gly | Tyr | Pro |
| | 290 | | | | | 295 | | | | | 300 | | | | |

| Val | Trp | Pro | Val | Ala | Ile | His | Gly | His | Tyr | Ala | Asp | Ala | Gly | Asp | Ser |
| 305 | | | | | 310 | | | | | 315 | | | | | 320 |

| Ala | Ala | Leu | Leu | Ser | Gly | Ala | Leu | Asn | Val | Pro | Met | Leu | Phe | Thr | Gly |
| | | | | 325 | | | | | 330 | | | | | 335 | |

| His | Ser | Leu | Gly | Arg | Asp | Lys | Leu | Glu | Gln | Leu | Leu | Ala | Gln | Gly | Arg |
| | | | 340 | | | | | 345 | | | | | 350 | | |

| Lys | Ser | Lys | Asp | Glu | Ile | Asn | Ser | Thr | Tyr | Lys | Ile | Met | Arg | Arg | Ile |
| | | 355 | | | | | 360 | | | | | 365 | | | |

| Glu | Ala | Glu | Glu | Leu | Thr | Leu | Asp | Ala | Ser | Glu | Ile | Val | Ile | Thr | Ser |
| | 370 | | | | | 375 | | | | | 380 | | | | |

| Thr | Arg | Gln | Glu | Ile | Asp | Glu | Gln | Trp | Arg | Leu | Tyr | Asp | Gly | Phe | Asp |
| 385 | | | | | 390 | | | | | 395 | | | | | 400 |

| Pro | Ile | Leu | Glu | Arg | Lys | Leu | Arg | Ala | Arg | Ile | Lys | Arg | Asn | Val | Ser |
| | | | | 405 | | | | | 410 | | | | | 415 | |

| Cys | Tyr | Gly | Arg 420 | Phe | Met | Pro | Arg 425 | Met | Ala | Val | Ile | Pro 430 | Pro | Gly | Met |
|---|---|---|---|---|---|---|---|---|---|---|---|---|---|---|---|
| Glu | Phe | His 435 | His | Ile | Val | Pro | His 440 | Glu | Gly | Asp | Met | Asp 445 | Gly | Glu | Thr |
| Glu | Gly 450 | Ser | Glu | Asp | Gly | Lys 455 | Thr | Pro | Asp | Pro | Pro 460 | Ile | Trp | Ala | Glu |
| Ile 465 | Met | Arg | Phe | Phe | Ser 470 | Asn | Pro | Arg | Lys | Pro 475 | Met | Ile | Leu | Ala | Leu 480 |
| Ala | Arg | Pro | Asp | Pro 485 | Lys | Lys | Asn | Leu | Thr 490 | Thr | Leu | Val | Lys 495 | Ala | Phe |
| Gly | Glu | Cys | Arg 500 | Pro | Leu | Arg | Glu | Leu 505 | Ala | Asn | Leu | Thr 510 | Leu | Ile | Met |
| Gly | Asn | Arg 515 | Asp | Asn | Ile | Asp | Glu 520 | Met | Ser | Ser | Thr | Asn 525 | Ser | Ala | Leu |
| Leu | Leu 530 | Ser | Ile | Leu | Lys | Met 535 | Ile | Asp | Lys | Tyr | Asp 540 | Leu | Tyr | Gly | Gln |
| Val 545 | Ala | Tyr | Pro | Lys | His 550 | His | Lys | Gln | Ser | Asp 555 | Val | Pro | Asp | Ile | Tyr 560 |
| Arg | Leu | Ala | Ala | Lys 565 | Thr | Lys | Gly | Val | Phe 570 | Ile | Asn | Pro | Ala | Phe 575 | Ile |
| Glu | Pro | Phe | Gly 580 | Leu | Thr | Leu | Ile | Glu 585 | Ala | Ala | Ala | Tyr | Gly 590 | Leu | Pro |
| Met | Val | Ala | Thr 595 | Lys | Asn | Gly | Gly 600 | Pro | Val | Asp | Ile | His 605 | Arg | Val | Leu |
| Asp | Asn 610 | Gly | Leu | Leu | Val | Asp 615 | Pro | His | Asp | Gln | Gln 620 | Ala | Ile | Ala | Asp |
| Ala 625 | Leu | Leu | Lys | Leu | Val 630 | Ala | Asp | Lys | Gln | Leu 635 | Trp | Ala | Lys | Cys | Arg 640 |
| Ala | Asn | Gly | Leu | Lys 645 | Asn | Ile | His | Leu | Phe 650 | Ser | Trp | Pro | Glu | His 655 | Cys |
| Lys | Thr | Tyr | Leu 660 | Ser | Arg | Ile | Ala | Ser 665 | Cys | Lys | Pro | Arg | Gln 670 | Pro | Arg |
| Trp | Leu | Arg 675 | Ser | Ile | Asp | Asp | Asp 680 | Glu | Asn | Ser | Glu | Thr 685 | Asp | Ser |
| Pro | Ser 690 | Asp | Ser | Leu | Arg | Asp 695 | Ile | His | Asp | Ile | Ser 700 | Leu | Asn | Leu | Arg |
| Phe | Ser 705 | Leu | Asp | Gly | Glu | Lys 710 | Asn | Asp | Asn | Lys | Glu 715 | Asn | Ala | Asp | Asn 720 |
| Thr | Leu | Asp | Pro | Glu 725 | Val | Arg | Arg | Ser | Lys 730 | Leu | Glu | Asn | Ala | Val 735 | Leu |
| Ser | Leu | Ser | Lys 740 | Gly | Ala | Leu | Lys | Ser 745 | Thr | Ser | Lys | Ser | Trp 750 | Ser | Ser |
| Asp | Lys | Ala 755 | Asp | Gln | Asn | Pro | Gly 760 | Ala | Gly | Lys | Phe | Pro 765 | Ala | Ile | Arg |
| Arg | Arg 770 | Arg | His | Ile | Phe | Val 775 | Ile | Ala | Val | Asp | Cys 780 | Asp | Ala | Ser | Ser |
| Gly | Leu 785 | Ser | Gly | Ser | Val 790 | Lys | Lys | Ile | Phe | Glu 795 | Ala | Val | Glu | Lys | Glu 800 |
| Arg | Ala | Glu | Gly | Ser 805 | Ile | Gly | Phe | Ile | Leu 810 | Ala | Thr | Ser | Phe | Asn 815 | Ile |
| Ser | Glu | Val | Gln 820 | Ser | Phe | Leu | Leu | Ser 825 | Glu | Gly | Met | Asn | Pro 830 | Thr | Asp |
| Phe | Asp | Ala 835 | Tyr | Ile | Cys | Asn | Ser 840 | Gly | Gly | Asp | Leu | Tyr 845 | Tyr | Ser | Ser |

| | | | | | | | | | | | | | | |
|---|---|---|---|---|---|---|---|---|---|---|---|---|---|---|
| Phe | His | Ser | Glu | Gln | Asn | Pro | Phe | Val | Val | Asp | Leu | Tyr | Tyr | His | Ser |
| | 850 | | | | 855 | | | | | 860 | | | | | |
| His | Ile | Glu | Tyr | Arg | Trp | Gly | Gly | Glu | Gly | Leu | Arg | Lys | Thr | Leu | Val |
| 865 | | | | | 870 | | | | | 875 | | | | | 880 |
| Arg | Trp | Ala | Ala | Ser | Ile | Ile | Asp | Lys | Asn | Gly | Glu | Asn | Gly | Asp | His |
| | | | | 885 | | | | | 890 | | | | | 895 | |
| Ile | Val | Val | Glu | Asp | Glu | Asp | Asn | Ser | Ala | Asp | Tyr | Cys | Tyr | Thr | Phe |
| | | | 900 | | | | | 905 | | | | | 910 | | |
| Lys | Val | Cys | Lys | Pro | Gly | Thr | Val | Pro | Pro | Ser | Lys | Glu | Leu | Arg | Lys |
| | | 915 | | | | | 920 | | | | | 925 | | | |
| Val | Met | Arg | Ile | Gln | Ala | Leu | Arg | Cys | His | Ala | Val | Tyr | Cys | Gln | Asn |
| | 930 | | | | | 935 | | | | | 940 | | | | |
| Gly | Ser | Arg | Ile | Asn | Val | Ile | Pro | Val | Leu | Ala | Ser | Arg | Ser | Gln | Ala |
| 945 | | | | | 950 | | | | | 955 | | | | | 960 |
| Leu | Arg | Tyr | Leu | Tyr | Leu | Arg | Trp | Gly | Met | Asp | Leu | Ser | Lys | Leu | Val |
| | | | | 965 | | | | | 970 | | | | | 975 | |
| Val | Phe | Val | Gly | Glu | Ser | Gly | Asp | Thr | Asp | Tyr | Glu | Gly | Leu | Ile | Gly |
| | | | 980 | | | | | 985 | | | | | 990 | | |
| Gly | Leu | Arg | Lys | Ala | Val | Ile | Met | Lys | Gly | Leu | Cys | Thr | Asn | Ala | Ser |
| | | 995 | | | | | 1000 | | | | | 1005 | | | |
| Ser | Leu | Ile | His | Gly | Asn | Arg | Asn | Tyr | Pro | Leu | Ser | Asp | Val | Leu | Pro |
| | 1010 | | | | | 1015 | | | | | 1020 | | | | |
| Phe | Asp | Ser | Pro | Asn | Val | Ile | Gln | Ala | Asp | Glu | Glu | Cys | Ser | Ser | Thr |
| 1025 | | | | | 1030 | | | | | 1035 | | | | | 1040 |
| Glu | Ile | Arg | Cys | Leu | Leu | Glu | Lys | Leu | Ala | Val | Leu | Lys | Gly | | |
| | | | | 1045 | | | | | 1050 | | | | | | |

( 2 ) INFORMATION FOR SEQ ID NO:5:

( i ) SEQUENCE CHARACTERISTICS:
        ( A ) LENGTH: 2930 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Solanum tuberosum ( i x ) FEATURE:
        ( A ) NAME/KEY: CDS
        ( B ) LOCATION: 118..2841
        ( D ) OTHER INFORMATION: /note= "Sucrose-Phospahte-Synthase"

( x i ) SEQUENCE DESCRIPTION: SEQ ID NO:5:

```
ATTTTTTCT  CTAAATTCTC  TCTCACTGTC  CTTATCATTT  CACCACCTCC  ATAAATCTAG          60

AAACATCTTT  TCTATTCCGT  TAATCTCTCT  AGCACACGGC  GGAGTGCGGC  GGAGGAG           117
```

| ATG | GCG | GGA | AAC | GAC | TGG | ATT | AAC | AGT | TAC | TTA | GAG | GCG | ATA | CTG | GAT | 165 |
|---|---|---|---|---|---|---|---|---|---|---|---|---|---|---|---|---|
| Met | Ala | Gly | Asn | Asp | Trp | Ile | Asn | Ser | Tyr | Leu | Glu | Ala | Ile | Leu | Asp | |
| 1 | | | | 5 | | | | | 10 | | | | | 15 | | |

| GTA | GGA | CCA | GGG | CTA | GAT | GAT | AAG | AAA | TCA | TCG | TTG | TTG | TTG | AGA | GAA | 213 |
|---|---|---|---|---|---|---|---|---|---|---|---|---|---|---|---|---|
| Val | Gly | Pro | Gly | Leu | Asp | Asp | Lys | Lys | Ser | Ser | Leu | Leu | Leu | Arg | Glu | |
| | | | 20 | | | | | 25 | | | | | 30 | | | |

| AGA | GGG | AGG | TTT | AGT | CCG | ACG | AGG | TAC | TTT | GTT | GAG | GAA | GTT | ATT | ACT | 261 |
|---|---|---|---|---|---|---|---|---|---|---|---|---|---|---|---|---|
| Arg | Gly | Arg | Phe | Ser | Pro | Thr | Arg | Tyr | Phe | Val | Glu | Glu | Val | Ile | Thr | |
| | | 35 | | | | | 40 | | | | | 45 | | | | |

| GGA | TTC | GAT | GAG | ACT | GAT | TTG | CAT | CGC | TCG | TGG | ATC | CGA | GCA | CAA | GCT | 309 |
|---|---|---|---|---|---|---|---|---|---|---|---|---|---|---|---|---|
| Gly | Phe | Asp | Glu | Thr | Asp | Leu | His | Arg | Ser | Trp | Ile | Arg | Ala | Gln | Ala | |
| | 50 | | | | | 55 | | | | | 60 | | | | | |

-continued

| | | | | | | | | | | | | | | | | |
|---|---|---|---|---|---|---|---|---|---|---|---|---|---|---|---|---|
| ACT | CGG | AGT | CCG | CAG | GAG | AGG | AAT | ACT | AGG | CTC | GAG | AAT | ATG | TGC | TGG | 357 |
| Thr | Arg | Ser | Pro | Gln | Glu | Arg | Asn | Thr | Arg | Leu | Glu | Asn | Met | Cys | Trp | |
| 65 | | | | 70 | | | | | 75 | | | | | | 80 | |
| AGG | ATT | TGG | AAT | TTG | GCT | CGC | CAG | AAA | AAG | CAG | CTT | GAG | GGA | GAG | CAA | 405 |
| Arg | Ile | Trp | Asn | Leu | Ala | Arg | Gln | Lys | Lys | Gln | Leu | Glu | Gly | Glu | Gln | |
| | | | | 85 | | | | | 90 | | | | | 95 | | |
| GCT | CAG | TGG | ATG | GCA | AAA | CGC | CGT | CAA | GAA | CGT | GAG | AGA | GGT | CGC | AGA | 453 |
| Ala | Gln | Trp | Met | Ala | Lys | Arg | Arg | Gln | Glu | Arg | Glu | Arg | Gly | Arg | Arg | |
| | | | 100 | | | | | 105 | | | | | 110 | | | |
| GAA | GCA | GTT | GCT | GAT | ATG | TCA | GAG | GAT | CTA | TCT | GAG | GGA | GAG | AAA | GGA | 501 |
| Glu | Ala | Val | Ala | Asp | Met | Ser | Glu | Asp | Leu | Ser | Glu | Gly | Glu | Lys | Gly | |
| | | 115 | | | | | 120 | | | | | 125 | | | | |
| GAT | ATA | GTC | GCT | GAC | ATG | TCA | TCT | CAT | GGT | GAA | AGT | ACC | AGA | GGC | CGA | 549 |
| Asp | Ile | Val | Ala | Asp | Met | Ser | Ser | His | Gly | Glu | Ser | Thr | Arg | Gly | Arg | |
| | 130 | | | | | 135 | | | | | 140 | | | | | |
| TTG | CCT | AGA | ATC | AGT | TCT | GTT | GAG | ACA | ATG | GAA | GCA | TGG | GTC | AGT | CAG | 597 |
| Leu | Pro | Arg | Ile | Ser | Ser | Val | Glu | Thr | Met | Glu | Ala | Trp | Val | Ser | Gln | |
| 145 | | | | | 150 | | | | | 155 | | | | | 160 | |
| CAG | AGA | GGA | AAG | AAG | CTT | TAT | ATC | GTG | CTT | ATA | AGT | TTA | CAT | GGT | TTA | 645 |
| Gln | Arg | Gly | Lys | Lys | Leu | Tyr | Ile | Val | Leu | Ile | Ser | Leu | His | Gly | Leu | |
| | | | | 165 | | | | | 170 | | | | | 175 | | |
| ATT | CGG | GGT | GAG | AAT | ATG | GAG | CTT | GGA | CGG | GAT | TCT | GAT | ACT | GGT | GGT | 693 |
| Ile | Arg | Gly | Glu | Asn | Met | Glu | Leu | Gly | Arg | Asp | Ser | Asp | Thr | Gly | Gly | |
| | | | | 180 | | | | | 185 | | | | | 190 | | |
| CAG | GTG | AAG | TAT | GTA | GTT | GGA | GCA | ACT | GTT | GCA | CAA | GGT | CGT | TTG | TCA | 741 |
| Gln | Val | Lys | Tyr | Val | Val | Gly | Ala | Thr | Val | Ala | Gln | Gly | Arg | Leu | Ser | |
| | | 195 | | | | | 200 | | | | | 205 | | | | |
| AAG | GAT | GAA | ATA | AAC | TCA | ACC | TAC | AAG | ATA | ATG | CGG | AGA | ATA | GAG | GCT | 789 |
| Lys | Asp | Glu | Ile | Asn | Ser | Thr | Tyr | Lys | Ile | Met | Arg | Arg | Ile | Glu | Ala | |
| | 210 | | | | | 215 | | | | | 220 | | | | | |
| GAA | GAA | TTA | ACT | CTT | GAT | GCT | TCC | GAA | ATT | GTC | ATC | ACT | AGT | ACA | AGA | 837 |
| Glu | Glu | Leu | Thr | Leu | Asp | Ala | Ser | Glu | Ile | Val | Ile | Thr | Ser | Thr | Arg | |
| 225 | | | | | 230 | | | | | 235 | | | | | 240 | |
| CAG | GAG | ATT | GAC | GAG | CAA | TGG | CGT | TTG | TAT | GAT | GGG | TTT | GAT | CCA | ATA | 885 |
| Gln | Glu | Ile | Asp | Glu | Gln | Trp | Arg | Leu | Tyr | Asp | Gly | Phe | Asp | Pro | Ile | |
| | | | | 245 | | | | | 250 | | | | | 255 | | |
| TTA | GAG | CGT | AAG | TTA | CGT | GCA | AGG | ATC | AAG | CGC | AAT | GTC | AGC | TGT | TAT | 933 |
| Leu | Glu | Arg | Lys | Leu | Arg | Ala | Arg | Ile | Lys | Arg | Asn | Val | Ser | Cys | Tyr | |
| | | | 260 | | | | | 265 | | | | | 270 | | | |
| GGC | AGG | TTT | ATG | CCT | CGT | ATG | GCT | GTA | ATT | CCT | CCT | GGG | ATG | GAG | TTC | 981 |
| Gly | Arg | Phe | Met | Pro | Arg | Met | Ala | Val | Ile | Pro | Pro | Gly | Met | Glu | Phe | |
| | | 275 | | | | | 280 | | | | | 285 | | | | |
| CAC | CAT | ATT | GTG | CCA | CAT | GAA | GGT | GAC | ATG | GAT | GGT | GAA | ACA | GAA | GGA | 1029 |
| His | His | Ile | Val | Pro | His | Glu | Gly | Asp | Met | Asp | Gly | Glu | Thr | Glu | Gly | |
| | 290 | | | | | 295 | | | | | 300 | | | | | |
| AGT | GAA | GAT | GGA | AAG | ACC | CCG | GAT | CCA | CCT | ATT | TGG | GCA | GAG | ATT | ATG | 1077 |
| Ser | Glu | Asp | Gly | Lys | Thr | Pro | Asp | Pro | Pro | Ile | Trp | Ala | Glu | Ile | Met | |
| 305 | | | | | 310 | | | | | 315 | | | | | 320 | |
| CGC | TTC | TTT | TCT | AAT | CCA | AGG | AAG | CCT | ATG | ATA | CTC | GCA | CTT | GCT | AGG | 1125 |
| Arg | Phe | Phe | Ser | Asn | Pro | Arg | Lys | Pro | Met | Ile | Leu | Ala | Leu | Ala | Arg | |
| | | | | 325 | | | | | 330 | | | | | 335 | | |
| CCT | GAT | CCC | AAG | AAG | AAC | CTC | ACT | ACT | TTA | GTG | AAA | GCA | TTT | GGT | GAA | 1173 |
| Pro | Asp | Pro | Lys | Lys | Asn | Leu | Thr | Thr | Leu | Val | Lys | Ala | Phe | Gly | Glu | |
| | | | 340 | | | | | 345 | | | | | 350 | | | |
| TGT | CGT | CCA | TTG | AGA | GAC | CTT | GCT | AAT | CTT | ACT | TTG | ATA | ATG | GGT | AAT | 1221 |
| Cys | Arg | Pro | Leu | Arg | Asp | Leu | Ala | Asn | Leu | Thr | Leu | Ile | Met | Gly | Asn | |
| | | 355 | | | | | 360 | | | | | 365 | | | | |
| CGA | GAT | AAT | ATC | GAC | GAA | ATG | TCT | AGC | ACC | AAT | TCT | GCA | CTT | CTT | CTT | 1269 |
| Arg | Asp | Asn | Ile | Asp | Glu | Met | Ser | Ser | Thr | Asn | Ser | Ala | Leu | Leu | Leu | |
| | 370 | | | | | 375 | | | | | 380 | | | | | |

-continued

| | | | | | | | | | | | | | | | | |
|---|---|---|---|---|---|---|---|---|---|---|---|---|---|---|---|---|
| TCA | ATC | TTG | AAG | ATG | ATA | GAT | AAG | TAT | GAT | CTT | TAT | GGT | CTA | GTA | GCT | 1317 |
| Ser | Ile | Leu | Lys | Met | Ile | Asp | Lys | Tyr | Asp | Leu | Tyr | Gly | Leu | Val | Ala | |
| 385 | | | | 390 | | | | | 395 | | | | | | 400 | |
| TAT | CCT | AAA | CAC | CAC | AAG | CAG | TCA | GAT | GTT | CCT | GAT | ATC | TAC | CGT | CTT | 1365 |
| Tyr | Pro | Lys | His | His | Lys | Gln | Ser | Asp | Val | Pro | Asp | Ile | Tyr | Arg | Leu | |
| | | | | 405 | | | | | 410 | | | | | 415 | | |
| GCT | GCA | AAG | ACT | AAG | GGT | GTT | TTT | ATT | AAT | CCA | GCT | TTT | ATT | GAG | CCT | 1413 |
| Ala | Ala | Lys | Thr | Lys | Gly | Val | Phe | Ile | Asn | Pro | Ala | Phe | Ile | Glu | Pro | |
| | | | 420 | | | | | 425 | | | | | 430 | | | |
| TTT | GGA | CTG | ACT | TTG | ATT | GAG | GCA | GCA | GCT | TAT | GGT | CTC | CCA | ATG | GTA | 1461 |
| Phe | Gly | Leu | Thr | Leu | Ile | Glu | Ala | Ala | Ala | Tyr | Gly | Leu | Pro | Met | Val | |
| | | 435 | | | | | 440 | | | | | 445 | | | | |
| GCC | ACA | AAA | AAT | GGA | GGA | CCT | GTT | GAT | ATA | CAT | AGG | GTT | CTT | GAC | AAT | 1509 |
| Ala | Thr | Lys | Asn | Gly | Gly | Pro | Val | Asp | Ile | His | Arg | Val | Leu | Asp | Asn | |
| | 450 | | | | | 455 | | | | | 460 | | | | | |
| GGT | CTC | TTA | GTG | GAT | CCC | CAT | GAT | CAG | CAG | GCA | ATT | GCT | GAT | GCT | CTT | 1557 |
| Gly | Leu | Leu | Val | Asp | Pro | His | Asp | Gln | Gln | Ala | Ile | Ala | Asp | Ala | Leu | |
| 465 | | | | 470 | | | | | 475 | | | | | 480 | | |
| TTG | AAG | TTG | GTT | GCT | GAT | AAG | CAA | CTG | TGG | GCT | AAA | TGC | AGG | GCA | AAT | 1605 |
| Leu | Lys | Leu | Val | Ala | Asp | Lys | Gln | Leu | Trp | Ala | Lys | Cys | Arg | Ala | Asn | |
| | | | | 485 | | | | | 490 | | | | | 495 | | |
| GGA | TTA | AAA | AAT | ATC | CAC | CTT | TTC | TCA | TGG | CCC | GAG | CAC | TGT | AAA | ACT | 1653 |
| Gly | Leu | Lys | Asn | Ile | His | Leu | Phe | Ser | Trp | Pro | Glu | His | Cys | Lys | Thr | |
| | | | 500 | | | | | 505 | | | | | 510 | | | |
| TAT | CTA | TCC | CGG | ATA | GCT | AGC | TGC | AAA | CCG | AGG | CAA | CAT | TCC | TTG | AGA | 1701 |
| Tyr | Leu | Ser | Arg | Ile | Ala | Ser | Cys | Lys | Pro | Arg | Gln | His | Ser | Leu | Arg | |
| | | 515 | | | | | 520 | | | | | 525 | | | | |
| GAT | ATT | CAT | GAT | ATA | TCT | CTG | AAT | TTG | AGA | TTT | TCA | TTA | GAT | GGG | GAA | 1749 |
| Asp | Ile | His | Asp | Ile | Ser | Leu | Asn | Leu | Arg | Phe | Ser | Leu | Asp | Gly | Glu | |
| | 530 | | | | | 535 | | | | | 540 | | | | | |
| AAG | AAT | GAC | AAT | AAA | GAA | AAT | GCT | GAT | AAT | ACA | TTA | GAC | CCC | GAA | GTT | 1797 |
| Lys | Asn | Asp | Asn | Lys | Glu | Asn | Ala | Asp | Asn | Thr | Leu | Asp | Pro | Glu | Val | |
| 545 | | | | | 550 | | | | | 555 | | | | | 560 | |
| CGA | AGG | AGC | AAG | TTA | GAG | AAT | GCT | GTT | TTG | TCC | TTA | TCT | AAG | GGT | GCA | 1845 |
| Arg | Arg | Ser | Lys | Leu | Glu | Asn | Ala | Val | Leu | Ser | Leu | Ser | Lys | Gly | Ala | |
| | | | | 565 | | | | | 570 | | | | | 575 | | |
| CTG | AAG | AGC | ACA | TCA | AAA | TCT | TGG | TCG | TCA | GAC | AAG | GCA | GAC | CAA | AAT | 1893 |
| Leu | Lys | Ser | Thr | Ser | Lys | Ser | Trp | Ser | Ser | Asp | Lys | Ala | Asp | Gln | Asn | |
| | | | 580 | | | | | 585 | | | | | 590 | | | |
| CCT | GGT | GCT | GGT | AAA | TTC | CCA | GCG | ATT | AGG | AGG | AGG | CGA | CAT | ATT | TTT | 1941 |
| Pro | Gly | Ala | Gly | Lys | Phe | Pro | Ala | Ile | Arg | Arg | Arg | Arg | His | Ile | Phe | |
| | | 595 | | | | | 600 | | | | | 605 | | | | |
| GTT | ATT | GCA | GTG | GAT | TGT | GAT | GCT | AGC | TCA | GGA | CTC | TCT | GGA | AGT | ATG | 1989 |
| Val | Ile | Ala | Val | Asp | Cys | Asp | Ala | Ser | Ser | Gly | Leu | Ser | Gly | Ser | Met | |
| | 610 | | | | | 615 | | | | | 620 | | | | | |
| AAA | AAG | ATA | TTT | GAG | GCT | GTA | GAG | AAG | GAA | AGG | GCA | GAG | GGT | TCC | ATT | 2037 |
| Lys | Lys | Ile | Phe | Glu | Ala | Val | Glu | Lys | Glu | Arg | Ala | Glu | Gly | Ser | Ile | |
| 625 | | | | 630 | | | | | 635 | | | | | 640 | | |
| GGA | TTT | ATC | CTT | GCT | ACA | TCT | TTC | AAT | ATA | TCA | GAA | GTA | CAG | TCT | TTC | 2085 |
| Gly | Phe | Ile | Leu | Ala | Thr | Ser | Phe | Asn | Ile | Ser | Glu | Val | Gln | Ser | Phe | |
| | | | | 645 | | | | | 650 | | | | | 655 | | |
| CTG | CTT | TCA | GAG | GGC | ATG | AAT | CCT | ACT | GAG | CAA | AAT | CCT | TTT | GTA | GTT | 2133 |
| Leu | Leu | Ser | Glu | Gly | Met | Asn | Pro | Thr | Glu | Gln | Asn | Pro | Phe | Val | Val | |
| | | | 660 | | | | | 665 | | | | | 670 | | | |
| GAC | TTG | TAC | TAT | CAC | TCA | CAT | ATT | GAG | TAT | CGT | TGG | GGG | GGC | GAA | GGG | 2181 |
| Asp | Leu | Tyr | Tyr | His | Ser | His | Ile | Glu | Tyr | Arg | Trp | Gly | Gly | Glu | Gly | |
| | | 675 | | | | | 680 | | | | | 685 | | | | |
| TTG | AGA | AAG | ACT | TTG | GTG | CGT | TGG | GCC | GCC | TCT | ATC | ATT | GAT | AAG | AAT | 2229 |
| Leu | Arg | Lys | Thr | Leu | Val | Arg | Trp | Ala | Ala | Ser | Ile | Ile | Asp | Lys | Asn | |
| | 690 | | | | | 695 | | | | | 700 | | | | | |

| | | | | | | | | | | | | | | | | |
|---|---|---|---|---|---|---|---|---|---|---|---|---|---|---|---|---|
| GGT | GAA | AAT | GGA | GAT | CAC | ATT | GTT | GTT | GAG | GAT | GAA | GAC | AAT | TCA | GCT | 2277 |
| Gly | Glu | Asn | Gly | Asp | His | Ile | Val | Val | Glu | Asp | Glu | Asp | Asn | Ser | Ala | |
| 705 | | | | | 710 | | | | | 715 | | | | | 720 | |
| GAC | TAC | TGC | TAT | ACA | TTC | AAA | GTT | TGC | AAG | CCT | GGG | ACG | GTT | CCT | CCA | 2325 |
| Asp | Tyr | Cys | Tyr | Thr | Phe | Lys | Val | Cys | Lys | Pro | Gly | Thr | Val | Pro | Pro | |
| | | | | 725 | | | | | 730 | | | | | 735 | | |
| TCT | AAA | GAA | CTT | AGA | AAA | GTA | ATG | CGA | ATT | CAG | GCA | CTT | CGT | TGT | CAC | 2373 |
| Ser | Lys | Glu | Leu | Arg | Lys | Val | Met | Arg | Ile | Gln | Ala | Leu | Arg | Cys | His | |
| | | | 740 | | | | | 745 | | | | | 750 | | | |
| GCT | GTT | TAT | TGT | CAA | AAT | GGG | AGT | AGG | ATT | AAT | GTG | ATC | CCT | GTA | CTG | 2421 |
| Ala | Val | Tyr | Cys | Gln | Asn | Gly | Ser | Arg | Ile | Asn | Val | Ile | Pro | Val | Leu | |
| | | 755 | | | | | 760 | | | | | 765 | | | | |
| GCA | TCT | CGG | TCC | CAA | GCA | CTC | AGG | TAC | TTA | TAT | CTG | CGA | TGG | GGA | ATG | 2469 |
| Ala | Ser | Arg | Ser | Gln | Ala | Leu | Arg | Tyr | Leu | Tyr | Leu | Arg | Trp | Gly | Met | |
| | 770 | | | | | 775 | | | | | 780 | | | | | |
| GTC | CCT | GTA | CTG | GCA | TCT | CGG | TCC | CAA | GCA | CTC | AGG | TAC | TTA | TAT | CTG | 2517 |
| Val | Pro | Val | Leu | Ala | Ser | Arg | Ser | Gln | Ala | Leu | Arg | Tyr | Leu | Tyr | Leu | |
| 785 | | | | | 790 | | | | | 795 | | | | | 800 | |
| CGA | TGG | GGA | ATG | GTC | CCT | GTA | CTG | GCA | TCT | CGG | TCC | CAA | GCA | CTC | AGG | 2565 |
| Arg | Trp | Gly | Met | Val | Pro | Val | Leu | Ala | Ser | Arg | Ser | Gln | Ala | Leu | Arg | |
| | | | | 805 | | | | | 810 | | | | | 815 | | |
| TAC | TTA | TAT | CTG | CGA | TGG | GGA | ATG | GAC | TTG | TCG | AAG | TTG | GTG | GTT | TTC | 2613 |
| Tyr | Leu | Tyr | Leu | Arg | Trp | Gly | Met | Asp | Leu | Ser | Lys | Leu | Val | Val | Phe | |
| | | | 820 | | | | | 825 | | | | | 830 | | | |
| GTC | GGA | GAA | AGT | GGT | GAT | ACC | GAT | TAT | GAA | GGA | TTG | ATC | GGT | GGT | CTA | 2661 |
| Val | Gly | Glu | Ser | Gly | Asp | Thr | Asp | Tyr | Glu | Gly | Leu | Ile | Gly | Gly | Leu | |
| | | 835 | | | | | 840 | | | | | 845 | | | | |
| CGC | AAG | GCT | GTC | ATA | ATG | AAA | GGA | CTC | TGC | ACT | AAT | GCA | AGC | AGC | TTA | 2709 |
| Arg | Lys | Ala | Val | Ile | Met | Lys | Gly | Leu | Cys | Thr | Asn | Ala | Ser | Ser | Leu | |
| | 850 | | | | | 855 | | | | | 860 | | | | | |
| ATT | CAC | GGT | AAT | AGG | AAT | TAC | CCG | CTA | TCT | GAT | GTT | TTA | CCA | TTC | GAG | 2757 |
| Ile | His | Gly | Asn | Arg | Asn | Tyr | Pro | Leu | Ser | Asp | Val | Leu | Pro | Phe | Glu | |
| 865 | | | | | 870 | | | | | 875 | | | | | 880 | |
| AGC | CCT | AAT | GTC | ATC | CAA | GCG | GAT | GAG | GAA | TGT | AGC | AGC | ACC | GGA | ATC | 2805 |
| Ser | Pro | Asn | Val | Ile | Gln | Ala | Asp | Glu | Glu | Cys | Ser | Ser | Thr | Gly | Ile | |
| | | | | 885 | | | | | 890 | | | | | 895 | | |
| CGT | TCC | TTA | CTG | GAG | AAA | CTA | GCG | GTA | CTC | AAA | GGA | TAATACCCTT | | | | 2851 |
| Arg | Ser | Leu | Leu | Glu | Lys | Leu | Ala | Val | Leu | Lys | Gly | | | | | |
| | | | 900 | | | | | 905 | | | | | | | | |

CCCCCTTTGA TTGTCAAAAA CCTATATGAG CTAAGATTAT GCCATGAAAA GAATGGCCAT  2911

CCATTTGGCT TGTCTTTTG  2930

( 2 ) INFORMATION FOR SEQ ID NO:6:

( i ) SEQUENCE CHARACTERISTICS:
        ( A ) LENGTH: 908 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Ala | Gly | Asn | Asp | Trp | Ile | Asn | Ser | Tyr | Leu | Glu | Ala | Ile | Leu | Asp |
| 1 | | | | 5 | | | | | 10 | | | | | 15 | |

| | | | | | | | | | | | | | | |
|---|---|---|---|---|---|---|---|---|---|---|---|---|---|---|
| Val | Gly | Pro | Gly | Leu | Asp | Asp | Lys | Lys | Ser | Ser | Leu | Leu | Leu | Arg | Glu |
| | | | 20 | | | | | 25 | | | | | 30 | | |

| | | | | | | | | | | | | | | |
|---|---|---|---|---|---|---|---|---|---|---|---|---|---|---|
| Arg | Gly | Arg | Phe | Ser | Pro | Thr | Arg | Tyr | Phe | Val | Glu | Glu | Val | Ile | Thr |
| | | 35 | | | | | 40 | | | | | 45 | | | |

| | | | | | | | | | | | | | | |
|---|---|---|---|---|---|---|---|---|---|---|---|---|---|---|
| Gly | Phe | Asp | Glu | Thr | Asp | Leu | His | Arg | Ser | Trp | Ile | Arg | Ala | Gln | Ala |
| | 50 | | | | | 55 | | | | | 60 | | | | |

```
Thr Arg Ser Pro Gln Glu Arg Asn Thr Arg Leu Glu Asn Met Cys Trp
 65                  70                  75                   80

Arg Ile Trp Asn Leu Ala Arg Gln Lys Lys Gln Leu Glu Gly Glu Gln
                 85                  90                  95

Ala Gln Trp Met Ala Lys Arg Arg Gln Glu Arg Glu Arg Gly Arg Arg
            100                 105                 110

Glu Ala Val Ala Asp Met Ser Asp Leu Ser Glu Gly Glu Lys Gly
            115                 120             125

Asp Ile Val Ala Asp Met Ser Ser His Gly Glu Ser Thr Arg Gly Arg
    130                 135                 140

Leu Pro Arg Ile Ser Ser Val Glu Thr Met Glu Ala Trp Val Ser Gln
145                 150                 155                 160

Gln Arg Gly Lys Lys Leu Tyr Ile Val Leu Ile Ser Leu His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Gly Ala Thr Val Ala Gln Gly Arg Leu Ser
        195                 200                 205

Lys Asp Glu Ile Asn Ser Thr Tyr Lys Ile Met Arg Arg Ile Glu Ala
    210                 215                 220

Glu Glu Leu Thr Leu Asp Ala Ser Glu Ile Val Ile Thr Ser Thr Arg
225                 230                 235                 240

Gln Glu Ile Asp Glu Gln Trp Arg Leu Tyr Asp Gly Phe Asp Pro Ile
            245                 250                 255

Leu Glu Arg Lys Leu Arg Ala Arg Ile Lys Arg Asn Val Ser Cys Tyr
            260                 265                 270

Gly Arg Phe Met Pro Arg Met Ala Val Ile Pro Pro Gly Met Glu Phe
        275                 280                 285

His His Ile Val Pro His Glu Gly Asp Met Asp Gly Glu Thr Glu Gly
    290                 295                 300

Ser Glu Asp Gly Lys Thr Pro Asp Pro Pro Ile Trp Ala Glu Ile Met
305                 310                 315                 320

Arg Phe Phe Ser Asn Pro Arg Lys Pro Met Ile Leu Ala Leu Ala Arg
                325                 330                 335

Pro Asp Pro Lys Lys Asn Leu Thr Thr Leu Val Lys Ala Phe Gly Glu
            340                 345                 350

Cys Arg Pro Leu Arg Asp Leu Ala Asn Leu Thr Leu Ile Met Gly Asn
        355                 360                 365

Arg Asp Asn Ile Asp Glu Met Ser Ser Thr Asn Ser Ala Leu Leu Leu
    370                 375                 380

Ser Ile Leu Lys Met Ile Asp Lys Tyr Asp Leu Tyr Gly Leu Val Ala
385                 390                 395                 400

Tyr Pro Lys His His Lys Gln Ser Asp Val Pro Asp Ile Tyr Arg Leu
                405                 410                 415

Ala Ala Lys Thr Lys Gly Val Phe Ile Asn Pro Ala Phe Ile Glu Pro
            420                 425                 430

Phe Gly Leu Thr Leu Ile Glu Ala Ala Ala Tyr Gly Leu Pro Met Val
        435                 440                 445

Ala Thr Lys Asn Gly Gly Pro Val Asp Ile His Arg Val Leu Asp Asn
    450                 455                 460

Gly Leu Leu Val Asp Pro His Asp Gln Gln Ala Ile Ala Asp Ala Leu
465                 470                 475                 480

Leu Lys Leu Val Ala Asp Lys Gln Leu Trp Ala Lys Cys Arg Ala Asn
```

-continued

|     |     |     | 485 |     |     |     | 490 |     |     |     | 495 |     |     |
|-----|-----|-----|-----|-----|-----|-----|-----|-----|-----|-----|-----|-----|-----|
| Gly | Leu | Lys | Asn | Ile | His | Leu | Phe | Ser | Trp | Pro | Glu | His | Cys | Lys | Thr |
|     |     |     | 500 |     |     |     | 505 |     |     |     | 510 |     |     |
| Tyr | Leu | Ser | Arg | Ile | Ala | Ser | Cys | Lys | Pro | Arg | Gln | His | Ser | Leu | Arg |
|     |     |     | 515 |     |     |     | 520 |     |     |     | 525 |     |     |
| Asp | Ile | His | Asp | Ile | Ser | Leu | Asn | Leu | Arg | Phe | Ser | Leu | Asp | Gly | Glu |
|     |     |     | 530 |     |     |     | 535 |     |     |     | 540 |     |     |
| Lys | Asn | Asp | Asn | Lys | Glu | Asn | Ala | Asp | Asn | Thr | Leu | Asp | Pro | Glu | Val |
| 545 |     |     |     |     | 550 |     |     |     | 555 |     |     |     |     |     | 560 |
| Arg | Arg | Ser | Lys | Leu | Glu | Asn | Ala | Val | Leu | Ser | Leu | Ser | Lys | Gly | Ala |
|     |     |     |     | 565 |     |     |     | 570 |     |     |     |     |     | 575 |     |
| Leu | Lys | Ser | Thr | Ser | Lys | Ser | Trp | Ser | Ser | Asp | Lys | Ala | Asp | Gln | Asn |
|     |     |     | 580 |     |     |     | 585 |     |     |     | 590 |     |     |
| Pro | Gly | Ala | Gly | Lys | Phe | Pro | Ala | Ile | Arg | Arg | Arg | Arg | His | Ile | Phe |
|     |     |     | 595 |     |     |     | 600 |     |     |     | 605 |     |     |
| Val | Ile | Ala | Val | Asp | Cys | Asp | Ala | Ser | Ser | Gly | Leu | Ser | Gly | Ser | Met |
|     |     |     | 610 |     |     |     | 615 |     |     |     | 620 |     |     |
| Lys | Lys | Ile | Phe | Glu | Ala | Val | Glu | Lys | Glu | Arg | Ala | Glu | Gly | Ser | Ile |
| 625 |     |     |     |     | 630 |     |     |     | 635 |     |     |     |     |     | 640 |
| Gly | Phe | Ile | Leu | Ala | Thr | Ser | Phe | Asn | Ile | Ser | Glu | Val | Gln | Ser | Phe |
|     |     |     |     | 645 |     |     |     | 650 |     |     |     |     |     | 655 |     |
| Leu | Leu | Ser | Glu | Gly | Met | Asn | Pro | Thr | Glu | Gln | Asn | Pro | Phe | Val | Val |
|     |     |     | 660 |     |     |     | 665 |     |     |     | 670 |     |     |
| Asp | Leu | Tyr | Tyr | His | Ser | His | Ile | Glu | Tyr | Arg | Trp | Gly | Gly | Glu | Gly |
|     |     |     | 675 |     |     |     | 680 |     |     |     | 685 |     |     |
| Leu | Arg | Lys | Thr | Leu | Val | Arg | Trp | Ala | Ala | Ser | Ile | Ile | Asp | Lys | Asn |
|     |     |     | 690 |     |     |     | 695 |     |     |     | 700 |     |     |
| Gly | Glu | Asn | Gly | Asp | His | Ile | Val | Val | Glu | Asp | Glu | Asp | Asn | Ser | Ala |
| 705 |     |     |     |     | 710 |     |     |     | 715 |     |     |     |     |     | 720 |
| Asp | Tyr | Cys | Tyr | Thr | Phe | Lys | Val | Cys | Lys | Pro | Gly | Thr | Val | Pro | Pro |
|     |     |     | 725 |     |     |     | 730 |     |     |     | 735 |     |     |
| Ser | Lys | Glu | Leu | Arg | Lys | Val | Met | Arg | Ile | Gln | Ala | Leu | Arg | Cys | His |
|     |     |     | 740 |     |     |     | 745 |     |     |     | 750 |     |     |
| Ala | Val | Tyr | Cys | Gln | Asn | Gly | Ser | Arg | Ile | Asn | Val | Ile | Pro | Val | Leu |
|     |     |     | 755 |     |     |     | 760 |     |     |     | 765 |     |     |
| Ala | Ser | Arg | Ser | Gln | Ala | Leu | Arg | Tyr | Leu | Tyr | Leu | Arg | Trp | Gly | Met |
|     |     |     | 770 |     |     |     | 775 |     |     |     | 780 |     |     |
| Val | Pro | Val | Leu | Ala | Ser | Arg | Ser | Gln | Ala | Leu | Arg | Tyr | Leu | Tyr | Leu |
| 785 |     |     |     |     | 790 |     |     |     | 795 |     |     |     |     |     | 800 |
| Arg | Trp | Gly | Met | Val | Pro | Val | Leu | Ala | Ser | Arg | Ser | Gln | Ala | Leu | Arg |
|     |     |     |     | 805 |     |     |     | 810 |     |     |     |     |     | 815 |     |
| Tyr | Leu | Tyr | Leu | Arg | Trp | Gly | Met | Asp | Leu | Ser | Lys | Leu | Val | Val | Phe |
|     |     |     | 820 |     |     |     | 825 |     |     |     | 830 |     |     |
| Val | Gly | Glu | Ser | Gly | Asp | Thr | Asp | Tyr | Glu | Gly | Leu | Ile | Gly | Gly | Leu |
|     |     |     | 835 |     |     |     | 840 |     |     |     | 845 |     |     |
| Arg | Lys | Ala | Val | Ile | Met | Lys | Gly | Leu | Cys | Thr | Asn | Ala | Ser | Ser | Leu |
|     |     |     | 850 |     |     |     | 855 |     |     |     | 860 |     |     |
| Ile | His | Gly | Asn | Arg | Asn | Tyr | Pro | Leu | Ser | Asp | Val | Leu | Pro | Phe | Glu |
| 865 |     |     |     |     | 870 |     |     |     | 875 |     |     |     |     |     | 880 |
| Ser | Pro | Asn | Val | Ile | Gln | Ala | Asp | Glu | Glu | Cys | Ser | Ser | Thr | Gly | Ile |
|     |     |     |     | 885 |     |     |     | 890 |     |     |     |     |     | 895 |     |
| Arg | Ser | Leu | Leu | Glu | Lys | Leu | Ala | Val | Leu | Lys | Gly |     |     |     |     |
|     |     |     | 900 |     |     |     | 905 |     |     |     |     |     |     |